United States Patent [19]

Hayakawa et al.

[11] Patent Number: 5,587,386
[45] Date of Patent: Dec. 24, 1996

[54] OPTICALLY ACTIVE PYRIDONECARBOXYLIC ACID DERIVATIVES

[75] Inventors: Isao Hayakawa; Youichi Kimura, both of Tokyo, Japan

[73] Assignee: Daiichi Pharmaceutical Co., Ltd., Tokyo, Japan

[21] Appl. No.: 142,105

[22] Filed: Oct. 28, 1993

Related U.S. Application Data

[63] Continuation of Ser. No. 610,916, Nov. 9, 1990, abandoned, which is a continuation-in-part of Ser. No. 343,567, Apr. 27, 1989, abandoned.

[30] Foreign Application Priority Data

Apr. 27, 1988 [JP] Japan .................. 63-104625
Nov. 24, 1988 [JP] Japan .................. 63-296984

[51] Int. Cl.⁶ .............. C07D 471/04; C07D 215/56; A61K 31/47; A61K 31/44
[52] U.S. Cl. .............. 514/312; 514/278; 540/543; 540/553; 540/575; 540/597; 546/15; 546/123; 546/156; 544/231; 544/363
[58] Field of Search .................. 546/15, 123, 156; 544/231, 363; 540/543, 553, 575, 597; 514/212, 254, 312

[56] References Cited

U.S. PATENT DOCUMENTS 4,705,788  11/1987  Schriewer .................. 546/156

FOREIGN PATENT DOCUMENTS 0191185  8/1986  European Pat. Off. .
0195316  9/1986  European Pat. Off. .
341493   11/1989  European Pat. Off. .
2188317  9/1987  United Kingdom .

OTHER PUBLICATIONS

Kimura I Synthesis and Antibacterial Activity of $N_1$–2–Fluorocyclopropyl–4–Quinolone Derivatives, Research Institute, Daiichi Seiyaku Co., Ltd. 1987, Japan.

Kimura II Therapeutics in the 21st Century, The Japanese–United States Congress of Pharmaceutical Sciences, Dec. 2–7, 1987, Honolulu, Hawaii, Medicinal Chemistry, S156.

*Primary Examiner*—Mark L. Berch
*Attorney, Agent, or Firm*—Sughrue, Mion, Zinn, Macpeak & Seas

[57] ABSTRACT

$N_1$-(1,2-cis-2-halogenocyclopropyl)-substituted pyridonecarboxylic acid derivatives represented by the following formula (I) the terms of which are defined in the specification and the salts thereof are disclosed:

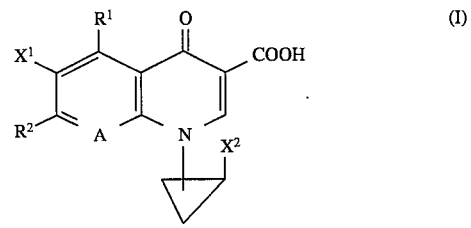

These compounds have patent antibacterial activities against a wide variety of infectious bacteria and are useful as antibacterial agents by oral or parenteral administration.

9 Claims, No Drawings

OPTICALLY ACTIVE PYRIDONECARBOXYLIC ACID DERIVATIVES

CROSS REFERENCE TO RELATED APPLICATION

This is a Continuation of application Ser. No. 07/610,916 filed on Nov. 9, 1990, abandoned which is a Continuation-in-Part of 07/343,567 filed Apr. 27, 1989 abandoned.

FIELD OF THE INVENTION

This invention relates to an antimicrobial compound useful as human and veterinary medicines, fish medicines, agricultural chemicals, and antiseptics.

BACKGROUND OF THE INVENTION

Quinolone derivatives having a condensed pyridonecarboxylic acid skeleton are known as synthetic antimicrobial agents and to provide potent antimicrobial compounds on substitution of the 1-position thereof with a cyclopropyl group.

It is further known that the 1-cyclopropylquinolone derivatives having introduced a fluorine atom to the 2-position of the cyclopropyl group in a cis-configuration with the pyridonecarboxylic acid moiety also exhibit potent antimicrobial activity as disclosed in U.S. Pat. No. 4,871,852 which corresponds to JP-A-87-12760 (the term "JP-A" as used herein means an "unexamined published Japanese patent application"). They are thought to have not only potent antimicrobial activity but improved safety. One example of the quinolone derivatives having a cis-fluorocyclopropyl group at the 1-position is shown below.

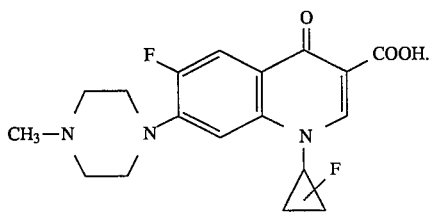

Quinolone derivatives having a cis-halogeno-cyclopropyl group, inclusive of a cis-fluorocyclopropyl group, at the 1-position as stated above possess excellent properties in antimicrobial activity and safety. In these compounds, even when they have a substituent without stereo-isomerism at the 7-position of the pyridonecarboxylic acid moiety, the halogeno-cyclopropane ring of itself provides two enantiomers attributed to the static relationship between the pyridonecarboxylic acid moiety and the halogen atom with respect to the cyclopropane ring as illustrated below;

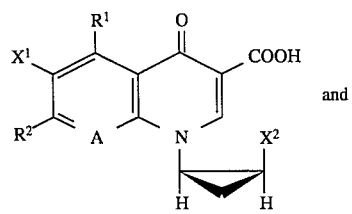

and

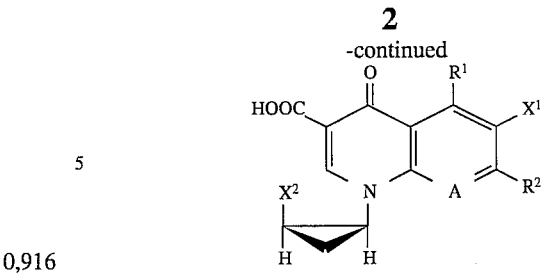

wherein $R^1$, $R^2$, A, $X^1$, and $X^2$ are hereinafter defined. These quinolone derivatives are applicable as medicines as long as they are racemates. On the other hand, when there is stereoisomerism at the 7-positioned substituent of the pyridonecarboxylic acid moiety, such quinolone derivatives contain four kinds of stereoisomers. With mixtures of the stereoisomers, it is difficult to specify the excellent species and to supply them as medicines.

SUMMARY OF THE INVENTION

In the light of the aforesaid situation, the inventors have made extensive efforts to obtain the single isomers of 1-(1,2-cis-2-fluorocyclopropyl)-substituted quinolone derivatives within the stereoisomers thereof. And they have succeeded in obtaining each of the enantiomers of a cis-2-fluorocyclopropylamine as a pure isomer. As a result of further investigations, they have also succeeded in synthesizing each of the enantiomers of a quinolone derivative which are attributed only to the static configuration of the fluorocyclopropane ring by starting from the above-described amine.

The success of obtaining the enantiomeric quinolone derivatives useful as an intermediate has made it possible to synthesize an optically active quinolone derivative comprising one kind of stereoisomer by reacting with a single isomer of the amine at introduction of a cyclic amino group to the 7-position. Each of these stereoisomers was proved more potent in antimicrobial activity as compared with the corresponding quinolone derivatives substituted with a mere cyclopropyl group and, in addition, highly safe with markedly improved selective toxicity. The present invention has been completed based on these findings.

This invention relates to an $N_1$-(1,2-cis-2-halogenocyclopropyl)-substituted pyridonecarboxylic acid derivative represented by formula (I):

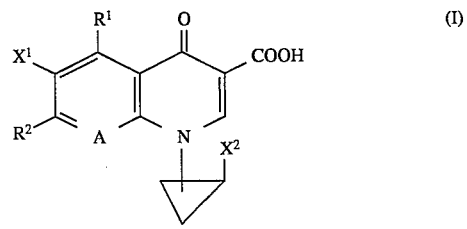

wherein $R^1$ represents a hydrogen atom, an amino group, an alkylamino group of from 1 to 3 carbon atoms, a hydroxyl group or a thiol group;

$R^2$ represents a cyclic amino group represented by the following formula:

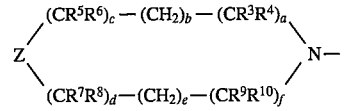

wherein a, b, c, d, e and f each independently represent an integer of 0 or 1, and at least one of a, b, c, d, e, or f is 0;

$R^3$, $R^4$, $R^5$, $R^6$, $R^7$, $R^8$, $R^9$, $R^{10}$ independently represent hydrogen atoms or alkyl groups of from 1 to 3 carbon atoms, and $R^5$ may, together with $R^6$, form a methylene chain of from 2 to 5 carbon atoms, and $R^5$ may, together with $R^9$, form a methylene chain of from 2 to 4 carbon atoms;

Z represents $>CHR^{11}$, $>NR^{12}$, $>C=NOR^{13}$, an oxygen atom or a sulfur atom;

wherein $R^{11}$ represents a hydrogen atom, an amino group, a monoalkylamino group of from 1 to 6 carbon atoms, a dialkylamino group containing from 1 to 6 carbon atoms per alkyl, a tert-butoxycarbonylamino group, a benzyloxycarbonylamino group, a hydroxyl group, an alkoxyl group of from 1 to 6 carbon atoms, a hydroxyalkyl group of from 1 to 6 carbon atoms or a 2-aminoethyl group;

$R^{12}$ represents a hydrogen atom, an alkyl group of from 1 to 6 carbon atoms, a hydroxyalkyl group of from 1 to 6 carbon atoms, a haloalkyl group of from 1 to 6 carbon atoms, a formyl group or an alkylcarbonyl group of from 2 to 7 carbon atoms;

and $R^{13}$ represents a hydrogen atom an alkyl group of from 1 to 6 carbon atoms;

A represents $C-X^3$ or a nitrogen atom;

$X^1$ and $X^2$, which may be the same or different, each represents a halogen atom;

and $X^3$ represents a halogen atom, an alkyl group of from 1 to 6 carbon atoms, an alkoxy group of from 1 to 6 carbon atoms, a cyano group, a trifluoromethyl group or a hydrogen atom;

or a pharmaceutically acceptable salt thereof.

Specifically implicit in the compounds represented by formula (I) and salts thereof are those wherein $R^2$ is a cyclic amino group which may be substituted; those wherein $R^2$ is a 4- to 7-membered cyclic amino group which may be substituted with a hydroxyl group, an alkyl group having from 1 to 6 carbon atoms, or a substituted or unsubstituted amino group; those wherein $R^2$ is a pyrrolidinyl, piperidinyl, piperazinyl, diazabicycloheptyl or diazabicyclooctyl group; those wherein $R^2$ is a cyclic amino group comprising a single stereoisomer; those wherein $R^2$ is a 3-aminopyrrolidinyl group; those wherein $R^2$ is a 7-amino-5-azaspiro[2.4]heptan-5-yl group; and those wherein $X^2$ is a fluorine atom. More specifically, the compounds according to the present invention include 7-[3-(S)-amino-1-pyrrolidinyl]-6-fluoro-1-(1,2-cis-2-fluorocyclopropyl)-4-oxo-1,4-dihydroquinoline-3-carboxylic acid, 7-[3-(S)-amino-1-pyrrolidinyl]-8-chloro-6-fluoro-1-(1,2-cis-2-fluorocyclopropyl)-4-oxo-1,4-dihydroquinoline-3-carboxylic acid, 7-[7-amino-5-azaspiro-[2.4]heptan-5-yl]-8-chloro-6-fluoro-1-(1,2-cis-2-fluorocyclopropyl)-4-oxo-1,4-dihydroquinoline-3-carboxylic acid, 7-[8-amino-6-azaspiro[3.4]octan-6-yl]-8-chloro-6-fluoro-1-(1,2-cis-2-fluorocyclopropyl)-4-oxo-1,4-dihydroquinoline-3-carboxylic acid, 7-[4-amino-3,3-dimethyl-1-pyrrolidinyl]-8-chloro-6-fluoro-1-(1,2-cis-2-fluorocyclopropyl)-4-oxo-1,4-dihydorquinoline-3-carboxylic acid, 5-amino-7-[3-(S)-amino-1-pyrrolidinyl]-6,8-difluoro-1-(1,2-cis-2-fluorocyclopropyl)-4-oxo-1,4-dihydroquinoline-3-carboxylic acid, 7-[4-(S)-amino-2-(S)-methyl-1-pyrrolidinyl]-6-fluoro-1-(1,2-cis-2-fluorocyclopropyl)-4-oxo-1,4-dihydroquinoline-3-carboxylic acid, 7-[3-(R)-[1-(S)-aminoethyl]-1-pyrrolidinyl]-8-chloro-6-fluoro-1-(1,2-cis-2-fluorocyclopropyl)-4-oxo-1,4-dihydroquinoline-3-carboxylic acid, 7-[3-amino-4-methyl-1-pyrrolidinyl]-6-fluoro-1-(1,2-cis-2-fluorocyclopropyl)-8-methoxy-4-oxo-1,4-dihydroquinoline-3-carboxylic acid, 7-[4-(S)-amino-2-(S)-methyl-1-pyrrolidinyl]-6-fluoro-1-(1,2-cis-2-fluorocyclopropyl)-8-methyl-4-oxo-1,4-dihydroquinoline-3-carboxylic acid, 5-amino-7-[7-amino-5-azaspiro[2.4]heptan-5-yl]-6,8-difluoro-1-(1,2-cis-2-fluorocyclopropyl)-4-oxo-1,4-dihydroquinoline-3-carboxylic acid; or a pharmaceutically acceptable salt thereof.

DETAILED DESCRIPTION OF THE INVENTION

In formula (I), when A represents $C-X_3$, and when $X^3$ represents a halogen atom, $X^1$ and $X^3$ each preferably represents a fluorine atom or a chlorine atom; and $X^2$, preferably represents a fluorine atom. $R^1$ represents an alkylamino group of from 1 to 3 carbon atoms, an unsubstituted amino group, a hydroxyl group, a thiol group, or a hydrogen atom, preferably an unsubstituted amino group, a methylamino group, or a hydrogen atom.

$R^2$ represents a cyclic amino group, preferably a 4- to 7-membered, and more preferably 5- to 6-membered cyclic amino group. The cyclic amino group may further contain oxygen atom(s), sulfur atom(s) and/or nitrogen atom(s), as in oxazolidinyl, morpholinyl, thiazolidinyl, thiomorpholinyl, imidazolidinyl, pyrazolidinyl, and piperazinyl groups. Of these cyclic amino groups preferred are a pyrrolidinyl group and a piperazinyl group. The cyclic amino group may have substituents, such as a polar group (e.g., a substituted or unsubstituted amino group, a substituted or unsubstituted aminoalkyl group, a 5-substituted-2-oxo-1,3-dioxol-4-ylmethyl group, a hydroxyl group) and a straight chain, branched, or cyclic alkyl group having up to 6 carbon atoms. Preferred of the polar groups are an unsubstituted amino group, an aminomethyl group, a 1-aminoethyl group, and a hydroxyl group. Preferred of the alkyl group are methyl, ethyl, propyl, gem-dimethyl and gem-diethyl groups and further, these gem-alkyl groups may preferably form a cyclopropane or cyclobutane ring which is bonded through a spiro-union to the cyclic amine skeleton. The cyclic amino group further includes a bicyclic amino group composed of crosslinking to 4- to 7-membered cyclic amino groups.

Illustrative examples of these cyclic amino groups, particularly containing the second amino moiety, are shown below;

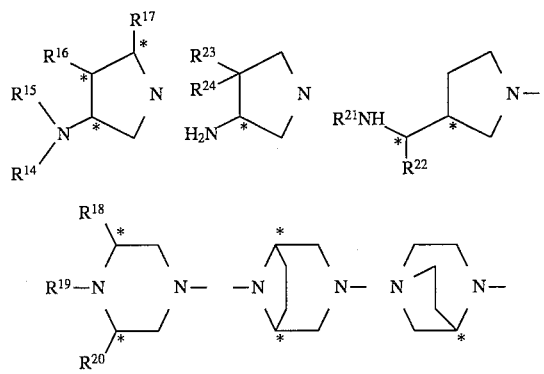

wherein $R^{14}$, $R^{15}$, $R^{16}$, $R^{17}$, which may be the same or different, each represents a hydrogen atom or an alkyl group having from 1 to 6 carbon atoms; $R^{18}$, $R^{19}$, and $R^{20}$, which may be the same or different, each represents a hydrogen atom or an alkyl group having from 1 to 6 carbon atoms, provided that the case wherein $R^{18}$, $R^{19}$, and $R^{20}$ each represents a hydrogen atom and the case wherein $R^{18}$ and $R^{20}$ each represents a hydrogen atom and $R^{19}$ represents an alkyl group having from 1 to 6 carbon atoms are excluded; $R^{21}$ and $R^{22}$, which may be the same or different, each represents a hydrogen atom or an alkyl group having from 1 to 6 carbon atoms; $R^{23}$ and $R^{24}$, which may be the same or different, each represents a hydrogen atom or an alkyl group having from 1 to 6 carbon atoms, or they may be connected to each other to form a 3- to 6-membered ring composed of methylene chains; and the asterisk indicates an asymmetric center.

Examples of these cyclic amino groups are 3-aminopyrrolidinyl, 3-methylaminopyrrolidinyl, 3-dimethylaminopyrrolidinyl, 3-ethylaminopyrrolidinyl, 3-propylaminopyrrolidinyl, 3-isopropylaminopyrrolidinyl, 3-amino-4-methylpyrrolidinyl, 3-amino-5-methylpyrrolidinyl, 3-amino-4,5-dimethylpyrrolidinyl, 3-methylamino-4-methylpyrrolidinyl, 3-methylamino-5-methylpyrrolidinyl, 3-methylamino-4,5-dimethylpyrrolidinyl, 3-dimethylamino-4-methylpyrrolidinyl, 3-dimethylamino-5-methylpyrrolidinyl, 3-dimethylamino-4,5-dimethylpyrrolidinyl, 3-dimethylamino-4-methylpyrrolidinyl, 3-dimethylamino-5-methylpyrrolidinyl, 3-dimethylamino-4,5-dimethylpyrrolidinyl, 3-methylpiperzinyl, 4-methylpiperazinyl, 3,4-dimethylpiperazinyl, 3,5-dimethylpiperazinyl, 3,4,5-trimethylpiperazinyl, 4-ethyl-3,5-dimethylpiperazinyl, 4-isopropyl-3,5-dimethylpiperazinyl, 3-aminomethylpyrrolidinyl, 3-methylaminomethylpyrrolidinyl, 3-(1-amino)ethylpyrrolidinyl, 3-(1-methylamino)ethylpyrrolidinyl, 3-(1-ethylamino)ethylpyrrolidinyl, 3-(1-amino)propylpyrrolidinyl, 3-(1-methylamino)propylpiperizinyl, 3-aminopyrrolidinyl, 3-amino-4,4-dimethylpyrrolidinyl, 7-amino-5-azaspiro[2.4]heptan-5-yl, 8-amino-6-azaspiro[3.4]-octan-6-yl, 3,4-diazabicyclo[3,2,1]octan-3-yl, 9-methyl-3,9-diazabicyclo[3.2.1]octan-3-yl, and 9-ethyl-3,9-diazabicyclo[3.2.1]octan-3-yl.

The structure of the cyclic amino group at the 7-position has a great influence on antimicrobial activity, toxicity, oral absorption, and physical properties such as water solubility. For instance, it is known that quinolones substituted by 3-aminopyrrolidinyl groups have strong antimicrobial spectra against a broad range of microorganisms covering Gram-positive to Gram-negative bacteria. Some quinolone derivatives of this type, however, are susceptible to metabolism or only show low water-solubility.

3-Aminopyrrolidinyl groups having a spiro ring at the carbon atom adjacent to the amine group thereof provide quinolone derivatives exhibit improved oral absorption rate and improved in vivo stability against metabolism while retaining potent antimicrobial activity. The compounds of this type have also been proved less causative of convulsion which is known as a side effect of quinolone type synthetic antimicrobials.

Further, 3-aminomethylpyrrolidinyl groups in which an amino group is bonded to a pyrrolidinyl group via a carbon atom provide quinolone derivatives exhibiting enhanced antimicrobial activity against Gram-positive bacteria. In particular, the quinolones of this type in which the carbon atom linking the amino and pyrrolidinyl groups is substituted with one or two alkyl group(s) were found to exhibit improved oral absorption rate, safety, and water solubility over those without such substituent(s).

Additionally preferred as cyclic amino groups are piperazine groups, such as alkylpiperazine groups and piperazine groups having a spiro ring.

Examples of cyclic amino groups having substituents other than an amino group are 3-hydroxypyrrolidinyl, 3-mercaptopyrrolidinyl, 3-hydroxy-4-methylpyrrolidinyl, 3-mercapto-4-methylpyrrolidinyl, morpholino, thiomorpholino, 2-methylmorpholino, 2-methylthiomorpholino, 2,6-dimethylmorpholino, 2,6-dimethylthiomorpholino, 2,2-dimethylmorpholino, and 2,2-dimethylthiomorpholino groups.

The cyclic amino group is bonded to the 7-position of the pyridonecarboxylic acid skeleton preferably at the nitrogen atom of the cyclic amino group. As a matter of course, it may be bonded at the other atom, i.e., a carbon atom of the cyclic amino group.

The steroisomerism of the cyclic amine moiety at the 7-position is explained below. In cases where a cyclic amine has isomers, if it is reacted in the form of an isomeric mixture with a 1-(1,2-cis-halogenocyclopropyl)quinolone derivative, the resulting quinolone derivative should be a mixture of diasteromers based on the steric relation with the 1,2-cis-2-halogenocyclopropyl group at the 1-position. In this cases, therefore, it is necessary that only one of the isomers of the starting amine should be reacted.

The functional group of the cyclic amino group at the 7-position such as amino, hydroxy and thiol groups may be protected by a conventional protective group prior to the substitution with the quinolone skeleton. The examples of such protective groups include alkoxycarbonyl groups such as t-butoxycarbonyl group, 2,2,2-trichloroethoxycarbonyl group and the like; aralkyloxycarbonyl groups such as benzyloxycarbonyl group, p-methoxybenzyloxycarbonyl group, p-nitrobenzyloxycarbonyl group and the like; acyl groups such as acetyl group, methoxyacetyl group, trifluoroacetyl group, chloroacetyl group, pivaloyl group, formyl group, benzoyl group and the like; alkyl or aralkyl groups such as t-butyl group, benzyl group, p-nitrobenzyl group, p-methoxybenzyl group, triphenylmethyl group and the like; ethers such a methoxymethyl group, t-butoxymethyl group, 2,2,2-trichloroethoxymethyl group, tetrahydrofuran-2-yl group and the like; silyl groups such as trimethylsilyl group, isopropyldimethylsilyl group, t-butyldimethylsilyl group, t-butyldiphenylsilyl group, tribenzylsilyl group and the like.

The 1,2-cis-2-halogenocyclopropyl group at the $N_1$-position is described below. Introduction of a halogen atom to the cyclopropyl group, particularly a fluorine atom, brings about an effect to reduce lipophilicity of the whole molecule. It is known that drugs are more likely to be distributed to the central nervous system as lipophilicity thereof increases. In this connection, introduction of the 1,2-cis-2-halogeno-cyclopropyl group yields quinolones having reduced toxicity while retaining excellent antimicrobial activity as compared with the corresponding 1-cyclopropyl-quinolones. The halogen atom to be introduced includes fluorine and chlorine atoms, with a fluorine atom being preferred.

It is particularly preferable that the halogen atom and the pyridonecarboxylic acid moiety are cis with respect to the cyclopropane ring. Irrespective of whether the 7-cyclic amino group has stereoisomers or not, the quinolone derivatives of formula (I) have enantiometric pairs ascribed to the cis-2-halogenocyclo-propyl moiety at the 1-position as illustrated below. Potent activity and high safety were observed in either of these enantiomers.

More precisely, a pyridonecarboxylic acid derivative having a 2-(S)-halogeno-1-(R)-cyclopropyl group shows more patent antibacterial activity than that having a 2-(R)-halogen-1-(S)-cycloproplyl group.

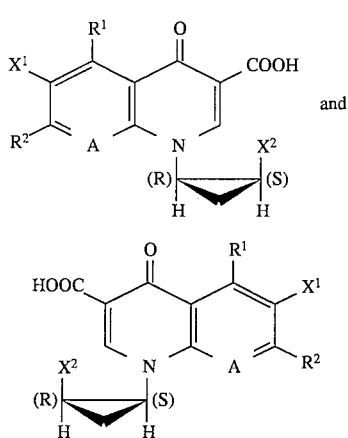

The pyridonecarboxylic acid derivatives according to the present invention include the respective free acids, acid-addition salts thereof, and the salts of the carboxyl group thereof. The acid-addition salts include inorganic acid salts, e.g., hydrochlorides, sulfates, nitrates, hydrobromides, hydroiodides, and phosphates; and organic acid salts, e.g., acetates, methanesulfonates, benzenesulfonates, toluenesulfonates, citrates, maleates, fumarates, and lactates.

The salts of the carboxyl group may be organic or inorganic and include alkali metal salts, e.g., lithium salts, sodium salts, and potassium salts, alkaline earth metal salts, e.g., magnesium salts and calcium salts; ammonium salts, triethylamine salts, N-methylglucamates, and tris(hydroxymethyl)aminomethane salts.

Some of these free acids and salts may exist as a hydrate.

Esterification of the carboxylic acid moiety of the pyridonecarboxylic acid derivatives of formula (I) gives compounds useful as synthesis intermediates or pro-drugs. For example, alkyl esters, benzyl esters, alkoxyalkyl esters, phenylalkyl esters and phenyl esters are useful as synthesis intermediates. Esters which are easily severed in the body to form free carboxylic acids are useful as pro-drugs. Examples of such esters are acetoxymethyl esters, pivaloyloxymethyl esters, ethoxycarbonyloxy esters, chlorine esters, dimethylaminoethyl esters, 5-indanyl esters, phthalidinyl esters, and oxoalkyl esters (e.g., 5-substituted-2-oxo-1,3-dioxol-4-yl-methyl esters and 3-acetoxy-2-oxobutyl esters).

A process for synthesizing the pyridonecarboxylic acid derivatives of formula (I) is illustrated below, taking the compound wherein A=C-H; $R^1$=H; $X^1$-$x^2$=F; and $R^3$=Et (ethyl group, hereinafter the same) for instance.

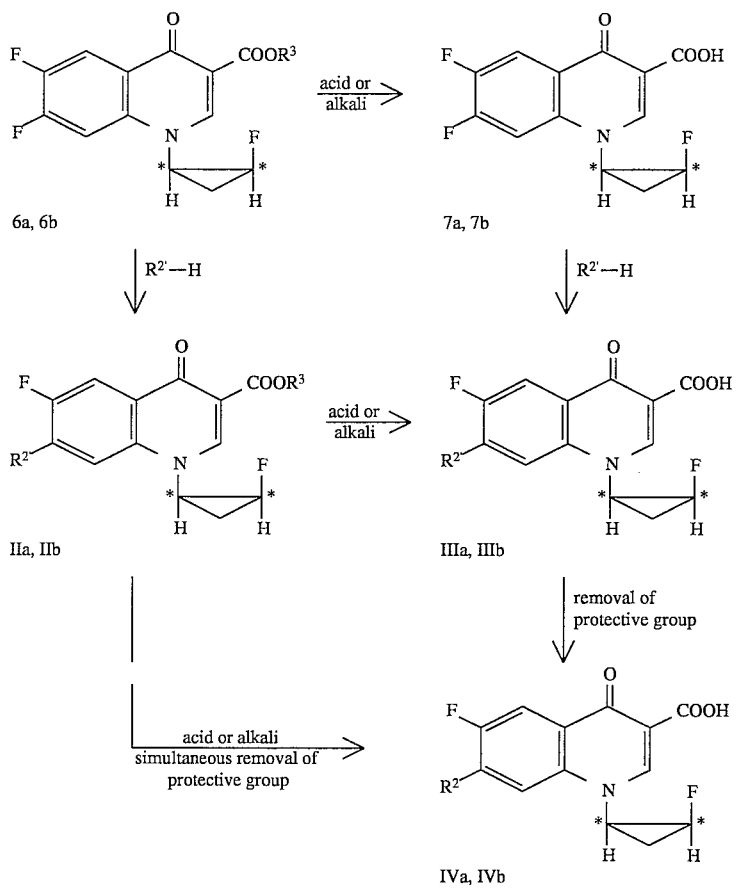

wherein $R^{2'}$ has the same meaning as $R^2$ or a cyclic amino group having the same structure as $R^2$ but being protected.

An optically active 1-(1,2-cis-2-fluorocyclopropyl)-6,7-difluoro-1,4-dihydro-4-oxoquinoline-3-carboxylic acid ethyl ester (6a) or 6b) is hydrolyzed under acidic or alkaline conditions to give a free carboxylic acid derivative (7a) or (7b). The free acid (7a) or (7b) is reacted with a cyclic amine $R^2$-H to obtain a desired compound (IIIa) or (IIIb). If necessary, a protective group is removed from the resulting compound under proper conditions selected according to the protective group to obtain a desired compound (IVa) or (IVb).

The substitution reaction with the cyclic amine can be carried out in a solvent such as dimethyl sulfoxide, pyridine, acetonitrile and 3-methoxybutanol, at a temperature of from room temperature to 150° C., preferably from 40° to 120° C., for 0.5 to 5 hours, usually from 0.5 to 2 hours.

Alternatively, the compound (6a) or (6b) is reacted with a cyclic amine under the same conditions as recited above, and the resulting compound (IIa) or (IIb) as is produced is then hydrolyzed under acidic or alkaline conditions and, if necessary, a protective group is removed, to obtain a desired compound (IIIa) or (IIIb) or (IVa) or (IVb).

The optically active cis-2-fluorocyclopropylamine can be synthesized as follows. 2-Fluorocyclopropanecarboxylic acid is reacted with (R)-(+)-α-methylbenzylamine to yield N-[1-(R)-phenylethyl]-1,2-cis-fluorocyclopropanecarboxamide. The reaction can be carried out in tetrahydrofuran in the presence of N,N-carbonyldiimidazole. The reaction may also be effected in accordance with a mixed anhydride procedure, in which the carboxylic acid is dissolved in an aprotic solvent and reacted with a halogenoformic ester in the presence of a base at low temperatures and then reacted with the benzylamine to obtain the carboxamide. The resulting carboxamide can be separated into each isomer by chromatographic techniques.

The aprotic solvent to be used in the mixed anhydride procedure is not particularly limited and includes ethers, e.g., diethyl ether, diisopropyl ether, tetrahydrofuran, 1,4-dioxane, and 1,2-dimethoxyethane; halogenated hydrocarbons, e.g., dichloromethane, chloroform, 1,2-dichloroethane, and 1,1,2,2-tetrachloroethane; aromatic hydrocarbons, e.g., benzene, toluene, and xylene; and aliphatic hydrocarbons, e.g., pentane, hexane, heptane, and cyclohexane. Commonly employed of them is tetrahydrofuran or chloroform. The water contained in the solvent to be used is usually removed beforehand.

The halogen atom in the halogenoformic ester is normally a chlorine atom. The halogenoformic ester includes methyl, ethyl, 2,2,2-trichloroethyl, phenyl, p-nitrophenyl and benzyl esters.

The base to be used may be either an organic or an inorganic. The inorganic base includes alkali metal hydroxides, carbonates and hydrogencarbonates, e.g., lithium hydroxide, sodium hydroxide, potassium hydroxide, lithium carbonate, sodium carbonate, potassium carbonate, sodium hydrogencarbonate, and potassium hydrogencarbonate. The organic base includes trialkylamines, e.g., triethylamine, tripropylamine, tributylamine, N,N-diisopropylethylamine; dialkylanilines, e.g., diethylaniline and dimethylaniline; and heterocyclic compounds, e.g., N-methylmorpholine, pyridine, and N,N-dimethylaminopyridine.

Separation of the carboxamide into optical isomers can be effected by known techniques, such as silica gel column chromatography under normal pressure or under pressure, preparative thin layer chromatography, and high performance liquid chromatography (HPLC). Separation into optical isomers can also be performed by other separation techniques generally employed, such as recrystallization and reprecipitation.

The thus separated optionally active carboxamide can be led to an optically active cis-2-fluorocyclopropanecarboxylic acid by hydrolysis. The reaction can be carried out by dissolving the carboxamide in, for example, concentrated hydrochloric acid, followed by heating. The hydrochloric acid may be replaced with sulfuric acid or nitric acid. A solvent, such as acetic acid and a lower alcohol, may be used.

The resulting carboxylic acid can be converted at once by Curtius reaction in the presence of a t-butanol to a protected cis-1-(t-butoxycarbonylamino)-2-fluorocyclopropane. The reaction can be carried out conveniently by use of diphenylphospborylazide, but the synthesis of the intermediate azide compound is not limited thereto, and general methods of synthesis can be applied.

The resulting optically active cis-2-fluorocyclopropylamine derivative can be made use of in obtaining a quinolone derivative having a cis-fluorocyclopropyl group at the 1-position as a single isomer. The quinolone derivative according to the present invention can then be obtained by reacting this isomer with the cyclic amine as described above.

The pyridonecarboxylic acid derivatives according to the present invention exhibit potent antimicrobial activity and thus can be used as human and veterinary medicines, fish medicines, agricultural chemicals, and food preservatives.

The dose of the pyridonecarboxylic acid derivatives for use as human medicines ranges from 50 mg to 1 g, preferably from 100 mg to 300 mg, per day for adult. The dose for use as veterinary medicines generally ranges from 1 mg to 200 mg, preferably from 5 mg to 100 mg, per kg of body weight per day, though more or less verying depending on the purpose of administration (therapeutic use or preventive use, etc.), the kind and size of the animal, the kind of pothogenic organisms, and the symptoms. The daily dose recited above may be divided into 2 to 4 doses per day. If necessary, the daily dose may be sometimes deviated from the above-recited range.

The pyridonecarboxylic acid derivatives of this invention are active against a wide variety of microorganisms causing various infectious diseases and capable of curing or alleviating and/or preventing the diseases caused by such phthogenes.

Illustrative examples of bacteria or bacterium-like microorganisms on which the pyridonecarboxylic acid derivatives of the invention are effective are Staphylococcus sp., *Streptococcus pyogenes, Streptococcus Haemolyticus*, enterococci, Streptococcus pneumoniae, Peptostreptococcus sp., *Neisseria gonorrhoeae, Escherichia coli*, Citrobacter sp., Shiqella sp., *Klebsiella pneumoniae*, Enterobacter sp., Serratia sp., Proteus sp., *Pseudomonas aeruginosa, Haemophilus influenzae*, Acinetobacter sp., Campylobacter sp., and Chlamidiae.

Examples of diseases caused by these pathogens include folliculitis, furuncle, carbuncle, erysipelas, phlegmon, lymphangitis/lymphadenitis, felon, subcutaneous abscess, spiradenitis, acne conglobata, infectious atheroma, perianal abscess, mastadenitis, superficial secondary infections after trauma, burn or surgery trauma, pharyngolaryngitis, acute bronchitis, tonsillitis, chronic bronchitis, bonchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteriris, adnexitis, intrauterine infections, Bartholinitis, blepharitis, hordeolum, dacryocystitis, tarsadenitis, keratohelcosis, otitis media, sinusitis, paradentitis, pericoronitis circumcoronitis, gnathitis, peritonitis, endocarditis, septicemia, meningitis, and skin infectious.

Examples of susceptible microorganisms causing veterinary infectious diseases include those of fowl, such as Escherichia sp., Salmonella sp., Pasteurella sp., Haemophilus sp., Bordetella sp., Staphylococcus sp., and Mycoplasma sp. Specific examples of veterinary diseases caused by these microorganisms include colibacillosis, pulloium disease, avian paratyphosis, fowl chlera, infectious coryza, staphylococcal infections, and mycoplasmal diseases; those of swin, such as colibacillosis, malmonelosis, pasteurellosis, haemophylus infection, atrophic rhintis, exduadative epidermitis, and mycoplasmal diseases; those for cattle, such as colibacillosis, salmonellosis, hemorrhagic septicemia, mycoplasmal diseases, bovine contageous pleurponeumonia, and bovine mastesis; those of dogs, such as coliform sepsis, salmonelosis, hemorrhagic septicemia, pyometra, and cystiris; and those of cats, such as hemorrhagic pleuritis, cystiris, chronic rhiniti, haemophylus infection, kitten diarrhea, and mycoplasmal diseases.

The compound of the present invention can be formulated into antimicrobial preparations in an appropriate dose form according to administration route selected by the conventional preparation methods. The dose form for oral administration includes tablets, powders, granules, capsules, solutions, syrups, elixiers, and oily or aqueous suspensions. Injections may contain, in addition to the active ingredient, stabilizers, antiseptics, and solubilizing agents. The solution which may contain such excipients is put in a container and further, the solution may be subjected to lyophilization or the like means to prepare solid preparations which can be dissolved on use. The container may contain either a single dose or several doses.

Dose forms for external administration include solutions, suspensions, emulsions, ointments, gels, creams, lotions, and sprays.

In the preparation of solid preparations, the active ingredient may be mixed with appropriately selected pharmaceutically acceptable excipients, such as fillers, extenders, binders, disintegrators, dissolution accelerators, wetting agents, and lubricants.

Liquid preparations include solutions, suspensions, and emulsions. They may contain excipients, such as suspension stabilizers and emulsifiers.

The compound of the present invention can be administered to animals orally either directly or as admixed to feedstuff, or its solution may be given either directly or as admixed to water or feedstuff. The compound may also be administered non-orally by, for example, injection.

The compound of the invention can be formulated into preparations for animals, such as powders, fine granules, solubilized powders, syrups, solutions, and injections, by commonly employed preparation methods.

As is the case with most inventions in the pharmaceutical arts, there are certain preferred classes of compounds which fall within formula (I). These are now discussed.

An formula (I) it is preferred that $X^2$ is a fluorine atom or $X^1$ is a fluorine atom and more preferred that both $X^2$ and $X^1$ are fluorine atoms.

In formula (I), it is preferred that the (1,2-cishalogenocyclopropyl) group at $N_1$ be a substituent which provides a stereoisomerically pure isomer (isomer embodiment) and in the isomer embodiment it is preferred that the isomer be an $N_1$-[2-(S)-halogeno-1-(R)-cyclopropyl]substituted pyridonecarboxyclic acid derivative ((S)/(R) acid embodiment), and in this last case it is preferred that halo of halogeno is a fluorine atom ((S)/(R) acid/fluorine embodiment).

Typical compounds in accordance with the present invention contain three asymmetric carbon atoms and therefore have plural stereoisomers. Among these stereoisomers, there are three kinds of isomers, i.e., enantiomers, diastereomers and epimers. Accordingly, the term "stereoisomerically" is meant to include all three kinds of isomers.

In formula (I), in the isomer embodiment and in the (S)/(R) acid embodiment, it is preferred that $R^2$ is a cyclic amino group which provides stereoisomerically pure enantiomer species (enantiomer embodiment).

In formula (I) and in the isomer embodiment and in the (S)/(R) acid embodiment, a, b, c, d, e, and f can have certain preferred values or "Sets" as now defined for Sets 1 and 2 and are often used in combination with certain preferred groups as are now discussed.

Set 1
1) a=b=O, c=d=1, e=f=O,
2) a=1, b=O, c=d=1, e=f=O,
3) a=b=O, c=d=1, e=O, f=1,
4) a=1, b=O, c=d=1, e=O, f=1,
5) a=b=c=d=1, e=O, f=1, or
6) a=1, b=O, c=d=e=f=1.

Set 2
Wherein Z represents >$CHR^{11}$; a, c and d represents 1 and b, c and f represent O.

When Set 2 is met for each of general formula (I), the isomer embodiment and the (S)/(R) acid embodiment, it is preferred that:

(1) $R^3$, $R^4$, $R^7$ and $R^8$ represent hydrogen atoms and $R^5$ and $R^6$ represent methyl groups; or (2) Z represents >$CHR^{11}$ a, c and d represent 1 and b, c and f represent O.

When limit (2) for Set 2 above is met, it is then preferred that limit (3) be met:

(3) $R^3$, $R^4$, $R^7$ and $R^8$ represent hydrogen atoms and $R^5$ and $R^6$ form a methylene chain of from 2 to 5 carbon atoms and in that case it is then most preferred that $R^{11}$ be an amino group.

In the above situation where $R^{11}$ is an amino group, certain even more preferred classes of compounds result when the following limits (4) to (7) are met.

(4) while $R^5$ and $R^6$ form a methylene chain of 2 carbon atoms; or (5) where $R^5$ and $R^6$ form a methylene chain of 3 carbon atoms or (6) where $X^2$ is a fluorine atom and $R^1$ is a hydrogen atom and A is C-$X^3$ where $X^3$ represents a hydrogen atom or a halogen atom or (7) where $R^5$ and $R^6$ represent methyl groups.

When limit (6) is met, it is then preferred that $R^5$ and $R^6$ form a methylene chain of 2 or 3 carbon atoms, more preferred if such limits on $R^5$ and $R^6$ are met that $X^1$ be a fluorine atom and, if $X^1$ is a fluorine atom, most preferred that $X^3$ be chlorine.

When limit (7) is met, i.e., $R^5$ and $R^6$ are both methyl groups, then it is:

preferred $X^2$ be a fluorine atom, $R^1$ be a hydrogen atom, A be C-$X^3$ and $X^3$ be a hydrogen atom or halogen atom;

then more preferred that $X^1$ be a fluorine atom; and then most preferred that $X^3$ be a chlorine atom.

Certain preferences also exist for the case of the enantomer embodiment.

In that case, a preferred Set is Set 3.
Set 3
1) a=b=O, c=d=1, e=f=O,
2) a=1, b=O, c=d=1, e=f=O, 3) a=b=0, c=d=1, e=0, f=1,
4) a=1, b=0, c=d=1, e=0, f=1,
5) a=b=c=d=1, e=0, f=1, or
6) a=1, b=0, c=d=e=f=1.

Another preferred Set for the enantiomer embodiment is Set 4.

Set 4

Wherein Z represents >CHR$^{11}$; a, c and d represent 1 and b, e and f represent 0.

When Set 4 is met for the enantiomer embodiment, which is a preferred embodiment of general formula (I) and the isomer embodiment and the (S)/(R) acid embodiment, it is preferred that (8) $R^3$, $R^4$, $R^7$, $R^8$ represent hydrogen atoms and $R^5$ and $R^6$ form a methylene chain of from 2 to 5 carbon atoms.

(9) $R^3$, $R^4$, $R^7$, and $R^8$ represent hydrogen atoms and $R^5$ and $R^6$ represent methyl groups.

When $R^3$, $R^4$, $R^7$, $R^8$, $R^5$ and $R^6$ meet the above criteria of limit (8) for Set 4, then two preferred classes of compounds begin:

one where $R^{11}$ is an amino group; and one where $R^{11}$ is an amino group plus the configuration at the carbon atom to which $R^{11}$ is attached is (S).

When $R^{11}$ is an amino group and a spiro ring composed of a methylene chain is present as a substituent, the configuration at the amino group is not precisely known. However, when $R^{11}$ is an amino group and there is no spiro ring composed of a methylene chain and is a spiro ring composed of a methylene chain having two carbon atoms, the preferred configuration has been confirmed to be (S).

Namely, in the case of the compound having a cyclic amino group having a spiro ring composed of a methylene chain having two carbon atoms, it is also confirmed that the preferable configuration at the carbon atom to which an amino group is attached is (S). However, the preferable configuration is still unknown in the case of a methylene chain having three carbon atoms.

With respect to the latter situation in the case of a compound represented by the formula

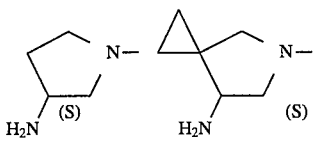

it is preferable that the configuration at the carbon atom to which the amino group is attached is (S), but in the case of a compound represented by the formula

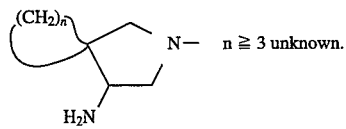

If either criterion on $R^{11}$ is met, then more preferred classes of compounds result when the following criteria are further met.

In the above situation where $R^{11}$ is an amino group, certain even more preferred classes of compounds result when the following limits (10) to (13) are met.

(10) where $R^5$ and $R^6$ form a methylene chain of 2 carbon atoms;

(11) where $R^5$ and $R^6$ form a methylene chain of 3 carbon atoms or

(12) where $X^2$ is a fluorine atom and $R^1$ is a hydrogen atom and A is C—$X^3$ where $X^3$ represents a hydrogen atom or a halogen atom or

(13) wherein $R^5$ and $R^6$ represent methyl groups.

When limit (12) is met, it is then preferred that $R^5$ and $R^6$ form a methylene chain of 2 or 3 carbon atoms, more preferred if such limits on $R^5$ and $R^6$ are met that $X^1$ be a fluorine atom and, if $X^1$ is a fluorine atom, most preferred that $X^3$ be chlorine.

When limit (13) is met, i.e., $R^5$ and $R^6$ are both methyl groups, then it is:

preferred $X^2$ be a fluorine atom, $R^1$ be a hydrogen atom, A be C—$X^3$ and $X^3$ be a hydrogen atom or halogen atom;

then more preferred that $X^1$ be a fluorine atom; and then most preferred that $X^3$ be a chlorine atom.

A separate preferred Set 5 exists for formula (I) and the isomer embodiment and the (S)/(R) acid embodiment.

Set 5 a=1, b=0, c=d=1, e=0, f=1; $R^3$, $R^4$, $R^7$, $R^8$, $R^9$ and $R^{10}$ represent hydrogen atoms, $R^5$ and $R^6$ form a 2 carbon atom methylene chain; Z represents >NR$^{12}$, and $R^{12}$ represents a hydrogen atom; $X^1$ and $X^2$ represent fluorine atoms; A represents C—$X^3$, and $X^3$ represents a hydrogen atom or a halogen atom.

Most highly preferred species within general formula (I), which are also, of course, preferably also within the isomer embodiment or the (S)/(R) acid embodiment are:

7-[7-amino-5-azaspiro[2.4]heptan-5-yl]-8-chloro-6-fluoro-1-(1,2-cis-2-fluorocyclopropyl)-4-oxo-1,4-dihydroquinoline-3-carboxylic acid or a pharmaceutically acceptable salt thereof;

7-[8-amino-6-azaspiro[3.4]octan-6-yl]-8-chloro-6-fluoro-1-(1,2-cis-2-fluorocyclopropyl)-4-oxo-1,4-dihydroquinoline-3-carboxylic acid or a pharmaceutically acceptable salt thereof; and 7-[4-amino-3,3-dimethyl-1-pyrrolidinyl]-8-chloro-6-fluoro-1-(1,2-cis-2-fluorocyclopropyl)-4-oxo-1,4-dihydroquinoline-3-carboxylic acid or a pharmaceutically acceptable salt thereof.

The present invention is especially directed to an antibacterial agent comprising a therapeutically effective amount of, as an active ingredient, at least one $N_1$-(1,2-cis-2-halogenocyclopropyl)-substituted pyridone-carboxylic acid derivative represented by formula (I) or a pharmaceutically acceptable salt thereof in combination with a pharmaceutically acceptable carrier, where the pharmaceutically acceptable salt is most preferably the hydrochloride, sulfate, phosphate, acetate, methanesulfonate, benzenesulfonate, p-toluenesulfonate, citrate, maleate, fumerate or lactate, and to a method for treating bacterial infections which comprises administering a therapeutically effective amount of $N_1$-(1,2-cis-2-halogenocyclopropyl)-substituted pyridonecarboxylic acid represented by the formula (I) or a pharmaceutically acceptable salt thereof.

For treating bacterial infections by administering a therapeutically effective amount thereof, or a therapeutically effective amount of a pharmaceutically acceptable salt thereof, the following are most highly preferred species as anti-bacterial agents:

7-[7-amino-5-azaspiro[2.4]heptan-5-yl]-8-chloro-6-fluoro-1-[2-(S)-2-fluoro-1-(R)-cyclopropyl]-4-oxo-1,4-dihydroquinoline-3-carboxylic acid;

7-[8-amino-6-azaspiro[3.4]octan-6-yl]-8-chloro-6-fluoro-1-[2-(S)-2-fluoro-1-(R)-cyclopropyl]-4-oxo-1,4-dihydroquinoline-3-carboxylic acid; and 7-[4-amino-3,3-dimethyl-1-pyrrolidinyl]-8-chloro-6-fluoro-1-[2-(S)-2-fluoro-1-(R)-cyclopropyl]-4-oxo-1,4-dihydroquinoline-3-carboxylic acid;

Formulation Examples are given below for illustrative purposes only but not for limitation.

FORMULATION EXAMPLE 1

Capsule:

| | |
|---|---|
| Compound of Example 8 | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | total: 150.0 mg |

FORMULATION EXAMPLE 2

Solution:

| | |
|---|---|
| Compound of Example 7 | 1 to 10 g |
| Acetic acid or sodium hydroxide | 0.5 to 2 g |
| Ethyl p-hydroxybenzoate | 0.1 g |
| Purified water | 88.9 to 98.4 g |
| | total: 100 g |

FORMULATION EXAMPLE 3

Powder for Admixture with Feedstuff:

| | |
|---|---|
| Compound of Example 6 | 1 to 10 g |
| Corn starch | 98.5 to 98.5 g |
| Light anhydrous silicic acid | 0.5 g |
| | total: 100 g |

The present invention is now illustrated in greater detail by way of the following Examples and Reference Examples, but it should be understood that the present invention is not deemed to be limited thereto. Reference Examples describe the syntheses of optically active skeletons from an optically active cis-2-fluorocyclopropanecarboxylic acid.

Antimicrobial activity of the optically active compounds prepared in Examples was evaluated in accordance with the standard method specified by Nippon Kagakuryoho gakkai, and results obtained are shown in Table 1 which precedes the claims herein in terms of minimum inhibitory concentration (MIC: µg/m$^2$).

Reference Example 1

N-[1-(R)-Phenylethyl]-1,2-cis-2-fluorocyclopropanecarboxamide (2a, 2b):

1-1. Carbonyldiimidazole Method:

One gram of cis-2-fluorocyclopropanecarboxylic acid was dissolved in 30 ml of tetrahydrofuran (THF), and 1.78 g of N,N'-carbonyldiimidazole was added thereto, and the mixture was stirred at room temperature for 1 hour. To the solution was added 1.45 g of (R)-(+)-α-methylbenzylamine, and the stirring was continued for 2 hours. The solvent was removed under reduced pressure, and the residue was extracted with chloroform. The extract was washed successively with a 10% citric acid aqueous solution and water and dried over anhydrous sodium sulfate. The solvent was removed under reduced pressure. From the residual viscous oily substance, each stereoisomer was isolated by HPLC under conditions shown below. Each isomer was recrystallized from diisopropyl ether to yield the titled compound (2a) or (2b).

HPLC Conditions:

Column: Nucleosil 50-5 (20 mm ID×250 mm L) (senshu Pack SSC Silica, 782-IN, produced by Senshu Kagaku)

Solvent: ethyl acetate-THF (9:1 by volume)

Flow Rate: 9.0 ml/min

Retention Time: 11 mins. for Compound (2a) 13 mins. for Compound (2b)

Compound (2a):

Melting point: 108° C.

Elementary Analysis for $C_{12}H_{14}FNO$: Calcd. (%): C 69.55; H 6.81; N 6.76 Found (%): C 69.31; H 7.01; N 6.65

$[\alpha]_D$: +61.96° (c=0.965, chloroform)

$^1$H-NMR (CDCl$_3$) δ ppm: 0.92–1.34 (2H, m), 1.50 (3H, d, J=7 Hz), 1.50–1.96 (1H, m), 4.68 (1H, dm, J=64 Hz), 5.14 (1H, m), 7.40 (5H, s)

Physiochemical Properties of compound (2b):

Melting point: 102° C.

Elementary Analysis for $C_{12}H_{14}FNO$: Calcd. (%): C 69.55; H 6.81; N 6.76 Found (%): C 69.45; H 6.87; N 6.70

$[\alpha]_D$: +143.61° (c=0.830, chloroform)

$^1$H-NMR (CDCl$_3$) δ ppm: 0.98=1.34 (2H, m), 1.52 (3H, d, J=7 Hz), 1.64–1.96 (1H, m), 4.58 (1H, dm, J=66 Hz), 5.24 (1H, m), 7.40 (5H, m)

1-2. Mixed Anhydride Method:

In 50 ml of THF were dissolved 4.19 g of 2-fluorocyclopropanecarboxylic acid (cis-trans mixture) and 4.07 g of triethylamine, and the solution was cooled to –10° C. To this was added a solution of 4.73 g of ethyl chloroformate in 20 ml of THF and the mixture was stirred for 10 minutes. To the solution was then added dropwise a solution of 4.88 g of (R)-(+)-α-methylbenzylamine in 30 ml of THF at that temperature, and the mixture was stirred at room temperature for 15 hours. The solvent was removed under reduced pressure, and the residue was extracted with benzene. The extract was washed successively with a 10% citric acid aqueous water and dried over anhydrous sodium sulfate. The solvent was removed under reduced pressure, and the resulting pale yellow oily substance was purified by silica gel column chromatography using a mixed solvent of benzene end ethyl acetate as an eluent to each of the titled compounds (2a) and (2b).

Reference Example 2

(+)-cis-2-Fluorocyclopropanecarboxylic acid (3a):

In 15 ml of concentrated hydrochloric acid was dissolved 530 mg of the amide compound (2a) as prepared in Reference Example 1, and the solution was heated at 100° to 110° C. for 5 hours while stirring. To the reaction mixture was added 20 ml of water, and the mixture was extracted with ethyl acetate. The extract was then extracted with a sodium hydrogencarbonate aqueous solution and this aqueous extract was washed with ethyl acetate. The aqueous extract was adjusted to a pH of 5 with concentrated hydrochloric acid and extracted with ethyl acetate. The extract was dried over anhydrous sodium sulfate, and the solvent was removed under reduced pressure to yield the titled compound (3a) as a pale yellow oil.

$[\alpha]_D$: –23.13° (c=1.020, chloroform)

$^1$H-NMR (CDCl$_3$) δ ppm: 1.0–1.42 (1H, m), 1.60–2.10 (2H, m), 4.82 (1H, dm, J=65 Hz), 12.0 (1H, s)

Reference Example 3

(+)-cis-2-Fluorocyclopropanecarboxylic acid (3b):

In 30 ml of concentrated hydrochloric acid was dissolved 1.65 g of amide compound (2b) as prepared in Reference Example 1, and the solution was heated at 100° to 110° C.

for 5 hours while stirring. The pH of the reaction mixture was adjusted between 8 and 9 with sodium hydrogencarbonate and then washed with chloroform. The pH of aqueous layer was adjusted to 4 with concentrated hydrochloric acid and extracted with ethyl acetate. The extract was dried over anhydrous sodium sulfate, and the solvent was removed under reduced pressure to give the titled compound (3b) as a pale yellow oil.

$[\alpha]_D$: +21.56° (c=1.113, chloroform)
$^1$H-NMR (CDCl$_3$) δ ppm: 1.0–1.42 (1H, m), 1.56–1.98 (2H, m), 4.76 (1H, dm, J=66 Hz), 11.32 (1H, s)

Reference Example 4

(+)-cis-1-(t-Butoxycarbonylamino)-2-fluorocyclopropane (4a):

In 5 ml of t-butanol were dissolved 200 mg of the carboxylic acid (3a) as obtained in Reference Example 2, 603 mg of diphenylphosphorylazide, and 203 mg of triethylamine, and the solution was heated under reflux for 4.5 hours. After removing the solvent under reduced pressure, the residue was extracted with chloroform. The extract was washed successively with a 10% citric acid aqueous solution, a 2% sodium hydroxide aqueous solution and water, and dried over anhydrous sodium sulfate. The solvent was removed under reduced pressure, and the residue was subjected to silica gel column chromatography using chloroform as an eluent to obtain the titled compound (4a) as a colorless crystal.

Melting Point: 73° C.
$[\alpha]_D$: +65.57° (c=0.610, chloroform)
$^1$H-NMR (CDCl$_3$) δ ppm: 0.6–1.3 (2H, m), 1.46 (9H, s), 2.48–2.74 (1H, m), 4.62 (1H, dm, J=65 Hz), 4.6–5.1 (1H, broad)

Reference Example 5

(−)-cis-1-(t-Butoxycarbonylamino)-2-fluorocyclopropane (4b):

In 6 ml of t-butanol were added 265 mg of the carboxylic acid (3b) as obtained in Reference Example 3, 800 mg of diphenylphosphorylazide, and 270 mg of triethylamine. The solution was allowed to react and worked up in the same manner as in Reference Example 4 to obtain the titled compound (4b).

Melting Point: 63° C.
$[\alpha]_D$: −60.27 (c=0.740, chloroform)
$^1$H-NMR (CDCl$_3$) δ ppm: 0.66–1.3 (2H, m), 1.46 (9H, s), 2.48–2.74 (1H, m), 4.58 (1H, dm, J=65 Hz), 4.6–5.1 (1H, broad)

Reference Example 6

(−)-Ethyl-2-[(1,2-cis-2-fluorocyclopropan-1-yl) aminomethylene]-3-oxo-3- (2,4,5-trifluorophenyl)propionate (5a):

Ethyl 2,4,5-trifluorobenzoylacetate (234 mg), 2 ml of ethyl orthoformate, and 4 ml of acetic anhydride were mixed and the mixture was heated at 110° to 120° C. for 2 hours while stirring. The solvent was removed under reduced pressure, and the residue was dissolved in 10 ml of dichloromethane.

Compound (4a) as obtained in Reference Example 4 (167 mg) and 5 ml of trifluoroacetic acid were mixed and the mixture was stirred at room temperature for 20 minutes and concentrated to dryness under reduced pressure (the resulting amine trifluoroacetate was used without purification). The residue was dissolved in 10 ml of dichloromethane and cooled to −10° C. A solution of 230 mg of triethylamine in 10 ml of dichloromethane was added dropwise thereto. Thereafter, the above prepared dichloromethane solution was added dropwise to the mixture, followed by stirring at room temperature over-night. The solvent was evaporated to dryness under reduced pressure, and the residue was subjected to silica gel column chromatography using a mixed solvent of benzene and ethyl acetate (2:1 by volume). A yellow oily substance was obtained from the eluent after the removed of the solvent. The product was recrystallized from diisopropyl ether-n-hexane to yield the titled compound (5a) as a colorless crystals.

Melting Point: 69°–70° C.
$[\alpha]_D$: 10.29° (c=1.088, chloroform)

Reference Example 7

(+)-Ethyl-2-[(1,2-cis-2-fluorocyclopropan-1-yl) aminomethylene]-3-oxo- 3-(2,4,5-trifluorophenyl)propionate (5b):

Ethyl 2,4,5-trifluorobenzoylacetate (337 mg), 2 ml of ethyl orthoformate, and 4 ml of acetic anhydride were mixed, and the mixture was heated at 110° to 120° C. for 2 hours while stirring. The solvent was removed under reduced pressure, and the residue was dissolved in 10 ml of dichloromethane.

Compound (4b) as obtained in reference Example 5 (240 mg) and 5 ml of trifluoroacetic acid were mixed an the mixture was stirred at room temperature for 1 hour followed by concentration under reduced pressure (the amine trifluoroacetate was used without purification) The residue was dissolved in 10 ml of dichloroethane, and the solution was cooled to −10° C. A solution of 230 mg of triethylamine in 10 ml of dichloromethane was added thereto dropwise, and the above-prepared dichloromethane solution was further added to the mixture, followed by stirring at room temperature over-night. The solvent was removed under reduced pressure, and the residue was subjected to silica gel column chromatography using a mixed solvent of benzene and ethyl acetate (2:1 by volume). A yellow oily substance was obtained from the eluent after the removal of solvent. Recrystallization from diisopropyl ether-n-hexane gave the titled compound (5b) as a colorless crystal.

Melting Point: 69°–70° C.
$[\alpha]_D$: +12.09 (c=0.645, chloroform)

Reference Example 8

(+)-6,7-Difluoro-1-(1,2-cis-2-fluorocyclopropyl)- 4-oxo-1,4-dihydroquinoline-3-carboxylate (6a):

In 15 ml of anhydrous dioxane was dissolved 180 mg of Compound (5a) as obtained in Reference Example 6, and 200 mg of 60% sodium hydride was added to the solution, followed by stirring at room temperature for 2 days. The reaction mixture was added to a 10% citric acid aqueous solution, followed by concentration under reduced pressure. The residue was extracted with chloroform, and the extract was dried over anhydrous sodium sulfate. The solvent was removed under reduced pressure. The residue was purified by silica gel preparative TLC using benzene-ethyl acetate (1:2 by volume) as a developing solvent to yield the titled compound (6a) as a colorless crystal.

Melting Point: 231°–232° C.

[α]$_D$: +27.20° (c=0.610, chloroform)

$^1$H-NMR (CDCl$_3$) δ ppm: 1.20 (3H, t, J=7 Hz), 1.6–1.9 (2H, m), 3.28–3.56 (1H, m), 4.42 (2H, q, J=7 Hz), 5.11 (1H, dm, J=63 Hz), 7.60 (1H, dd, J=11 Hz & 7 Hz), 8.28 (1H, dd, J=10 Hz & 11 Hz), 8.58 (1H, s)

Reference Example 9

(−)-Ethyl 6,7-difluoro-1-(1,2-cis-2-fluorocyclopropyl)-4-oxo-1,4-dihydroquinoline- 3-carboxylate (6b):

In 15 ml of anhydrous dioxane was dissolved 267 mg of Compound (5b) as obtained in Reference Example 7, and 200 mg of 60% sodium hydride was added thereto, and the mixture was stirred at room temperature for 2 days. The reaction mixture was added to a 10% citric acid aqueous solution, followed by concentration under reduced pressure. The residue was extracted with chloroform and dried over anhydrous sodium sulfate. The solvent was removed under reduced pressure, and the residue was purified by silica gel preparative TLC using benzene-ethyl acetate (1:2 by volume) as a developing solvent to yield the titled compound (6b) as a colorless crystal.

Melting Point: 226°–227° C.

[α]$_D$: −31.36° (c=0.610, chloroform)

$^1$H-NMR (CDCl$_3$) δ ppm: 1.22 (3H, t, J=7 Hz), 1.5–1.9 (2H, m), 3.26–3.52 (1H, m), 4.40 (2H, q, J=7 Hz), 5.10 (1H, dm, J=63 Hz), 7.58 (1H, dd, J=11 Hz & 7 Hz), 8.26 (1H, dd, J=10 Hz & 11 Hz), 8.55 (1H, s)

Reference Example 10

(+)-6,7-Difluoro-1-(1,2-cis-2-fluorocyclopropyl)-4-oxo-1,4-dihydroquinoline- 3-carboxylic acid (7a):

In 15 ml of concentrated hydrochloric acid was dissolved 106 mg of the ester (6a) as obtained in Reference Example 8, and the solution was heated at 100° to 110° C. for 2 hours while stirring. To the reaction mixture was added 15 ml of water, and the precipitate was collected by filtration to obtain the titled compound (7a) as a colorless crystal.

Melting Point: 265°–270° C.

[α]$_D$: +3.66° (c=0.383, acetic acid)

$^1$H-NMR (CDCl$_3$) δ ppm: 1.75–1.95 (2H, m), 3.58 (1H, m), 5.18 (1H, dm, J=64 Hz), 7.82 (1H, dd, J=12 Hz, & 7 Hz), 8.37 (1H, dd, J=18 Hz & 8 Hz), 8.94 (1H, s)

Reference Example 11

(−)-6,7-Difluoro-1-(1,2-cis-2-fluorocyclopropyl)-4-oxo-1,4-dihdryoquinoline-3-carboxylic acid (7b):

In 10 ml of concentrated hydrochloric acid was dissolved 150 mg of the ester (6b) as obtained in Reference Example 9, and the solution was heated at 110° C. for 2 hours while stirring. To the reaction mixture was added 20 ml of water, and the mixture was extracted with chloroform. The extract was dried over anhydrous sodium sulfate, and the solvent was removed under reduced pressure. The residue was recrystallized from ethanol to yield the titled compound (7b) as a colorless crystal.

Melting Point: 261°–264° C.

[α]$_D$: −4.08° (c=0.343, acetic acid)

$^1$H-NMR (CDCl$_3$) δ ppm: 1.75–1.95 (2H, m), 3.58 (1H, m), 5.18 (1H, dm, J=64 Hz), 7.82 (1H, dd, J=12 Hz & 7 Hz), 8.37 (1H, dd, J=12 Hz & 8 Hz ), 8.94 (1H s)

EXAMPLE 1

7-[3-(S)-t-Butoxycarbonylamino-1-pyrrolidinyl]-6-fluoro-1-(1,2-cis-2-fluorocyclopropyl)-4-oxo-1,4-dihydroquinoline-3-carboxylic acid (8a):

Seventy milligrams of the carboxylic acid (7a) as obtained in Reference Example 10, 150 mg of (S)-3-(t-butoxycarbonylamino)pyrrolidine, 200 mg of triethylamine, and 20 ml of acetonitrile were mixed, and the mixture was heated under reflux for 4 hours. The solvent was removed under reduced pressure, and to the residue was added a 10% citric acid aqueous solution, followed by extraction with chloroform. The extract was dried over anhydrous sodium sulfate, and the solvent was removed under reduced pressure. The residue was recrystallized from ethyl acetate to obtain the titled compound (8a) as a yellow crystal.

Melting Point: 236°–239° C.

[α]$_D$: +1.0° (c=0.200, chloroform)

$^1$H-NMR (CDCl$_3$) δ ppm: 1.2–1.7 (2H, m), 1.46 (9H, s), 1.7–1.9 (1H, m), 2.0–2.36 (1H, m), 3.3–4.0 (5H, m), 4.2–4.4 (1H, m), 5.06 (1H, dm, J=68 Hz), 6.68 (1H, d, J=7 Hz), 7.84 (1H, d, J=14 Hz), 8.46 (1H, s)

EXAMPLE 2

7-[3-(S)-t-Butoxycarbonylamino-1-pyrrolidinyl]-6-fluoro-1-(1,2-cis-2-fluorocyclopropyl)-4-oxo-1,4-dihydroquinolone-3-carboxylic acid (8b):

The carboxylic acid as obtained in Reference Example 11 (7b) (112 mg), 200 mg of (S)-3-(t-butoxycarboxylamino)pyrrolidine, 220 mg of triethylamine, and 15 ml of acetonitrile were mixed, and the mixture was heated under reflux for 4 hours. The solvent was removed under reduced pressure, and to the residue was added a 10% citric acid aqueous solution, followed by extraction with chloroform. The extract was dried over anhydrous sodium sulfate, and the solvent was removed under reduced pressure. The residue was recrystallized from ethyl acetate to yield the titled compound (8b) as a yellow crystal.

Melting Point: 242°–243° C.

[α]$_D$: −4.0° (c=0.448, chloroform)

$^1$H-NMR (CDCl$_3$) δ ppm: 1.0–1.7 (2H, m), 1.40 (9H, s), 1.6–1.8 (1H, m), 1.9–2.1 (1H, m), 3.3–3.9 (5H, m), 4.2–4.5 (1H, m), 5.00 (1H, dm, J=68 Hz), 6.58 (1H, d, J=7 Hz), 7.72 (1H, d, J=14 Hz), 8.32 (1H, s)

EXAMPLE 3

7-[3-(S)-Amino-1-pyrrolidinyl]-6-fluoro-1-(1,2-cis-2-fluorocyclopropyl)-4-oxo-1,4-dihydroquinoline-3-carboxylic acid (9a):

In 10 ml of trifluoroacetic acid was dissolved 80 mg of the carboxylic acid (8a) as obtained in Example 1. After stirring for 20 minutes, the reaction mixture was evaporated under reduced pressure to dryness. To the residue was added 5 ml of water, and was further added a 1N sodium hydroxide aqueous solution to dissolve the residue. The pH of aqueous layer was adjusted to 7.5 with 1N hydrochloric acid, followed by extraction with chloroform. The extract was dried over anhydrous sodium sulfate, and the solvent was removed under reduced pressure. Recrystallization of the residue from ethanol yielded the titled compound as a colorless crystal.

Melting Point: 248°–252° C.

$[\alpha]_D$: –31.35° (c=0.370, 1N NaOH aqueous solution)

$^1$H-NMR (CDCl$_3$) δ ppm: 1.52–1.68 (2H, m), 1.68–1.80 (1H, m), 2.05–2.15 (1H, m), 3.13–3.22 (1H, m), 3.25–3.45 (2H, m), 3.45–3.65 (3H, m), 5.12 (1H, dm, J=65 Hz), 6.58 (1H, d, J=7 Hz), 7.58 (1H, d, J=14 Hz), 8.29 (1H, s)

EXAMPLE 4

7-[3-(S)-Amino-1-pyrrolidinyl]-6-fluoro-1-(1,2-cis-2-fluorocyclopropyl)-4-oxo-1,4-dihydroquinoline-3-carboxylic acid (9a:

In 10 ml of trifluoroacetic acid was added 80 mg of the carboxylic acid (8b) as obtained in Example 2. After stirring for 20 minutes, the reaction mixture was evaporated to dryness under reduced pressure. To the residue was added 5 ml of water, and was further added a 1N sodium hydroxide aqueous solution to dissolve the residue. The pH of aqueous layer was adjusted to 7.5 with 1N hydrochloric acid and followed by extraction with chloroform. The extract was dried over anhydrous sodium sulfate, and the solvent was removed therefrom under reduced pressure. Recrystallization of the residue from ethanol gave the titled compound (9b) as a colorless crystal.

Melting Point: 236°–240° C.

$[\alpha]_D$: +23.72 (c=0.413, 1N NaOH aqueous solution)

$^1$H-NMR (CDCl$_3$) δ ppm: 1.55–1.69 (2H, m), 1.69–1.77 (1H, m), 2.07–2.15 (1H, m), 3.15–3.22 (1H, m), 3.37–3.47 (2H, m), 3.52–3.58 (2H, m), 3.58–3.66 (1H, m), 5.13 (1H, dm, J=65 Hz), 6.62 (1H, d, J=7 Hz), 7.61 (1H, d, J=14 Hz), 8.30 (1H, s)

Reference Example 12

(–)-Ethyl 2-[[1,2-cis-2-fluoro-1-cyclopropyl)amino]-methylene]-3-oxo-3-(3-chloro-2,4,5-trifluorophenyl)propionate (10a):

Ethyl 3-chloro-2,4,5-trifluorobenzoylacetate (1.5 g), 6 ml of ethyl orthoformate, and 10 ml of acetic anhydride were mixed, and the mixture was heated at 110° to 120° C. for 1.5 hours while stirring. The reaction mixture was concentrated to dryness under reduced pressure, and the residue was dissolved in 5 ml of dichloromethane.

Seven milliliters of trifluoroacetic acid was cooled with ice, and 480 mg of (+)-cis-1-(t-butoxycarbonylamino)-2-fluorocyclopropane (4a) was dissolved therein. The solution was stirred at room temperature for 20 minutes, followed by evaporation under reduced pressure to dryness. The residue was suspended in 10 ml of dichloromethane, and 3 ml of triethylamine was added thereto under ice-cooling. After stirring for 20 minutes, the above-prepared dichloromethane solution was added thereto, and the mixture was stirred for 1 hour. The reaction mixture was washed with water and dried over anhydrous sodium sulfate. The solvent was removed under reduced pressure. The residue was subjected to flash column chromatography using a mixed solvent of benzene and ethyl acetate (5:1 by volume) as an eluent. The solvent was removed under reduced pressure, and the residue was washed with diisopropyl ether to obtain 620 mg of the titled compound (10a).

Melting Point: 98°–100° C.

$[\alpha]_D$: –6.66° (c=0.998, chloroform)

Elementary Analysis for C$_{15}$H$_{12}$ClF$_4$NO$_3$: Calcd. (%): C 49.26; H 3.31; N 3.83 Found (%): C 49.39; H 3.22; N 3.86

$^1$-NMR (CDCl$_3$) δ ppm: 0.95, 1.08 (3H, 1:2.5, each t, J=7 HZ), 1.0–1.5 (2H, m), 2.8–3.15 (1H, m), 4.03, 4.07 (2H, 1:2.5, each q, J=7 Hz), 4.78 (1H, dm, J=65 Hz), 7.13 (1H, ddd, J=5.9, 8.6, & 9.5 Hz), 8.20, 8.25 (1H, 1:2.5, each d, J=14 HZ)

Reference Example 13

(+)-2-[[1,2-cis-2-Fluoro-1-cyclopropyl)amino]methylene]-3-oxo-3-(3-chloro-2,4,5-trifluorophenyl)propionate (10b):

Ethyl 3-chloro-2,4,5-trifluorobenzoylacetate (1.5 g), 6 ml of ethyl orthoformate, and 10 ml of acetic anhydride were mixed, and the mixture was heated at 110° to 120° C. for 1.5 hours while stirring. The reaction mixture was concentrated to dryness under reduced pressure, and the residue was dissolved in 10 ml of dichloromethane.

Ten milliliters of trifluoroacetic acid were ice-cooled, and 1.12 g of (–)-cis-1-(t-butoxycarbonylamino)-2-fluorocyclopropane (4b) was dissolved therein. After stirring at room temperature for 20 minutes, the mixture was evaporated to dryness under reduced pressure. The residue was suspended in 20 ml of dichloromethane, and 2.0 g of triethylamine was added to the suspension under ice-cooling. The above-prepared dichloromethane solution was then added thereto, followed by stirring for 1 hour. The reaction mixture was washed with water and dried over anhydrous sodium sulfate. The solvent was removed under reduced pressure. The residue was subjected to flash column chromatography which was eluted with a mixed solvent of benzene and ethyl acetate (4:1 by volume) The solvent of the eluent was removed under reduced pressure. The residue was washed with diisopropyl ether-n-hexane to obtain 1.74 g of crystals of the titled compound (10b).

Melting Point: 99°–100° C.

$[\alpha]_D$: +6.70° (c=0.895, chloroform)

Elementary Analysis for C$_{15}$H$_{12}$ClF$_4$NO$_3$: Calcd. (%): C 49.26; H 3.31; N 3.83 Found (%): C 49.41; H 3.60; N 4.06

$^1$H-NMR (CDCl$_3$) δ ppm: 0.95, 1.08 (3H, 1:2.5, each t, J=7 HZ), 1.0–1.5 (2H, m), 2.8–3.15 (1H, m), 4.03, 4.07 (2H, 1:2.5, each q, J=7 Hz), 4.78 (1H, dm, J=65 Hz), 7.13 (1H, ddd, J=5.9, 8.6, & 9.5 Hz), 8.20, 8.25 (1H, 1:2.5, each d, J=14 HZ)

Reference Example 14

(+)-Ethyl 8-chloro-6,7-difluoro-1-(1,2-cis-2-fluoro-1-cyclopropyl)-4-oxo-1,4-dihydroquinoline-3-carboxylate (11a):

In 7 ml of anhydrous dioxane was dissolved 620 mg of Compound (10a) as prepared in Reference Example 12, and 80 mg of 60% sodium hydride was added to the solution, followed by stirring at room temperature for 1 hour. Ethyl acetate was added to the reaction mixture, and the mixture was washed successively with a 10% citric acid aqueous solution and water. The organic layer was dried over anhydrous sodium sulfate, and the solvent was removed therefrom under reduced pressure. The residue was washed with n-hexane to obtain 551 mg of the titled compound (11a) as a colorless crystal.

Melting Point: 181°–184° C.

$[\alpha]_D$: +45.1° (c=1.18, chloroform)

Elementary Analysis for $C_{15}H_{12}ClF_4NO_3$: Calcd. (%): C 52.12; H 3.21; N 4.05 Found (%): C 52.09; H 3.33; N 4.01

$^1$H-NMR (CDCl$_3$) δ ppm: 1.40 (3H, t, J=7 HZ), 1.4–1.9 (2H, m), 4.08 (1H, m), 4.39 (2H, q, J=7 HZ), 4.90 (1H, dm, J=65 Hz), 8.24 (1H, dd, J=10 & 11 Hz)

Reference Example 15

(–)-Ethyl 8-chloro-6,7-difluoro-1-(1,2-cis-2-fluoro-1-cyclopropyl)-4-oxo-1,4-dihydroquinoline-3-carboxylate (11b):

In 10 ml of anhydrous dioxane was suspended 560 mg of 60% sodium hydride having been washed twice with anhydrous n-hexane. The suspension was added to a solution of 1.70 g of Compound (10b) in 20 ml of anhydrous dioxane, followed by stirring at room temperature for 2 hours. The solvent was removed under reduced pressure, and 0.1N hydrochloric acid was added to the residue. The precipitated crystals were collected by filtration, washed successively with water and diethyl ether, and dried under reduced pressure to obtain 1.44 g of the entitled compound (11b) as a colorless crystal.

X-ray analysis of the compound obtained in this Reference Example established that the absolute configuration around the asymmetric carbon of the N$_1$-substituent of the compound obtained in this Reference Example was 2-(S) and 1-(R). Thus, the titled compound is correctly named (–)-ethyl 8-chloro-6,7-difluoro-1-[2-(S)-fluoro-1-(R)-cyclopropyl]-4-oxo-1,4-dihydroquinoline-3-carboxylate.

Melting Point: 174° C.

$[\alpha]_D$: –45.3° (c=1.05, chloroform)

Elementary Analysis for $C_{15}H_{11}ClF_4NO_3$: Calcd. (%): C 52.12; H 3.21; N 4.05 Found (%): C 51.80; H 3.45; N 4.15

$^1$H-NMR (CDCl$_3$) δ ppm: 1.40 (3H, t, J=7 HZ), 1.4–1.9 (2H, m), 4.08 (1H, m), 4.39 (2H, q, J=7 HZ), 4.90 (1H, dm, J=65 Hz), 8.24 (1H, dd, J=10 & 11 Hz)

IR(KRr); $v_{max}$ cm$^{-1}$: 3100, 2998, 1731, 1638, 1614, 1470, 1317

Reference Example 16

(+)-8-chloro-6,7-difluoro-1-(1,2-cis-2-fluoro-1-cyclopropyl)-4-oxo-1,4-dihydorquinoline-3-carboxylic acid (12a):

The ester (11a) (540 mg), 5 ml of concentrated hydrochloric acid, and 5 ml of acetic acid were mixed, and the mixture was heated at 120°–130° C. for 2 hours while stirring. To the reaction mixture was added 50 ml of water, and the precipitated crystals were collected by filtration, washed successively with water and diethyl ether, and dried under reduced pressure to obtain 420 mg of the titled compound (12a) as a colorless crystal.

Melting Point: 170°–171° C.

$[\alpha]_D$: +30.4° (c=0.54, chloroform)

Elementary Analysis for $C_{13}H_7ClF_3NO_3$: Calcd. (%): C 49.16; H 2.22; N 4.41 Found (%): C 49.21; H 2.49; N 4.27

$^1$H-NMR (CDCl$_3$) δ ppm: 1.3–2.0 (2H, m), 4.12–4.34 (1H, m), 4.95 (1H, dm, J=63 Hz), 8.27 (1H, dd, J=8 & 8 Hz), 8.87, 8.89 (1H, each s, split 1:1)

Reference Example 17

(–)-8-Chloro-6,7-difluoro-1-(1,2-cis-2-fluoro-1-cyclopropyl)-4-oxo-1,4-dihydroquinoline-3-carboxylic acid (12b)

The ester (11b) (1.40 g) and 10 ml of concentrated hydrochloric acid were mixed and the mixture was heated at 110° C. for 2.5 hours under stirring. To the reaction mixture was added 50 ml of water, and the precipitated crystals were collected by filtration, washed with water and diethyl ether, and dried under reduced pressure to obtain 1.16 g of the titled compound (12b) as a colorless crystal.

Melting Point: 177°–182° C.

$[\alpha]_D$: –26.8° (c=0.90, chloroform)

Elementary Analysis for $C_{13}H_7ClF_3NO_3$: Calcd. (%): C 49.16; H 2.22; N 4.41 Found (%): C 49.28; H 2.40; N 4.66

$^1$H-NMR (CDCl$_3$) δ ppm: 1.3–2.0 (2H, m), 4.12–4.34 (1H, m), 4.95 (1H, dm, J=63 Hz), 8.27 (1H, dd, J=8 & 8 Hz), 8.87, 8.89 ( 1H, each s, split 1:1)

EXAMPLE 5

(+)-7-[3-(S)-Amino-1-pyrrolidinyl]-8-chloro-6-fluoro-1-(1,2-cis-2-fluoro-1-cyclopropyl)-4-oxo-1,4-dihydroquinoline-3-carboxylic acid (13a):

Five milliliters of trifluoroacetic acid was cooled with ice, and 230 mg of 3-(S)-1-t-butoxycarbonyl-3-(t-butoxycarbonylamino)pyrrolidine was dissolved therein, followed by stirring at room temperature for 20 minutes. The reaction mixture was evaporated to dryness under reduced pressure, and the residue was dissolved in 15 ml of acetonitrile. To the solution were added 170 mg of the carboxylic acid (12a) and 400 mg of triethylamine, followed by refluxing for 6.5 hours. The reaction mixture was evaporated to dryness under reduced pressure, and to the residue was added 1N hydrochloric acid. The mixture was washed with chloroform. The pH of the aqueous layer was adjusted to 12 with a 1N sodium hydroxide aqueous solution and washed with chloroform. The pH of the aqueous layer was readjusted to 7.6 with hydrochloric acid and extracted with chloroform. The extract was dried over anhydrous sodium sulfate, and the solvent was evaporated. The residue was recrystallized from aqueous ammonia-ethanol to obtain 138 mg of the titled compound (13a) as a colorless crystal.

Melting Point: 214°–217° C. (with decomposition)

$[\alpha]_D$: +120.8° (c=0.475, 0.1N NaOH aqueous solution)

Elementary Analysis for $C_{17}H_{16}ClF_2N_3O_3 \cdot \frac{1}{2}H_2O$: Calcd. (%): C 51.98; H 4.36; N 10.70 Found (%): C 52.07; H 4.71; N 10.72

$^1$H-NMR (NaOD) δ ppm: 1.28 (1H, dm, J=27 Hz), 1.69–1.78 (2H, m), 3.39–3.42 (1H, m), 3.51–3.61 (3H, m), 3.69–3.72 (1H, m), 4.13–4.17 (1H, m), 4.99 (1H, dm, J=70 Hz), 7.72 (1H, d, J=14 Hz), 8.44, 8.45 (1H, each s, split, 1:1)

EXAMPLE 6

(–)-7-[3-(S)-Amino-1-pyrrolidinyl]-8-chloro-6-fluoro-1-(1,2-cis-2-fluoro-1-cyclopropyl)-4-oxo-1,4-dihydroquinoline-3-carboxylic acid (13a):

Five milliliters of trifluoroacetic acid was cooled with ice, and 230 mg of 3-(S)-t-butoxycarbonyl-3-(t-butoxycarbonylamino)pyrrolidine was dissolved therein, followed by stirring at room temperature for 20 minutes. The reaction mixture was evaporated to dryness under reduced pressure, and the residue was dissolved in 15 ml of acetonitrile. To the solution were added 170 mg of the carboxylic acid (12b) add 400 mg of triethylamine, and the mixture was heated under reflux for 6.5 hours. The reaction mixture was evaporated to dryness under reduced pressure. A 1N hydrochloric acid was added to the residue, and the mixture was washed with chloroform. The aqueous layer was adjusted to a pH of 12 with a 1N sodium hydroxide aqueous solution, and the aqueous layer was adjusted to a pH of 7.6 with hydrochloric acid and extracted with chloroform. The extract was dried over anhydrous sodium sulfate, and the solvent was evaporated. The residue was recrystallized from aqueous ammonia-ethanol to give 158 mg of the titled compound (13b) as a colorless crystal.

Melting Point: 247°–252° C. (with decomposition)

$[\alpha]_D$: −94.7° (c=0.378, 0.1N HaOH aqueous solution)

Elementary Analysis for $C_{17}H_{16}ClF_2N_3O_3 \cdot H_2O$: Calcd. (%): C 50.82; H 4.52; N 10.46 Found (%): C 50.97; H 5.14; N 10.42

$^1$H-NMR (NaOD) δ ppm: 1.32 (1H, dm, J=27 Hz), 1.73–1.80 (2H, m), 2.15–2.19 (1H, m), 3.19–3.22 (1H, m), 3.45–3.50 (1H, m), 3.58–3.62 (1H, m), 3.85–3.88 (2H, m), 4.16–4.20 (1H, m), 4.99 (1H, dm, J=63 Hz), 7.76 (1H, d, J=14 Hz), 8.54, 8.44 (1H, each s, split, 1:1)

Reference Example 18

(−)-Ethyl 2-[[(1,2-cis-2-fluoro-1-cyclopropyl)amino] methylene]-3-oxo-3-(2,3,4,5-tetrafluoro-6-nitrophenyl)-propionate (14a):

Ethyl 2,3,4,5-tetrafluoro-6-nitrobenzoylacetate (1.5 g), 6 ml of ethyl orthoformate, and 10 ml of acetic anhydride were mixed, and the mixture was heated at 120° C. for 2 hours. The reaction mixture was concentrated to dryness, and the residue was dissolved in 10 ml of dichloromethane.

Ten milliliters of trifluoroacetic acid was cooled with ice, and 1.1 g of (+)-cis-1-(t-butoxycarbonylamino)-2-fluorocyclopropane (4a) was dissolved therein. The solution was stirred at room temperature for 20 minutes, followed by evaporating to dryness under reduced pressure. The residue was suspended in 20 ml of dichloromethane, and 2.0 g of triethylamine was added thereto under ice-cooling, followed by stirring for 20 minutes. The above-prepared dichloromethane solution was then added thereto, followed by stirring for 30 minutes. The reaction mixture was washed with water and dried over anhydrous sodium sulfate. The solvent was removed under reduced pressure. The residue was subjected to flash column chromatography using benzene as an eluent. The fractions of the compound (14a) were combined, and the solvent was removed under reduced pressure. The residue was washed with n-hexane to yield 1.57 g of crystals of the titled compound (14a).

Melting Point: 99°–100° C.

$[\alpha]_D$: 10.3° (c=1.25, chloroform)

Elementary Analysis for $C_{15}H_{11}F_5N_2O_5$ Calcd. (%): C 45.70; H 2.81; N 7.10 Found (%): C 45.60; H 3.01; N 7.03

$^1$H-NMR (CDCl$_3$) δ ppm: 1.10 (3H, t, J=7 Hz), 1.2–1.55 (2H, m), 2.88–3.16 (1H, m), 4.09 (2H, q, J=7 Hz), 4.45 (1H, dm, J=63 Hz), 8.29 (1H, d, J=14 Hz)

IR(KBr): $\nu_{max}$ cm$^{-1}$: 3454 1734, 1626, 1566, 1521, 1482

Reference Example 19

(+)-Ethyl 2-[[(1,2-cis-2-fluoro-1-cyclopropyl)amino]-methylene]-3-oxo-3-(2,3,4,5-tetrafluoro-6-nitrophenyl)-propionate (14b):

Ethyl 2,3,4,5-tetrafluoro-6-nitrobenzoylacetate (1.5 g), 6 ml of ethyl orthoformate and 10 ml of acetic anhydride were mixed, and the mixture was heated at 110° to 120° C. for 1 hour while stirring. The reaction mixture was concentrated to dryness, and the residue was dissolved in 10 ml of dichloromethane.

Ten milliliters of trifluoroacetic acid was ice-cooled, and 1.10 g of (−)-cis-1-(t-butoxycarbonylamino)- 2-fluorocyclopropane (4b) was dissolved therein, followed by stirring at room temperature for 20 minutes. The reaction mixture was evaporated to dryness under reduced pressure, and the residue was suspended in 20 ml of dichloromethane. To the suspension was added 1.8 g of triethylamine under ice-cooling, followed by stirring for 20 minutes. To the mixture was added the above-prepared dichloromethane solution, followed by stirring for 2 hours. The reaction mixture was washed with water and dried over anhydrous sodium sulfate. The solvent was removed under reduced pressure, and the residue was subjected to flash column chromatography using benzene as an eluent. The fractions of the product (14b) were combined, and the solvent was removed under reduced pressure. The residue was washed with n-hexane to yield 1.50 g of crystals of the titled compound (14b).

Melting Point: 98°–100° C.

$[\alpha]_D$: −10.1° (c=2.09, chloroform)

Elementary Analysis for $C_{15}H_{11}F_5N_2O_5$ Calcd. (%): C 45.70; H 2.81; N 7.10 Found (%): C 45.77; H 3.38; N 7.18

$^1$H-NMR (CDCl$_3$) δ ppm: 1.10 (3H, t, J=7 Hz), 1.2–1.5 (2H, m), 2.88–3.12 (1H, m), 4.09 (2H, q, J=7 Hz), 4.45 (1H, dm, J=63 Hz), 8.30 (1H, d, J=14 Hz)

IR(KBr): $\nu_{max}$ cm$^{-1}$: 3454 1695, 1638, 1554, 1515

Reference Example 20

(+)-Ethyl 6,7,8-trifluoro-1-(1,2-cis-2-fluoro-1-cyclopropyl)-5-nitro-4-oxo-1,4-dihydroquinoline-3-carboxylate (15a):

In 20 ml of anhydrous dioxane was suspended 580 mg of 60% sodium hydride having been washed twice with n-hexane. The suspension was added to a solution of 1.90 g of Compound (14a) in 20 ml of anhydrous dioxane. The mixture was stirred at room temperature for 1 hour, and the solvent was removed from the reaction mixture under reduced pressure. To the residue was added 0.1N hydrochloric acid. The crystals thus formed were collected by filtration, washed successively with water and diethyl ether, and dried under reduced pressure to obtain 1.65 g of the titled compound (15a) as a colorless crystal.

Melting Point: 172°–176° C.

$[\alpha]_D$: +10.7° (c=1.12, chloroform)

Elementary Analysis for $C_{15}H_{10}F_4N_2O_5$ Calcd. (%): C 48.14; H 2.69; N 7.49 Found (%): C 48.29; H 2.78; N 7.20

$^1$H-NMR (CDCl$_3$) δ ppm: 1.36 (3H, t, J=7 Hz), 1.4–1.92 (2H, m), 3.80–4.08 (1H, m), 4.34 (2H, q, J=7 Hz), 4.99 (1H, dm, J=63 Hz), 8.55 (1H, s)

IR(KBr): $\nu_{max}$ cm$^{-1}$: 3454 1734, 1626, 1566, 1521 1482

Reference Example 21

(−)-Ethyl 6,7,8-trifluoro-1-(1,2-cis-2-fluoro-1-cyclopropyl)-5-nitro-4-oxo-1,4-dihydroquinoline-3-carboxylate (15b):

In 10 ml of anhydrous dioxane was suspended 440 mg of 60% sodium hydride having been washed twice with n-hexane. The suspension was added to a solution of 1.45 g of Compound (14b) in 20 ml of anhydrous dioxane, followed by stirring at room temperature for 30 minutes. The solvent was removed from the reaction mixture under reduced pressure. To the residue was added 0.1N hydrochloric acid, and the formed crystals were collected by filtration, washed successively with water and diethyl ether, and dried under reduced pressure to obtain 1.18 g of the titled compound (15b) as a colorless crystal.

Melting Point: 171°–175° C.

$[\alpha]_D$: 11.1° (c=0.27, chloroform)

Elementary Analysis for $C_{15}H_{10}F_4N_2O_5$ Calcd. (%): C 48.14; H 2.69; N 7.49 Found (%): C 48.44; H 3.17; N 7.48

$^1$H-NMR (CDCl$_3$) δ ppm: 1.36 (3H, t, J=7 Hz), 1.4–1.92 (2H, m), 3.74–4.02 (1H, m), 4.36 (2H, q, J=7 Hz), 4.94 (1H, dm, J=62 Hz), 8.54 (1H, s)

IR(KBr): $v_{max}$ cm$^{-1}$: 1731, 1626, 1566, 1485, 1323, 1275

Reference Example 22

(+)-Ethyl 5-amino-6,7,8-trifluoro-1-(1,2-cis-2-fluoro-1-cyclopropyl)-4-oxo-1,4-dihydroquinoline-3-carboxylic acid (16a):

The nitro compound (15a) (1.60 g), 6 ml of Raney nickel, and 200 ml of ethanol were mixed, and the mixture was shaken for 2.5 hours in a hydrogen atmosphere. The catalyst was removed by filtration through Celite, and the filtrate was concentrated under reduced pressure. The residue was subjected to silica gel column chromatography using chloroform as an eluent. The fractions of product (16a) were combined, and the solvent was removed therefrom under reduced pressure. The residue was recrystallized from ethanol to obtain 770 mg of the titled compound (16a) as a pale yellow crystal.

Melting Point: 190°–191° C.

$[\alpha]_D$: +26.0° (c=0.76, chloroform)

Elementary Analysis for $C_{15}H_{12}F_4N_2O_3$ Calcd. (%): C 52.33; H 3.51; N 8.14 Found (%): C 52.13; H 3.95; N 8.13

$^1$H-NMR (CDCl$_3$) δ ppm: 1.39 (3H, t, J=7 Hz), 1.4–1.8 (2H, m), 3.60–3.88 (1H, m), 4.38 (2H, q, J=7 Hz), 4.87 (1H, dm, J=63 Hz), 6.8–7.1 (2H, m), 8.37 (1H, s)

IR(KBr): $v_{max}$ cm$^{-1}$: 3436, 1683, 1653, 1557, 1461, 1284

Reference Example 23

(−)-Ethyl 5-amino-6,7,8-trifluoro-1-(1,2-cis-2-fluoro-1-cyclopropyl)-4-oxo-1,4-dihydroquinoline-3-carboxylate (16b):

The nitro compound (15b) (1.60 g), 3 ml of Raney nickel, and 120 ml of ethanol were mixed, and the mixture was shaken for 4.5 hours in a hydrogen atmosphere. The catalyst was removed by filtration through Celite, and the filtrate was concentrated under reduced pressure. The residue was subjected to silica gel column chromatography using chloroform as an eluent. The fractions of product (16b) were combined, and the solvent was removed under reduced pressure. The residue was recrystallized from ethanol to obtain 620 mg of the titled compound (16b) as a pale yellow crystal.

Melting Point: 191°–193° C.

$[\alpha]_D$: −25.9° (c=0.65, chloroform)

Elementary analysis for $C_{15}H_{12}F_4N_2O_3$ Calcd. (%): C 52.33; H 3.51; N 8.14 Found (%): C 52.16; H 3.54; N 8.08

$^1$H-NMR (CDCl$_3$) δ ppm: 1.39 (3H, t, J=7 Hz), 1.4–1.8 (2H, m), 3.60–3.88 (1H, m), 4.38 (2H, q, J=7 Hz), 4.87 (1H, dm, J=63 Hz), 6.8–7.1 (2H, m), 8.38 (1H, s)

IR(KBr): $v_{max}$ cm$^{-1}$: 3436, 1683, 1653, 1593, 1464, 1284

Reference Example 24

5-Amino-6,7,8-trifluoro-1-(1,2-cis-2-fluoro-1-cyclopropyl)-4-oxo-1,4-dihydroquinoline-3-carboxylic acid (17a):

The ester (16a) (750 mg) and 10 ml of concentrated hydrochloric acid were mixed and the mixture was heated at 100° C. for 2 hours while stirring. To the reaction mixture was added 20 ml of water, and the precipitated crystals were collected by filtration to obtain 610 mg of the titled compound (17a) as a colorless crystal.

Melting Point: 297°–300° C.

Elementary Analysis for $C_{13}H_8F_4N_2O_3$ Calcd. (%): C 49.38; H 2.55; N 8.86 Found (%): C 49.43; H 2.91; N 8.84

$^1$H-NMR (DMSO-d$_6$) δ ppm: 1.4–2.1 (2H, m), 3.9–4.2 (1H, m), 5.08 (1H, dm, J=65 Hz), 7.72 (1H, s), 8.62 (1H, s)

IR(KBr): $v_{max}$ cm$^{-1}$: 3448, 3334, 1725, 1656, 1596, 1566, 1518

Reference Example 25

5-Amino-6,7,8-trifluoro-1-(1,2-cis-2-fluoro-1-cyclopropyl)-4-oxo-1,4-dihydroquinoline-3-carboxylic acid (17b):

The ester (16b) (588 mg) and 10 ml of concentrated hydrochloric acid were mixed and the mixture was heated at 100° to 110° C. for 2 hours while stirring. To the reaction mixture was added 20 ml of water, and the precipitated crystals were collected by filtration to obtain 514 mg of the titled compound (17b) as a colorless crystal.

Melting Point: 295°–300° C.

Elementary Analysis for $C_{13}H_8F_4N_2O_3$ Calcd. (%): C 49.38; H 2.55; N 8.86 Found (%): C 49.41; H 2.81; N 8.88

$^1$H-NMR (CDCl$_3$) δ ppm: 1.4–2.1 (2H, m), 3.9–4.2 (1H, m), 5.08 (1H, dm, J=65 Hz), 7.72 (1H, s), 8.62 (1H, s)

IR: $v_{max}$ cm$^{-1}$: 3448, 3334, 1725, 1656, 1596, 1566, 1518

EXAMPLE 7

(−)-5-Amino-7-[3-(S)-amino-1-pyrrolidinyl]-6,8-difluoro-1-(1,2-cis-2-fluoro-1-cyclopropyl)-4-oxo-1,4-dihydroquinoline-3-carboxylic acid (18a):

Five milliliters of trifluoroacetic acid was cooled with ice, and 230 mg of 3-(S)-1-t-butoxycarbonyl-3-(t-butoxycarbonylamino)pyrrolidine was dissolved therein, followed by stirring at room temperature for 30 minutes. The reaction mixture was evaporated to dryness under reduced pressure, and the residue was dissolved in 25 ml of acetonitrile. To the solution were added 160 mg of the carboxylic acid (17a) and 400 mg of triethylamine, and the mixture was heated under reflux for 12 hours. The reaction mixture was evaporated to dryness under reduced pressure, and 1N hydrochloric acid was added to the residue. After washing the mixture with chloroform, the aqueous layer was adjusted to a pH of 12 with a 1N sodium hydroxide aqueous solution, followed by washing with chloroform. The aqueous layer was then adjusted to a pH of 7.6 with hydrochloric acid, followed by extraction with chloroform. The extract was dried over anhydrous sodium sulfate, and the solvent was removed under reduced pressure. The residue was recrystallized from aqueous ammonia-ethanol to obtain 128 mg of the titled compound (18a) as a colorless crystal.

Melting Point: 224°–230° C.

$[\alpha]_D$: −4.72° (c=0.888, 0.1N NaOH aqueous solution)

Elementary Analysis for $C_{17}H_{17}F_3N_4O_3$ Calcd. (%): C 53.40; H 4.48; N 14.65 Found (%): C 53.28; H 4.08; N 14.54

$^1$H-NMR (NaOD)) δ ppm: 1.47–1.58 (1H, m), 1.67–1.78 (2H, m), 2.07–2.11 (1H, m), 3.28–3.44 (1H, m), 3.48–3.52(1H, m), 3.60–3.66 (1H, m), 3.71–3.78 (2H, m), 4.92 (1H, dm, J=72 Hz), 8.18 (1H, s)

IR: $v_{max}$ cm$^{-1}$: 3400, 1728, 1635, 1605, 1518, 1433, 1350, 1308

EXAMPLE 8

(+)-5-Amino-7-[3-(S)-amino-1-pyrrolidinyl]-6,8-difluoro-1-(1,2-cis-2-fluoro-1-cyclopropyl)-4-oxo-1,4-dihydroquinoline-3-carboxylic acid (18b):

Five milliliters of trifluoroacetic acid was cooled with ice, and 230 mg of 3-(S)-1-t-butoxycarbonyl-3-(t-butoxycarbonylamino)pyrrolidine was dissolved therein, followed by stirring at room temperature for 30 minutes. The reaction mixture was evaporated to dryness under reduced pressure, and the residue was dissolved in 25 ml of acetonitrile. To the solution were added 160 mg of the carboxylic acid (17b) and 400 mg of triethylamine, and the mixture was heated under reflux for 12 hours. The reaction mixture was evaporated to dryness under reduced pressure, and 1N hydrochloric acid was added to the residue. After washing the mixture with chloroform, the aqueous layer was adjusted to a pH of 12 with a 1N sodium hydroxide aqueous solution, followed by washing with chloroform. The aqueous layer was then adjusted to a pH of 7.6 with hydrochloric acid, followed by extraction with chloroform. The extract was dried over anhydrous sodium sulfate, and the solvent was removed under reduced pressure. The residue was recrystallized from aqueous ammonia-ethanol to obtain 68 mg of the titled compound (18b) as a colorless crystal.

Melting Point: 214°–217° C.

$[\alpha]_D$: +31.3° (c=0.268, 0.1N NaOH aqueous solution)

Elementary Analysis for $C_{17}H_{17}F_3N_4O_3 \cdot \frac{1}{2}H_2O$: Calcd. (%): C 52.18; H 4.64; N 14.32 Found (%): C 52.22; H 4.93; N 14.23

$^1$H-MNR (NaOD) δ ppm: 1.48-1.58 (1H, m),, 1.66–1.79 (2H, m), 2.06–2.12 (1H, m), 3.29–3.32 (1H, m), 3.48–3.52 (1H, m), 3.60–3.64 (1H, m), 3.70–3.78 (2H, m), 4.92 (1H, dm, J=72 Hz), 8.19 (1H, s)

1H: v max cm–$^1$; 3490, 1716, 1635, 1521, 1437, 1356, 1305

REFERENCE EXAMPLE 26

Synthesis of Optically Active 7-Amino-5-azaspiro[2.4]-heptane:

5-[(1R)-Phenylethyl]-4.7-dioxo-5-azaspiro[2.4]-heptane (19):

To 10.4 g of ethyl acetoacetate were added 15 g of 1,2-dibromoethane, 23 g of potassium carbonate, and 150 ml of N,N-dimethylformamide (DMF), and the mixture was stirred at room temperature for 2 days. Any insoluble matter was removed by filtration, and the filtrate was evaporated to dryness under reduced pressure. To the residue was added water, and the mixture was extracted with chloroform. The chloroform extract was dried over anhydrous sodium sulfate, and the solvent was removed under reduced pressure. The resulting pale yellow oily substance was subjected to distillation under reduced pressure to obtain 7.5 g of ethyl 1-acetyl-1-cyclopropanecarboxylate having a boiling point of 70° to 71° C./2 to 3 mmHg.

$^1$H-NMR (CDCl$_3$) δ ppm: 1.30 (3H, t, J=7 Hz), 1.48 (4H, s), 2.49 (3H, s), 4.24 (2H, q, J=7 Hz)

In 200 ml of ethanol was dissolved 35.7 g of the above obtained compound, and 40 g of bromine was added dropwise to the solution at room temperature while stirring. After the stirring was continued at room temperature for 2 hours, the excess bromine and the solvent were removed under reduced pressure to obtain ethyl 1-bromoacetyl-1-cyclopropanecarboxylate, which was then, without further purification, dissolved in 200 ml of ethanol. To the solution were simultaneously added dropwise 33 g of R-(+)-1-phenylethylamine and 27 g of triethylamine over a period of 1 hour while stirring under ice-cooling. After the addition, the reaction temperature was raised to room temperature, and the stirring was continued at room temperature for 2 days. Any insoluble matter was removed by filtration, and ethanol was removed from the filtrate under reduced pressure. The residue was dissolved in 300 ml of ethyl acetate, and the solution was washed successively with 1N hydrochloric acid, a saturated sodium hydrogen-carbonate aqueous solution, and a saturated sodium chloride aqueous solution in this order. The organic layer was dried over anhydrous sodium sulfate, and the solvent was removed under reduced pressure. The residue was subjected to 200 g of silica gel column which was eluted with 0 to 2% methanolic chloroform to obtain the titled compound (19) as a colorless crystal.

Melting Point: 98°–103° C.

$^1$H-NMR (CDCl$_3$) δ ppm: 1.62 (3H, d, J=7.2 Hz), 3.5 (1H, d, J=18 Hz), 3.9 (1H, d, J=18 Hz), 5.82 (1H, q, J=7.2 Hz), 7.36 (5H, s)

2) 5-[(1R)-Phenylethyl]-7-hydroxyimino-4-oxo-5-azaspiro [2.4]heptane (20):

To 3.35 g of Compound (19) were added 1.6 g of hydroxylamine hydrochloride, 2.3 g of triethylamine, and 80 ml of ethanol, and the mixture was stirred at room temperature for 2 hours. The solvent was removed under reduced pressure, and chloroform was added to the residue. The mixture was washed successively with a 10% citric acid aqueous solution and a saturated sodium chloride aqueous solution. The organic layer was dried over anhydrous sodium sulfide. The solvent was removed under reduced pressure to obtain 3.5 g of the titled compound (20) as a colorless crystal.

Melting Point: 188°–194° C.

$^1$H-NMR (CDCl$_3$) δ ppm: 1.2–1.4 (2H, m), 1.53 (3H, d, J=7.2 Hz & 2H, m), 3.8 (1H, d, J=18 Hz), 4.16 (1H, d, J=18 Hz), 5.63 (1H, q, J=7.2 Hz), 7.32 (5H, s)

3) 7-Amino-4-oxo-5-[(1R)-Phenylethyl]-5-azaspiro[2.4]-heptane (21a, 21b):

To 150 ml of methanol were added 3.5 g of Compound (20) and 7.5 ml of Raney nickel, and catalytic reduction was carried out at room temperature for 12 hours. After the catalyst was removed by filtration, the solvent was removed from the filtrate under reduced pressure. The residue was subjected to a 100 g of silica gel column eluted with a mixed solvent of 5% methanol/chloroform which was to yield 1.0 g of the entitled compound (21b) from the earlier fraction and 0.8 g of the titled compound (21a) from the later fraction each as a colorless oily substance.

Compound (21b):
 ¹H-NMR (CDCl₃) δ ppm: 0.8–1.4 (4H, m), 1.52 (3H, d, J=7 Hz), 2.87 (1H, dd, J=10, & 3 Hz), 3.3–3.9 (2H, m), 4.27 (2H, br. s), 5.42 (1H, q, J=7 Hz), 7.29 (5H, s)

Compound (21a):
 ¹H-NMR (CDCl₃) δ ppm: 0.6–1.3 (4H, m), 1.40 (2H, s), 1.53 (3H, d, J=7.2 Hz), 2.99 (1H, dd, J=12.8, & 7.2 Hz), 3.15–3.45 (2H, m), 5.52 (1H, q, J=7.2 Hz), 7.30 (5H, s)

4) 7-Amino-5-[(1R)-Phenylethyl]-5-azaspiro[2.4]heptane (22a, 22b):

To 50 ml of anhydrous tetrahydrofuran were added 1.0 g of Compound (21b) and 500 mg of lithium aluminum hydride, and the mixture was refluxed for 17 hours. After cooling, 0.5 ml of water, 0.5 ml of a 15% sodium hydroxide aqueous solution, and 1.5 ml of water were successively added to the reaction mixture in this order, followed by stirring well at room temperature for 30 minutes. Any insoluble matter was removed by filtration and thoroughly washed with tetrahydrofuran. The filtrate and the washing were combined and dried. The solvent was removed under reduced pressure to obtain 940 mg of the titled compound (22b) as a pale yellow oily substance. In the same manner, 755 mg of the titled compound (22a) was obtained from 800 mg of Compound (21a).

Compound (21b):
 ¹H-NMR (CDCl₃) δ ppm: 0.2–0.8 (4H, m), 1.35(3H, d, J=6.6 Hz), 1.6–2.0 (2H, br, m), 2.2–3.1 (4H, m), 3.24 (1H, q, J=6.6 Hz), 3.5–3.9 (1H, m), 7.28 (5H, br. s)

Compound (22a):
 ¹H-NMR (CDCl₃) δ ppm: 0.3–0.9 (4H, m), 1.36 (3H, d, J=6.7 Hz), 1.8–2.2 (2H, m), 2.2–3.2 (4H, m), 3.24 (1H, q, J=6.7 Hz), 3.6–3.9 (1H, m), 7.28 (5H, br, s)

5) 7-(t-Butoxycarbonylamino)-5-[(1R)-phenylethyl]-5-azaspiro[2.4]heptane (23a, 23b):

To 20 ml of anhydrous tetrahydrofuran were added 764 mg of Compound (22b) and 1.3 g of Boc-ON [Boc-ON; 2-(t-Butoxycarbonyloxyimino)-2-phenylacetonitrile

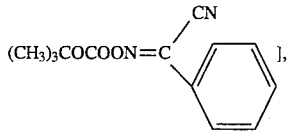

], and the mixture was stirred at room temperature for 4 hours. Ethyl acetate was added to the reaction mixture, and the mixture was washed twice with a 1N sodium hydroxide aqueous solution and then once with water, followed by extraction with a 10% citric acid aqueous solution. The aqueous extract was washed once with ethyl acetate, and a 15% sodium hydroxide aqueous solution was added to the aqueous layer under cooling to make it alkaline. The mixture was extracted three times with chloroform, and the organic layer was washed with a saturated sodium chloride aqueous solution and then dried. The solvent was removed under reduced pressure, and the residue was subjected to silica gel column chromatography (silica gel: 20 g; eluent: chloroform:methanol=20:1, 10:1) to obtain 690 mg of the titled compound (23b). This compound was allowed to stand to crystallize, followed by washing with n-hexane. The titled compound (23a) was obtained in the same manner.

Compound (23b) (colorless crystal):
 Melting Point: 103°–105° C.
 [α]_D: 15.2° (c=1.475, chloroform)
 ¹H-NMR (CDCl₃) δ ppm: 0.4–0.9 (4H, m), 1.36 (3H, d, J=7.2 Hz), 1.44 (9H, s), 2.42 (2H, AB q, J=10.2 Hz), 2.79 (2H, d, J=5.6 Hz), 3.24 (1H, q, J=7.2 Hz), 3.6–4.0 (1H, m), 4.6–5.1 (1H, br, d), 7.28 (5H, s)
 Elementary qAnalysis for C₁₉H₂₈N₂O₂: Calcd. (%): C 72.12; H 8.92; N 8.85 Found (%): C 71.63; H 9.07; N 8.64

Compound (23a) (colorless crystal):
 Melting Point: 94°–97° C.
 [α]_D: +47.6° (c=0.89, chloroform)
 ¹H-NMR (CDCl₃) δ ppm: 0.4–0.9 (4H, m), 1.33 (3H, d, J=6.6 Hz), 1.40 (9H, s), 2.29 (1H, d, J=9 Hz), 2.44 (1H, dd, J=10.8 & 3.6 Hz), 2.77 (1H, d, J=9 Hz), 2.88 (1H, dd, J=10.8 & 5.3 Hz), 3.22 (1H, q, J=6.6 Hz), 3.6–3.9 (1H, m), 4.7–5.2 (1H, br, d), 7.27 (5H, s)
 Elementary aAnalysis for C₁₉H₂₈N₂O₂: Calcd. (%): C 72.12; H 8.92; N 8.85 Found (%): C 71.86; H 9.36; N 8.68

6) 7-t-Butoxycarbonylamino-5-azaspiro[2.4]heptane (24a, 24b)

To 30 ml of ethanol were added 650 mg of Compound (23b) and 500 mg of 50% hydrated palladium-on-carbon, and catalytic reduction was effected under heating at a pressure of 4.2 atoms. After 6 hours, the catalyst was removed by filtration, and the solvent was removed under reduced pressure. To the oily residue was added ethyl acetate, followed by extracting twice with a 10% citric acid aqueous solution. The aqueous extract was made alkaline with a 15% sodium hydroxide aqueous solution and then extracted three times with chloroform. The chloroform layer was washed with water and dried. The solvent was removed under reduced pressure to yield 440 mg of the titled compound (24b) as a crude product. The titled compound (24a) was obtained in the same manner as above. The NMR spectra of Compounds 24b) and (24a) were in complete agreement with each other.

Compound (24)
 ¹H-NMR (CDCl₃) δ ppm: 0.4–1.0 (4H, m), 1.42 (9H, s), 2.71 (1H, d, J=10.2 Hz), 2.92 (1H, dd, J=10.8 & 3.6 Hz), 3.01 (1H, d, J=10.2 Hz), 3.33 (1H, dd, J=10.8 & 5.4 Hz), 3.5–3.9 (1H, m), 5.0–5.4 (1H, br, d)

EXAMPLE 9

7-(7-t-Butoxycarbonylamino-5-azaspiro[2.4]heptan-5-yl)-8-chloro-6-fluoro-1-(1,2-cis-2-fluoro-1-cyclopropyl)-1,4-dihydro-4-oxoquinoline-3-carboxylic acid (25bb):

In 0.6 ml of acetonitrile were dissolved 160 mg of 8-chloro-6,7-difluoro-1-(1,2-cis-2-fluoro-1-cylopropyl)-1,4-dihydro-4-oxoquinoline-3-carboxylic acid (12b), 150 mg of the amine compound (24b), and 0.5 ml of triethylamine, and the solution was heated under reflux for 5 hours. After cooling, the precipitated colorless crystals were collected by filtration. The solvent of the mother liquor was removed under reduced pressure, and the residue was purified by silica gel preparative TLC using a developing solvent of chloroform-methanol (5:1 by volume). The purified product and the above-obtained crystals were combined to give 255 mg of the titled compound (25bb).

Melting Point: 213°–218° C.
 ¹H-NMR (CDCl₃) δ ppm: 0.6–1.0 (6H, m), 1,45 (9H, s), 7.99 (1H, d, J=13.1 Hz), 8.74, 8.78 (each 0.5H, s)

EXAMPLE 10

(−)-7-(7-Amino-5-azaspiro[2.4]heptan-5-yl)-8-chloro-6-fluoro-1-(1,2-cis-2-fluoro-1-cylcopropyl)-1,4-dihydro-4-oxoquinoline-3-carboxylic acid (26bb):

To 255 mg of the Boc-compound (25bb) as obtained in Example 9 were added 0.5 ml of anisole and 10 ml of trifluoroacetic acid under ice-cooling. After warming to room temperature, the mixture was stirred for 30 minutes. The solvent was removed under reduced pressure, a 1N sodium hydroxide aqueous solution was added to the residue adjusting a pH of 11 to 12. The alkaline aqueous solution was washed twice with chloroform. The aqueous layer was adjusted to a pH of about 7 with concentrated hydrochloric acid and a 10% citric acid aqueous solution and extracted three times with chloroform. The extract was washed with water and dried over anhydrous sodium sulfate. The solvent was removed under reduced pressure, and the resulting solid was recrystallized from ethanol-concentrated aqueous ammonia to obtain 142 mg of the titled compound (26bb) as a colorless crystal.

Melting Point: 127°–140° C. (with decomposition)

$[\alpha]_D$: 199.2° (c=0.24, 1N NaOH)

Elementary Analysis for $C_{19}H_{18}N_3O_3F_2Cl \cdot \frac{1}{4}H_2O$ Calcd. (%): C 55.08; H 4.50; N 10.14 Found (%): C 54.86; H 4.80; N 10.03

As the compound obtained in this experiment was obtained by a convention of compound 11b, so the titled compound is correctly named (−)-7-17-amino-3-azaspiro[2.4]heptan-5-yl)-8-chloro-6-fluoro-1-[2-(S)-2-fluoro-1-(R)-cyclopropyl]-4-oxo-1.4-dihydroquinoline-7-carboxylic acid.

Recrystallization of the compound obtained in this Example from an aqueous ethanol gave another crystal showing the following physical data.

Melting Point: 127.3°–135.5° C.

$[\alpha]_D$: 179° (c=1.12, 1N NaOH)

Elementary Analysis for $C_{19}H_{18}N_3O_3F_2Cl \cdot 3/2H_2O$: Calcd. (%): C 52.23; H 4.85; N 9.61 Found (%): C 52.16; H 4.70; N 9.53

And it was further confirmed that the configuration around the carbon atom at 7-position in the 7-amino-5-azaspiro[2.4]heptan-5-yl group was (S).

EXAMPLE 11

Synthesis of Compound (26ab)

Compound (26ab) was obtained from Compound (12a) and Compound (24b) in the same manner as described in Examples 9 an 10.

Melting Point: 123°–128° C. (with decomposition)

$[\alpha]_D$: +21.5° (c=0.195, 1N NaOH)

Elementary Analysis for $C_{19}H_{18}N_3O_3F_2Cl \cdot \frac{1}{2}H_2O$ Calcd. (%): C 54.49; H 4.57; N 10.03 Found (%): C 54.33; H 4.73; N 9.81

EXAMPLE 12

Synthesis of Compound (26ba)

Compound (26ba) was synthesized from Compound (12b) and Compound (24a) in the same manner as described in Examples 9 and 10.

Melting Point: 121°–127° C. (with decomposition)

$[\alpha]_D$: 21.1° (c=0.275, 1N NaOH)

Elementary Analysis for $C_{19}H_{18}N_3O_3F_2Cl \cdot \frac{1}{2}H_2O$ Calcd. (%): C 54.49; H 4.57; N 10.03 Found (%): C 54.77; H 4.43; N 9.86

EXAMPLE 13

Synthesis of Compound (26aa)

Compound (26aa) was synthesized from Compound (12a) and Compound (24a) in the same manner as in Examples 9 and 10.

Melting Point: 126°–145° C. (with decomposition)

$[\alpha]_D$: +186.6° (c=0.228, 1N NaOH)

Elementary Analysis for $C_{19}H_{18}N_3O_3F_2Cl \cdot 3/4H_2O$: Calcd. (%): C 53.91; H 4.64; N 9.93 Found (%): C 53.80; H 4.47; N 9.82

Reference Example 27

(−)-Ethyl 7-chloro-6-fluoro-1-(1,2-cis-2-fluoro-1-cyclopropyl)-4-oxo-1,4-dihydro-1,8-naphthyridine-3-carboxylate (29a)

A mixture of 1 g of ethyl 2,6-dichloro-5-fluoronicotinoylacetate (27), 3 ml of ethyl orthoformate, and 6 ml of acetic anhydride was heated at 120° C. for 1 hour while stirring. The reaction mixture was evaporated to dryness under reduced pressure, and the residue was dissolved in 10 ml of dichloromethane.

Ten milliliters of trifluoroacetic acid was cooled with ice, and 750 mg of (+)-cis-1-(t-butoxycarbonylamino)-2-fluorocyclopropane (4a) was dissolved therein. The solution was stirred at room temperature for 20 minutes, followed by evaporation to dryness under reduced pressure. The residue was suspended in 20 ml of dichloromethane, and 2.0 g of triethylamine was added thereto under ice-cooling. To the suspension was further added the above-prepared dichloromethane solution, followed by stirring at room temperature for 30 minutes.

The reaction mixture was washed with water and dried over anhydrous sodium sulfate. The solvent was removed under reduced pressure. The residue was subjected to column chromatography using 50 g of silica gel using chloroform as an eluent to yield 1.29 g of ethyl 2-(2,6-dichloro-5-fluoronicotinoyl)-3-(1,2-cis-2-fluoro-1-cyclopropyl)acrylate (28a) as a colorless oil.

$^1$H-NMR (CDCl$_3$) δ ppm: 1.06 (3H, t, J=7 Hz), 1.1–1.6 (2H, m), 2.86–3.18 (1H, m), 4.05 (2H, q, J=7 Hz), 4,78 (1H, dm, J=63 Hz), 7.36 (1H, d, J=7 Hz), 8.31 (1H, d, J=14 Hz)

In 25 ml of anhydrous dioxane was dissolved 1.29 g of Compound (28a), and 300 mg of 60% sodium hydride was added to the solution, followed by stirring for 1 hour. The reaction mixture was concentrated under reduced pressure, and to the residue was added 0.1N hydrochloric acid. The precipitated crystals were collected by filtration and washed successively with water and diethyl ether to obtain 860 mg of the titled compound (29a) as a colorless crystal.

Melting Point: 184°–185° C.

$[\alpha]_D$: −1.26° (c=0.793, chloroform)

Elementary Analysis for $C_{14}H_{11}F_2N_2O_3$ Calcd. (%): C 51.16; H 3.37; N 8.52 Found (%): C 51.12; H 3.26; N 8.52

$^1$H-NMR (CDCl$_3$) δ ppm: 1.41 (3H, t, J=7 Hz), 1.4–1.84 (2H, m), 3.50 (1H, m), 4.40 (2H, q, J=7 Hz), 5.02 (1H, dm, J=65 Hz), 8.43 (1H, d, J=7 Hz), 8.66 (1H, s)

Reference Example 28

(+)-Ethyl 7-chloro-6-fluoro-1-(1,2-cis-2-fluoro-1-cyclopropyl)-4-oxo-1,4-dihydro-1,8-naphthyridine- 3-carboxylate (29b):

A mixture of 1.0 g of ethyl 2,6-dichloro-5-fluoronicotinoylacetate (27), 3 ml of ethyl orthoformate, and 6 ml of acetic anhydride was heated at 120° C. for 1.5 hours while stirring. The reaction mixture was evaporated to dryness under reduced pressure, and the residue was dissolved in 10 ml of dichloromethane.

Ten milliliters of trifluoroacetic acid was cooled with ice, and 750 mg of (−)-cis-1-(t-butoxycarbonylamino)-2-fluorocyclopropane (4b) was dissolved therein. The solution was stirred at room temperature for 20 minutes, followed by evaporation to dryness under reduced pressure. The residue was suspended in 30 ml of dichloromethane, and 2.0 g of triethylamine was added thereto under ice-cooling. To the suspension was further added the above-prepared dichloromethane solution, and the mixture was stirred at room temperature for 30 minutes.

The reaction mixture was washed with water and dried over anhydrous sodium sulfate. The solvent was evaporated, and the residue was purified by column chromatography using 50 g of silica gel and chloroform as an eluent to obtain 1.29 g of ethyl 2-(2,6-dichloro-5-fluoronicotinoyl)-3-(1,2-cis-2-fluoro-1-cyclopropyl)acrylate (28b) as a colorless oil.

Compound (28b) (1.29 g) was reacted in the same manner as for Compound (28a) to obtain 936 mg of the titled compound (29b) as a colorless crystal.

Melting Point: 183°–185° C.

$[\alpha]_D$: +1.12° (c=1.07, chloroform)

Elementary Analysis for $C_{14}H_{11}F_2N_2O_3$ Calcd. (%): C 51.16; H 3.37; N 8.52 Found (%): C 51.39; H 3.24; N 8.49

Reference Example 29

(−)-7-chloro-6-fluoro-1-(1,2-cis-2-fluoro-1-cyclopropyl)-4-oxo-1,4-dihydro-1,8-naphthyridine-3-carboxylic acid (30a):

A mixture of 800 mg of Compound (29a) and 15 ml of concentrated hydrochloric acid was heated at 100° C. for 1.5 hours while stirring. Water was added to the reaction mixture, and the precipitated crystals were collected by filtration to yield 610 mg of the titled compound (30a) as a colorless crystal.

Melting Point: 215°–219° C.

$[\alpha]_D$: −20.65° (c=0.910, chloroform)

Reference Example 30

(+)-7-chloro-6-fluoro-1-(1,2-cis-2-fluoro-1-cyclopropyl)-4-oxo-1,4-dihydro-1,8-naphthyridine-3-carboxylic acid (30b):

A mixture of 870 mg of Compound (29b) and 20 ml of concentrated hydrochloric acid was heated at 100° C. for 2 hours while stirring. Water was added to the reaction mixture, and the precipitated crystals were collected by filtration to yield 715 mg of the titled compound (30b) as a colorless crystal.

Melting Point: 218°–220° C.

$[\alpha]_D$: +22.34° (c=0.555, chloroform)

EXAMPLE 14

7-[4-(S)-Amino-2-(S)-methyl-1-pyrrolidinyl]-6-fluoro-1-(1,2-cis-2-fluoro-1-cyclopropyl)-4-oxo-1,4-dihydro-1,8-naphthyridine-3-carboxylic acid (31a):

In 15 ml of trifluoroacetic acid was dissolved 300 mg of 4-(S)-amino-1-t-butoxycarbonyl-2-(S)-methylpyrrolidine (32) (cf. Terry Ronson, et al., *J. Med. Chem.*, Vol. 31, p.1598 (1988)), and the solution was stirred at room temperature for 20 minutes, followed by evaporation to dryness under reduced pressure. The residue was dissolved in 20 ml of acetonitrile, and 150 mg of Compound (30a) and 2 ml of triethylamine were added to the solution, followed by refluxing for 30 minutes. The reaction mixture was evaporated to dryness under reduced pressure, and hydrochloric acid was added to the residue. The mixture was washed with chloroform. The aqueous layer was adjusted to a pH of 13 with sodium hydroxide and washed with chloroform. The aqueous layer was adjusted to a pH of 7.5 and extracted with chloroform. The organic layer was dried over anhydrous sodium sulfate, and the solvent was removed under reduced pressure. Recrystallization of the residue from aqueous ammonia-ethanol yielded 150 mg of the titled compound (31a) as a colorless crystal.

Melting Point: 255°–258° C.

$[\alpha]_D$: −14.52° (c=0.413, 0.1N NaOH)

Elementary Analysis for $C_{17}H_{18}F_2N_4O_3 \cdot \frac{1}{4}H_2O$: Calcd. (%): C 55.36; H 5.06; N 15.19 Found (%): C 55.09; H 5.40; N 15.04

EXAMPLE 15

(−)-7-[3-(R)-[1-(S)-Aminoethyl]-1-pyrrolidinyl]-8-chloro-6-fluoro-1-(1,2-cis-2-fluorocyclopropyl)-4-oxo-1,4-dihydroquinoline-3-carboxylic acid (34b):

A mixture of 159 mg of (−)-8-chloro-6,7-difluoro-1-(1,2-cis-2-fluoro-1-cyclopropyl)-4-oxo-1,4-dihydroquinoline-3-carboxylic acid (12b), 160 mg of 3-(R)-[1-(S)-t-butoxycarbonylaminoethyl]pyrrolidine (cf. JP-A-61-311992), 400 mg of triethylamine, and 20 ml of acetonitrile was heated under reflux for 12 hours. The reaction mixture was concentrated under reduced pressure, and the residue was dissolved in chloroform. The organic solution was washed successively with a 10% citric acid aqueous solution and water, and dried over anhydrous sodium sulfate. The solvent was evaporated, and the residue was recrystallized from ethyl acetate-isopropyl ether to yield 220 mg of (−)-7-[3-(R)-[1-(S)-t-butoxycarbonylaminoethyl]-1-pyrrolidinyl]-8-chloro-6-fluoro-1-(1,2-cis-2-fluoro-1-cyclopropyl)-4-oxo-1,4-dihydroquinoline-3-carboxylic acid (33b).

Melting Point: 189°–193° C.

$[\alpha]_D$: 205° (c=0.985, chloroform)

Elementary Analysis for $C_{24}H_{28}ClF_2N_3O_5$ Calcd. (%): C 56.31; H 5.51; N 8.21 Found (%): C 56.16; H 5.48; N 8.21

In 10 ml of trifluoroacetic acid was dissolved 200 mg of Compound (33b), and the solution was stirred for 30 minutes. The reaction mixture was evaporated to dryness under reduced pressure, and the residue was dissolved in a 1N sodium hydroxide aqueous solution and washed with chloroform. The aqueous layer was adjusted to a pH of 7.4 with hydrochloric acid and extracted with chloroform. The organic layer was dried over anhydrous sodium sulfate, and the solvent was evaporated. The residue was recrystallized from aqueous ammonia-ethanol to obtain 140 mg of the titled compound (34b) as a colorless crystal.

Melting Point: 204°–207° C.

$[\alpha]_D$: 160.0° (c=0.605, 0.1N NaOH)

Elementary Analysis for $C_{19}H_{20}ClF_2N_3O_3 \cdot H_2O$: Calcd. (%): C 53.09; H 5.38; N 9.77 Found (%): C 53.20; H 5.17; N 9.66

Reference Example 31

Ethyl 2-(3-acetoxy-2,4,5-trifluorobenzoyl)-
3-(1,2-cis-2-fluoro-1-cyclopropyl)acrylate (36b):

A mixture of 1.0 g of ethyl 3-acetoxy-2,4,5-trifluorobenzoylacetate (35) (cf. JP-A-87-175485), 6 ml of ethyl orthoformate, and 6 ml of acetic anhydride was heated at 120° C. for 3 hours under stirring. The reaction mixture was evaporated to dryness under reduced pressure, and the residue was dissolved in 10 ml of dichloromethane.

In 5 ml of trifluoroacetic acid was dissolved 467 mg of (−)-cis-1-t-butoxycarbonylamino-2-fluorocyclopropane (4b), and the solution was stirred for 20 minutes, followed by evaporation to dryness under reduced pressure. The residue was suspended in 20 ml of dichloromethane, and 5 ml of a dichloromethane solution containing 500 mg of triethylamine was added dropwise thereto under ice-cooling, followed by stirring for 10 minutes. To the solution was added the above-prepared dichloromethane solution, and the mixture was stirred at room temperature for 16 hours. The reaction mixture was washed successively with a 10% citric acid aqueous solution and water. The organic layer was dried over anhydrous sodium sulfate, followed by evaporation under reduced pressure to obtain 1.25 g of the titled compound (36b).

Reference Example 32

(−)-Ethyl
6,7-difluoro-1-(1,2-cis-2-fluoro-1-cyclopropyl)-
8-methoxy-4-oxo-1,4-dihydroquinoline-3-carboxylate
(37b):

In 40 ml of dioxane was dissolved 1.25 g of Compound (36b), and 440 mg of potassium carbonate and 10 ml of water were added thereto, followed by stirring at room temperature for 19 hours. The reaction mixture was neutralized with hydrochloric acid, concentrated under reduced pressure, and extracted with chloroform. The extract was dried over anhydrous sodium sulfate, and the solvent was removed under reduced pressure. The residue was dissolved in 40 ml of anhydrous dioxane, and 300 mg of 60% sodium hydride and 1 ml of ethyl iodide were added thereto, followed by stirring at room temperature for 24 hours. The reaction mixture was concentrated under reduced pressure, and the residue was extracted with chloroform, washed with water, and dried over anhydrous sodium sulfate. The solvent was evaporated. The residue was recrystallized from isopropyl ether to obtain 235 mg of the titled compound (37b) as a colorless crystal.

Melting Point: 163°–64° C.

$[\alpha]_D$: 22.9° (c=0.490, chloroform)

$^1$H-NMR (CDCl$_3$) δ ppm: 1.40 (3H, t, J=7 Hz), 1.3–1.8 (2H, m), 3.7–4.0 (1H, m), 4.10 (3H, d, J=2 Hz), 4.38 (2H, q, J=7 Hz), 4.85 (1H, dm, J=63 Hz), 8.02 (1H, dd, J=9 Hz, & 8.5 Hz ), 8.55 (1H, s)

Elementary Analysis for C$_{16}$H$_{14}$F$_3$NO$_4$ Calcd. (%): C 56.31; H 4.13; N 4.10 Found (%): C 56.62; H 4.18; N 4.11

Reference Example 33-1

(±)-cis-4-Amino-1-benzyl-3-methyl-
2-oxopyrrolidine (45):

A mixture of 5.13 g of ethyl 1-benzyl-4-methyl-5-oxo-3-pyrrolidinecarboxylate (42, cf. JP-A-62-4284), 40 ml of 50% ethanol, and 2 g of sodium hydroxide was stirred at room temperature for 42 hours. To the reaction mixture was added 100 ml of water, and the mixture was washed with chloroform. The aqueous layer was neutralized with hydrochloric acid and extracted with ethyl acetate. The extract was dried over anhydrous sodium sulfate. The solvent was evaporated to obtain 3.40 g of (±)-1-benzyl-4-methyl-5-oxo-3-pyrrolidinecarboxylic acid (43) as a colorless crystal.

Compound (43) (3.40 g), 4.45 g of diphenylphosphorylazide, 1.9 g of triethylamine, and 50 ml of t-butyl alcohol were mixed and the mixture was heated under reflux for 12 hours. The reaction mixture was concentrated under reduced pressure, and the residue was dissolved in chloroform. The solution was washed successively with a 10% citric acid aqueous solution, a 2% sodium hydroxide aqueous solution, and water and dried over anhydrous sodium sulfate. The solvent was evaporated, and the residue was purified by silica gel column chromatography using chloroform-methanol (97.5:2.5 by volume) as an eluent to obtain 1.76 g of (±)-cis-1-benzyl-4-t-butoxycarbonylamino-3-methyl-2-oxopyrrolidine (44) as a colorless oil.

In 15 ml of trifluoroacetic acid was dissolved 1.76 g of Compound (44). After 1 hour, the solution was concentrated under reduced pressure. To the residue was added 100 ml of water, and the mixture was washed with benzene. The aqueous layer was adjusted to a pH of 12 with sodium hydroxide and extracted with chloroform. The organic layer was dried over anhydrous sodium sulfate, and the solvent was evaporated to obtain the titled compound (45) as a colorless oil.

$^1$H-NMR (CDCl$_3$) δ ppm: 1.25 (3H, d, J=7 Hz), 1.44 (2H, s), 2.16 (1H, dt, J=7 Hz), 2.83 (1H, dd, J=6.7 Hz, & 8 Hz), 3.14 (1H, m), 3.38 (1H, dd, J=6.7 Hz, & 8 Hz), 4.48 (2H, s), 7.28 (5H, s)

Reference Example 33-2

Optical Resolution of
cis-4-Amino-1-benzyl-3-methyl-2-oxopyrrolidine
(45):

In 40 ml of dichloromethane were dissolved 4.17 g of Compound (45) and 3.3 ml of pyridine, and a solution of 7.7 g of (S)-N-p-toluenesulfonylpyrolyl chloride in 50 ml of dichloromethane was added thereto dropwise, followed by stirring for 4 hours.

The reaction mixture was washed successively with 1N hydrochloric acid, a saturated sodium hydrogen-carbonate aqueous solution, and water, and dried over anhydrous sodium sulfate. The solvent was evaporated under reduced pressure, and the residue was subjected to silica gel column chromatography using ethyl acetate as an eluent to isolate the isomers. Each of the isomers was recrystallized from ethyl acetate to obtain 3.3 g and 3.6 g of cis-1-benzyl-3-methyl-4-[(S)-N-p-toluenesulfonylprolylamino]-2-oxopyrrolidine (46a) and (46b), respectively.

Compound (46a):
Rf (silica gel TLC; ethyl acetate): 0.69
Melting Point: 162° C.
$[\alpha]_D$: 87.3° (c=0.735, chloroform)

Compound (46b):
Rf (silica gel TLC; ethyl acetate): 0.61
Melting Point: 175°–177° C.
$[\alpha]_D$: −148.6° (c=0.665, chloroform)

Reference Example 33-3

(+)-cis-1-Benzyl-3-t-butoxycarbonylamino-
4-methylpyrrolidine (47a):

A mixture of 3.23 g of Compound (46a) and 50 ml of concentrated hydrochloric acid as heated under reflux for 5 hours, followed by concentration under reduced pressure. To the residue was added a 1N sodium hydroxide aqueous solution, and the solution was extracted with chloroform. The organic layer was dried over anhydrous sodium sulfate, and the solvent was evaporated to obtain 1.48 g of Compound (45a) as a colorless oil.

The product was dissolved in 10 ml of tetrahydrofuran, and the solution was added dropwise to a suspension of 2.0 g of lithium aluminum hydride in 50 ml of tetrahydrofuran. The mixture was heated under reflux for 24 hours. To the reaction mixture was added dropwise 10 ml of water under ice-cooling, and, after stirring for 30 minutes, any insoluble matter was removed by filtration. To the filtrate was added 1.92 g of Boc-ON, followed by stirring for 24 hours. The reaction mixture was concentrated under reduced pressure, and the residue was extracted with chloroform. The extract was washed successively with a 5% sodium hydroxide aqueous solution and water, and dried over anhydrous sodium sulfate. The solvent was then evaporated.

The residue was purified by silica gel column chromatography using chloroform-methanol (1:0 to 9:1 by volume) as an eluent to obtain 1.76 g of a crystal. To the product was added n-hexane, and the mixture was stirred thereby precipitating a dl compound. The crystals were collected by filtration, and the filtrate was concentrated. This procedure was repeated twice. One hundred milligrams of the dl compound was obtained from the filter cake and 1.61 g of the titled optically active compound (47a) from the mother liquor.

Melting Point: 48°–52° C.

$[\alpha]_D$: +27.2° (c=2.33, chloroform)

$^1$H-NMR (CDCl$_3$) δ ppm: 1.07 (3H, d, J=7 Hz), 1.43 (9H, s), 1.78–2.02 (2H, m), 2.62 (2H, d, J=5 Hz), 2.84–3.10 (1H, m), 3.55 (2H, s), 3.5–3.8 (1H, m), 4.8–5.2 (1H, broad), 7.23 (5H, s)

Reference Example 33-4

(–)-cis-1-Benzyl-3-t-butoxycarbonylamino- 4-methylpyrrolidine (47b):

In the same manner as for the synthesis of Compound (47a) but starting with 3.52 g of Compound (46b), 1.72 g of the titled compound (47b) was obtained.

Melting Point: 57°–61° C.

$[\alpha]_D$: 31.21°

Reference Example 33-5 cis-3-t-butoxycarbonylamino-4-methylpyrrolidine (39a), (39b):

Compound (47a) (1.61 g), 1.5 g of 5% palladium-on-carbon, and 80 ml of ethanol were mixed, and catalytic reduction was carried out for 5 hours while irradiating the mixture with an infrared lamp in a hydrogen atmosphere at a pressure of 4 atoms. After the reaction, the catalyst was removed by filtration, and the filtrate was concentrated to obtain 1.09 g of a crude product as a colorless oil. The product solidified as a carbonate on standing, which was used without purification.

In the same manner as for the synthesis of Compound (39a), 1.1 g of Compound (39b) was obtained as a colorless oil from 1.70 g of Compound (47b).

Reference Example 34

Ethyl 2-(2,4,5-trifluoro-3-methylbenzoyl)-3-(1,2-cis- 2-fluoro-1-cyclopropyl)acrylate (50b):

A mixture of 710 mg of ethyl 2,4,5-trifluoro-3-methylbenzoylacetate (prepared from 2,4,5-trifluoro-3-methylbenzxoic acid (48), cf. JP-A-62-215572), 6 ml of ethyl orthoformate, and 6 ml of acetic anhydride was heated at 120° C. for 2 hours while stirring. The reaction mixture was evaporated to dryness under reduced pressure, and the residue was dissolved in 10 ml of dichloromethane.

In 5 ml of trifluoroacetic acid was dissolved 580 mg of (–)-cis-1-t-butoxycarbonylamino-2-fluorocyclopropane (4b), and the solution was stirred for 30 minutes, followed by evaporation to dryness under reduced pressure. The residue was suspended in 20 ml of dichloromethane, and 700 mg of triethylamine was added thereto under ice-cooling. After stirring for 10 minutes, the above-prepared dichloromethane solution was added thereto, followed by allowing to stand overnight. The reaction mixture was washed with water and dried over anhydrous sodium sulfate. The solvent was evaporated and the residue was crystallized from n-hexane to obtain 787 mg of the titled compound (50b) as a pale yellow crystal.

Reference Example 35

(–)-Ethyl 6.7-difluoro-1-(1,2-cis-2-fluoro-1-cyclopropyl)- 8-methyl-4-oxo-1,4-dihydroquinoline- 3-carboxylate (51b):

In 20 ml of anhydrous dioxane was dissolved 600 mg of Compound (50b), and a suspension of 100 mg of 60% sodium hydride having been washed with n-hexane in a small amount of anhydrous dioxane was added to the solution. The mixture was stirred at room temperature for 1 hour, and 10 ml of a 10% citric acid aqueous solution was added thereto, followed by concentration under reduced pressure. The precipitated crystals were collected by filtration, washed successively with water, a small amount of ethanol, and diethyl ether to obtain 480 mg of the titled compound (51b) as a colorless crystal.

Melting Point: 230°–231° C.

$[\alpha]_D$: –80.0° (c=0.350, chloroform)

$^1$H-NMR (CDCl$_3$) δ ppm: 1.40 (3H, t, J=7 Hz), 1.1–1.7 (2H, m), 2.71 (3H, d, J=3.3 Hz), 3.77–3.98 (1H, m), 4.38 (2H, q, J=7 Hz), 4.85 (2H, dm, J=64 Hz), 8.12 (1H, dd, J=10 Hz), 8.54 (1H, d, J=3 Hz)

Reference Example 36

(–)-6,7-Difluoro-1-(1,2-cis-2-fluoro-1-cyclopropyl)- 8-methyl-4-oxo-1,4-dihydroquinoline- 3-carboxylic acid (52b):

A mixture of 480 mg of the ester compound (51b) and 10 ml of concentrated hydrochloric acid was heated at 120° C. for 75 minutes while stirring. After cooling, the precipitated crystals were collected by filtration and washed with water and ethanol to obtain 380 mg of the titled compound (52b) as a colorless crystal.

Melting Point: 204° C.

$[\alpha]_D$: –60.0° (c=0.100, chloroform)

¹H-NMR (CDCl₃) δ ppm: 1.3–1.9 (2H, m), 2.80 (3H, d, J=5.8 Hz), 4.1–4.4 (1H, m), 4.15 (1H, dm, J=64 Hz), 8.17 (1H, dd, J=16 Hz), 8.82 (1H, d, J=4 Hz), 14.2 (1H, s)

EXAMPLE 16

(–)-7-[3-(R)-(1-(S)-Aminoethyl)-1-pyrrolidinyl]-
6-fluoro-1-(1,2-cis-2-fluoro-1-cyclopropyl)-
8-methyl-4-oxo-1,4-dihydroquinoline-3-carboxylic
acid hydrochloride (54b):

A mixture of 198 mg of Compound (52b), 350 mg of 3-(R)-[1-(S)-t-butoxycarbonylaminoethyl]pyrrolidine, 5 ml of dimethyl sulfoxide, and 1.5 g of triethylamine was heated at 110° to 120° C. for 5 hours while stirring. The reaction mixture was evaporated to dryness under reduced pressure. The residue was dissolved in chloroform and the solution was washed with a 10% citric acid aqueous solution and then with water, and dried over anhydrous sodium sulfate. The solvent was evaporated.

The residue was subjected to preparative TLC which was developed with a mixed solvent of chloroform-methanol (95:5 by volume) to obtain 110 mg of 7-[3-(R)-[1-(S)-t-butoxycarbonylaminoethyl]pyrrolidinyl]6-fluoro-8-methyl-4-dihydroquinoline-3-carboxylic acid (53b) as a pale yellow powder.

¹H-NMR (CDCl₃) δ ppm: 1.24 (3H, d, J=7 Hz), 1.45 (9H, s), 1.2–1.9 (2H, m), 2.52 (3H, s), 1.9–2.7 (3H, m), 3.2–4.2 (6H, m), 4.73 (1H, d, J=8 Hz), 4.98 (1H, dm, J=65 Hz), 7.77 (1H, d, J=13 Hz), 8.70 (1H, d, J=3.5 Hz)

To 110 mg of Compound (53b) was added 5 ml of concentrated hydrochloric acid, and the mixture was stirred at room temperature for 10 minutes, followed by evaporation to dryness under reduced pressure. The residue was recrystallized from ethanol-diethyl ether to obtain 62 mg of the titled compound (54b) as a yellow crystal.

Melting Point: 149°–153° C.
$[\alpha]_D$: 34.4° (c=0.168, 1N HCl)

EXAMPLE 17

5-Amino-7-(7-amino-5-azaspiro[2.4]heptan-5-yl)-
6,8-difluoro-1-(1,2-cis-2-fluoro-1-cyclopropyl)
4-oxo-1,4-dihydroquinoline-3-carboxylic acid (56b):

A mixture of 100 mg of (–)-5-amino-6,7,8-trifluoro-1-(1,2-cis-2-fluoro-1-cyclopropyl)-4-oxo-1,4-dihydroquinoline-3-carboxylic acid (17b), 100 mg of 7-t-butoxycarbonylamino-5-azaspiro[2.4]heptane (24b), 300 mg of triethylamine, and 20 ml of acetonitrile was heated under reflux for 23 hours.

The reaction mixture was evaporated to dryness under reduced pressure, and the residue was dissolved in 100 ml of chloroform. The solution was washed successively with a 10% citric acid aqueous solution and water. The organic layer was dried over anhydrous sodium sulfate, and the solvent was evaporated. The residue was recrystallized from acetonitrile to obtain 120 mg of 5-amino-7-[7-t-butoxycarbonylamino-5-azaspiro[2.4]-heptan-5-yl]-6,8-difluoro-1-(1,2-cis-2-fluoro-1-cyclopropyl)-4-oxo-1,4-dihydroquinoline-3-carboxylic acid (55bb) as a yellow needle-like crystal.

Melting Point: 250°–253° C.

¹H-NMR (CDCl₃) δ ppm: 0.6–0.8 (2H, m), 0.8–1.0 (2H, m), 1.45 (9H, s), 1.3–1.8 (2H, m), 3.2–3.4 (1H, m), 3.6–3.9 (3H, m), 3.9–4.3 (2H, m), 4.85 (1H, dm, J=63 Hz), 4.7–5.0 (1H, broad), 8.51 (1H, s)

In 5 ml of trifluoroacetic acid was dissolved 120 mg of Compound (55bb), and the solution was stirred for 30 minutes, followed by evaporation to dryness under reduced pressure. The residue was dissolved in hydrochloric acid and the solution was washed with chloroform. The aqueous layer was adjusted to a pH of 7.4 and extracted with chloroform. The extract was dried over anhydrous sodium sulfate, and the solvent was evaporated under reduced pressure. The residue was recrystallized from aqueous ammonia-ethanol to obtain 65 mg of the titled compound (56bb) as a yellow crystal.

Melting Point: 213°–217° C.
$[\alpha]_D$: –96.7° (c=0.120, DMF)

EXAMPLE 18

7-[4-(S)-Amino-2-(S)-methyl-1-pyrrolidinyl]-
6-fluoro-1-(1,2-cis-2-fluoro-1-cyclopropyl)-
4-oxo-1,4-dihydro-1,8-naphthyridine-3-carboxylic
acid (31b):

In 15 ml of trifluoroacetic-acid was dissolved 300 mg of 4-(S)-amino-1-t-butoxycarbonyl-2-(S)-methylpyrrolidine (32), and the solution was stirred at room temperature for 20 minutes, followed by evaporation to dryness under reduced pressure. The residue was dissolved in 20 ml of anhydrous acetonitrile, and 150 mg of Compound (30b) and 2 ml of triethylamine were added to the solution, followed by refluxing for 15 minutes. The reaction mixture was evaporated to dryness under reduced pressure, and 1N hydrochloric acid was added to the residue. The mixture was washed with chloroform. The aqueous layer was made alkaline with 1N sodium hydroxide aqueous solution and washed with chloroform. The aqueous layer was adjusted to a pH of 7 and extracted with chloroform. The organic layer was dried and the solvent was evaporated. The residue was recrystallized from aqueous ammonia-ethanol to yield 130 mg of the titled compound (31b).

Melting Point: 247°–255° C. (with decomposition)
$[\alpha]_D$: +120° (c=0.950, 1N NaOH)

Elementary Analysis for $C_{17}H_{18}F_2N_4O_3 \cdot \frac{1}{4}H_2O$ Calcd. (%): C 55.36; H 5.06; N 15.19 Found (%): C 55.50; H 5.25; N 14.97

EXAMPLE 19

5-Amino-6,8-difluoro-1-(1,2-cis-2-fluoro-
1-cyclopropyl)-7-piperzinyl-4-oxo-quinoline-
3-carboxylic acid (57b)

A mixture of 75 mg of Compound (17b), 45 mg of anhydrous piperazine in 5 ml of acetonitrile was heated under reflux for 2 hours. The reaction mixture was evaporated under reduced pressure and the residue was recrystallized from ethanol to yield 72 mg of the titled compound (57b) as a yellow crystal.

Melting Point: 230°–239° C.
$[\alpha]_D$: +8.00° (c=0.225, 1N NaOH)

Reference Example 37

8,7-Difluoro-1-(1,2-cis-2-fluoro-1-cyclopropyl)-
8-methoxy-4-oxo-1,4-dihydroquinoline-
3-carboxylic acid BF₂-chelate (38b):

A mixture of 230 mg of the ester compound (37b) and 5 ml of 42% borofluoric acid was heated at 110° C. with stirring for 2 hours. After cooling, precipitated crystal was collected by filtration and washed with water to yield 210 mg of colorless crystal of the titled compound.

Melting Point: 281°–271° C.

By the reaction of cis-3-t-butoxycarbonylamino-4-methylpyrrolidine (38a) and the chelate compound (38b), 7-(cis-3-amino-4-methylpyrrolidinyl)-8-fluoro-8-methoxy-4-oxo-1,4-dihydroquinoline-3-carboxylic acid (40ba) is obtained. And further, by the reaction of the amine compound (24b) and the chelate compound (38b), 7-(7-amino-5-azaspiro[2.4]heptan-5-yl)-6-fluoro-8-methoxy-4-oxo-1,4-dihydroquinoline-3-carboxylic acid (41bb) is obtained.

One synthesis route for an optically active 8-amino-6-azaspiro[3.4]octane derivative as a homologue of compound 26bb C$_7$-substituent is given below.

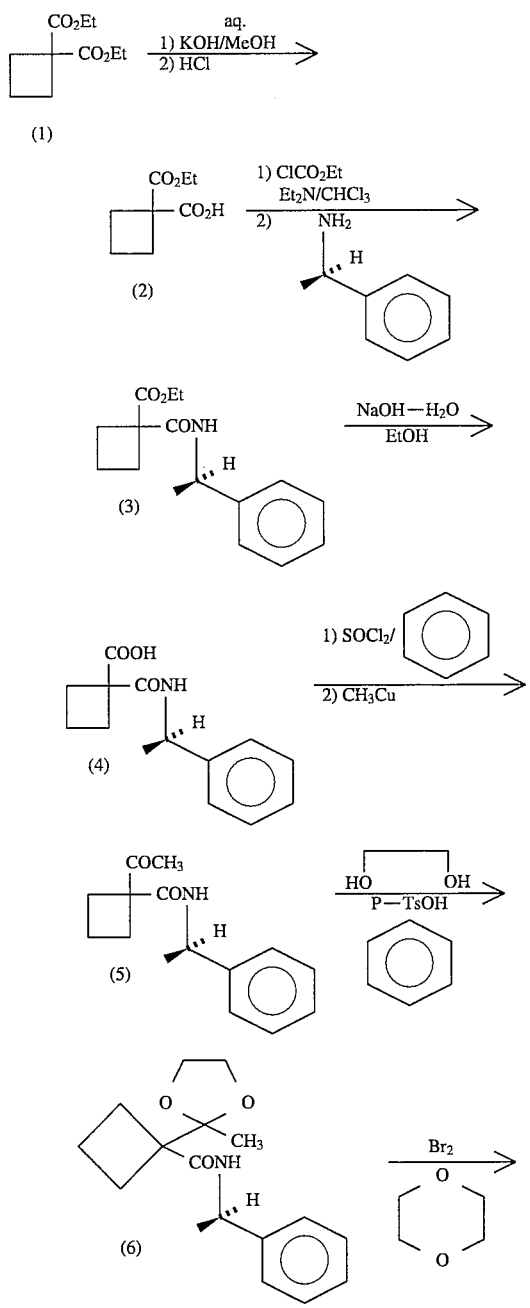

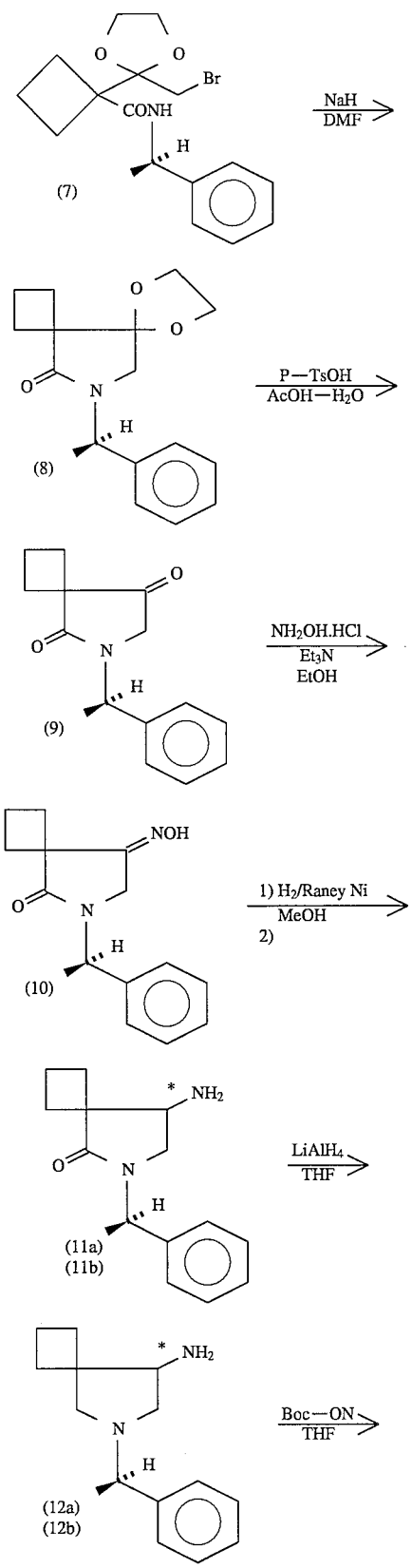

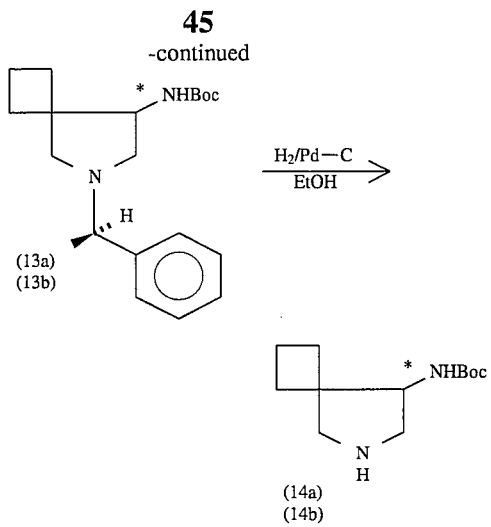

(13a)
(13b)

(14a)
(14b)

Reference Example 38-1

Ethyl hydrogen cyclobutane-1,1-dicarboxylate:

To an ice-cooled solution of 100 ml of diethyl cyclobutane-1,1-dicarboxylate in 110 ml of methanol was added 290 ml of a 10% (w/w) sodium hydroxide aqueous solution over a period of 60 minutes while stirring. The solution was then stirred at room temperature for 18 hrs. The organic solvent methanol was then removed under reduced pressure. The aqueous layer was washed with chloroform and the aqueous layer was then acidified with conc. hydrochloric acid to a pH of 2.5. The aqueous layer was extracted with ethyl acetate, and the extract was washed with a sat. sodium chloride aqueous solution. The extract was dried and the solvent ethyl acetate was removed under reduced pressure. The residue was purified by vacuum distillation to yield 85 g of the titled compound as a colorless oil.

$^1$H-NMR(CDCl$_3$) δ ppm;1.30(3H, t, J=7.2 Hz), 1.9–2.2(2H, m), 2.5–2.8(4H,m), 4.25(2H, q, J=7.2 Hz)

Reference Example 38-2

Ethyl 1-[N-[1-(R)-phenylethyl]amido]-cyclobutane 1-carboxylate:

To an ice-cooled solution of 55.5 g of ethyl hydrogen cyclobutane-1,1-dicarboxylate and 40.2 g of triethylamine in 300 ml of chloroform was added a solution of 38.6 g of ethyl chloroformate in 100 ml of chloroform with stirring, and the mixture was then stirred at room temperature for 20 min. The mixture was cooled on an ice bath and there was then added thereto a solution of 40.2 g of (R)-D-(+)-phenylethylamine in 100 ml of chloroform while stirring, and the mixture was then stirred at room temperature for 30 min. The mixture was then washed with 10% (w/w) aqueous citric acid and then washed with a sat. sodium chloride aqueous solution and dried. The solvent was removed under reduced pressure to yield 88 g of the titled compound as a colorless oil.

$^1$H-NMR(CDCl$_3$) δ ppm;1.24(3H, t, J=7.2 Hz), 1.48 (3H, d, J=7.2 Hz), 1.7–2.2(2H, m), 2.3–2.8 (4H, m), 4.22 (2H, q, J=7.2 Hz), 5.15 (1H, quint., J=7.2 Hz), 6.4–6.7 (1H, m), 7.36(5H, s)

Reference Example 38-3

1-[N-[1-(R)-phenylethyl]amido]-cyclobutane-1-carboxylic acid:

A mixture of 88 g of ethyl 1-[N-{1-(R)-phenylethyl]amido]-cyclobutane-1-carboxylate, 90 ml of a 20% (w/w) sodium hydroxide aqueous solution and 200 ml of ethanol was stirred at room temperature for 1 hr. Water was added to the mixture water and the mixture was washed with chloroform. The aqueous layer which was present was cooled on an ice bath and was acidified with conc. hydrochloric acid. The mixture was extracted with ethyl acetate and the extract was washed with water and dried. The solvent was removed under reduced pressure and the residual crystals were washed with n-hexane to yield 73 g of the titled compound.

mp:103°–106° C.

[α]$_D$ +55.5° (c=0.804, CHCl$_3$)

$^1$H-NMR(CDCl$_3$) δ ppm;1.50(3H, d, J=7.2 Hz), 1.7–2.2(2H, m), 2.4–2.8(4H, m), 5.18(1H, quint., J=7.2 Hz), 6.90(1H, br.d, J=7.2 Hz), 7.36(5H, s), 9.80(1H, br.s)

Anal. Calcd. for $C_{14}H_{17}NO_3$: C, 68.00; H, 6.93; N, 5.66
Found: C, 67.94; H, 6.86; N, 5.52

Reference Example 38-4

N-[1-(R)-Phenylethyl]-1-acetyl-1-cyclobutane-carboxamide:

A mixture of 20 g of 1-[N-[1-(R)-phenylethyl]amido] cyclobutane-1-carboxylic acid, 100 ml of thionyl chloride and 200 ml of anhydrous benzene was heated under reflux for 3 hrs. The solvent was removed under reduced pressure to yield the acid chloride as colorless crystals. To 600 ml of anhydrous tetrahydrofuran there was added 33.5 g of cuprous iodide, and the mixture was cooled so that the temperature of the reaction mixture in the reactor was −20° C. under a nitrogen atmosphere. To the cold mixture was added 100 ml of an ethereal solution of methyl lithium (1.6M ethereal solution, commercially available) over a period of 30 mins. The mixture was stirred at −20° C. for 20 mins. To the stirred mixture there was dropwise added a solution of the acid chloride obtained above in 100 ml of anhydrous tetrahydrofuran keeping the temperature of the system in the reactor at −20° C., and the mixture was stirred at −20° C. for 2 hrs., whereafter the temperature of the reaction system was raised to room temperature. The mixture was then stirred at room temperature for 2 hrs. To the mixture was added 30 ml of 1N hydrochloric acid and the solvent was removed under reduced pressure. To the resulting residue, ethyl acetate was added and insoluble material was removed by filtration. The resulting organic layer was washed with a 5% (w/w) sodium thiosulfate aqueous solution and then with water and dried. The solvent was removed under reduced pressure and the resulting crystalline residue was washed with isopropyl ether to yield 9.7 g of the titled compound. The solvent of the filtrate was removed under reduced pressure and the resulting residue was purified by flash column chromatography using 100 g of silica gel eluted by a mixture of n-hexane and ethyl acetate(2:1, v/v). As a result of this purification, 2.8 g of the titled compound was obtained.

mp; 57°–60° C.

$^1$H-NMR(CDCl$_3$) δ ppm;1.45(3H, d, J=7.2 Hz), 1.7–2.2(2H, m), 2.10(3H, s), 2.3–2.7(4H, m), 5.10(1H, quint., J=7.2 Hz), 5.8–6.0(1H, m), 7.30(5H, s)

Anal. Calcd. for $C_{15}H_{19}NO_2$: C, 73.44; H, 7.81; N, 5.71
Found: C, 73.12; H, 7.71; N, 5.66

Reference Example 38-5

N-[1-(R)-phenylethyl]-1-(1,1-ethylenedioxyethyl)-1-cyclobutanecarboxamide:

A mixture, of 13.9 g of N-[1-(R)-phenylethyl]-1-acetyl-1-cyclobutanecarboxamide, 15 ml of ethylene glycol, a catalytic amount of p-toluenesulfonic acid and 100 ml of benzene was heated under reflux for 3 hrs. The water formed in the reaction was removed using a Dean-Stark apparatus. After cooling, the mixture was washed with a saturated sodium bicarbonate aqueous solution, then washed with water and then dried. The solvent was removed under reduced pressure to yield 16.5 g of the titled compound as a colorless oil.

$^1$H-NMR(CDCl$_3$) δ ppm;1.14(3H, s), 1.48(3H, d, J=7.2 Hz), 1.7–2.1(2H, m), 2.1–2.7 (4H, m), 4.10 (4H, s), 5.16(1H, quint, J=7.2 Hz), 6.9–7.1 (1H, m), 7.40(5H, s)

Reference Example 38-6

N-[1-(R)-phenylethyl]-1-(2-bromo-1,1-ethylenedioxoethyl)-1-cyclobutanecarboxamide:

To 40 ml of anhydrous dioxane that was dropwise added 13 g of bromine and the mixture was then stirred at room temperature for 20 min. To the solution was added a solution of 18.3 g of N-[1-(R)-phenylethyl]-1-(1,1-ethylenedioxyethyl)-1-cyclobutanecarboxamide in 50 ml of anhydrous dioxane and the mixture was stirred at room temperature for 20 hr. Ethyl acetate was added to the mixture and the mixture was washed with a 5% (w/w) sodium thiosulfate aqueous solution and then with water and then dried. The solvent was removed under reduced pressure to yield 23 g of the titled compound as a yellow oil. This product was used in the following reaction (Ref. Ex. 38-7) without further purification.

$^1$H-NMR(CDCl$_3$) δ ppm;1.48(3H, d, J=7.2 Hz), 1.6–2.1(2H, m), 2.1–2.7(4H, m), 3.34(2H, AB-q, J=11 Hz), 4.0–4.6(4H, m), 5.10(1H, quint, J=7.2 Hz), 6.70(1H, br.d, J=7.2 Hz), 7.36(5H, s)

Reference Example 38-7

5,8-Dioxo-6-[1-(R)-phenylethyl]-6-azaspiro[3.4]octane-8-ethylene acetal:

A solution of 32.4 g of the N-[1-(R)-phenylethyl]-1-(2-bromo-1, ethylenedioxyethyl)-1-cyclobutanecarboxamide reaction production obtained in Ref. Ex. 38-6 in 150 ml of anhydrous N,N-dimethylformamide was cooled on an ice bath, and a suspension of 4.2 g of 60% sodium hydride (oil dispersion, the oil was removed by washing with n-hexane prior to use) in a small amount of anhydrous N,N-dimethylformamide was added to the solution. The mixture was stirred for 1 hr. The reaction mixture was diluted with ethyl acetate and the mixture was washed with a 10% (w/w) citric acid aqueous solution and then with water and then dried. The solvent was removed under reduced pressure and the residue was purified through flash column chromatography using 500 g of silica gel eluted by a mixture of n-hexane and ethyl acetate (2:1, v/v) to yield 23 g of the titled compound as a yellowish oil.

$^1$H-NMR(CDCl$_3$) δ ppm;1.48(3H, d, J=7.2 Hz), 1.6–2.6(6H, m), 2.80(1H, d, J=10.5 Hz), 3.08(1H, d, J=10.5 Hz), 3.96(4H, m), 5.52(1H, q, J=7.2 Hz), 7.30(5H, s), Reference Example 38-8

5,8-dioxo-5-[1-(R)-phenylethyl]-6-azaspiro[3.4]octane:

A mixture of 23 g of 5,8-dioxo-6-[1-(R)-phenylethyl]-6-azaspiro[3,4]octane-8-ethyleneacetal, 2 g of p-toluene-sulfonic acid, 200 ml of acetic acid and 100 ml of water was heated under reflux for 7 hrs. The solvent was then removed under reduced pressure. Ethyl acetate was added to the residue and the mixture was washed with a 1N sodium hydroxide aqueous solution and then with water and then dried. The solvent was removed under reduced pressure and the resulting residual crystal were washed with isopropyl ether to yield 15 g of the titled compound. The titled compound also was obtained from the filtrate.

mp; 68°–69° C.

(α)$_D$ +171.2° (c=0.819, CHCl$_3$)

$^1$H-NMR(CDCl$_3$) δ ppm;1.56(3H, d, J=7.2 Hz), 1.8–2.8(6H, m), 3.32(1H, d, J=17.5 Hz), 3.68(1H, d, J=17.5 Hz), 5.78(1H, J=7.2 Hz), 7.32(5H, s)

Anal. Calcd. for C$_{15}$H$_{17}$NO2: C, 74.05; H, 7.04; N, 5.76 Found: C, 74.21; H, 7.05; N, 5.62

Reference Example 38-9

6-[1-(R)-phenylethyl]-8-hydroxyimino-5-oxo-6-azaspiro [3.4]octane

To a solution of 15 g of 5,8-dioxo-5-[1-(R)-phenylethyl]-6-azaspiro[3.4]octane, 12 g of hydroxylamine hydrochloride in 100 ml of ethanol was added along with 18 g of triethylamine. The mixture was stirred at room temperature for 30 min. and then at 70° C. for 1 hr. The solvent was removed under reduced pressure and chloroform was added to the residue. The resulting chloroform layer was washed with water, a 10% (w/w) aqueous citric acid solution and with a saturated sodium chloride aqueous solution. The solvent was removed under reduced pressure and the resulting residual solid was washed with isopropyl ether to yield 12 g of the titled compound as colorless crystals.

mp;203°–208° C.

$^1$H-NMR(CDCl$_3$) δ ppm;1.56(3H, d, J=7.2 Hz), 1.9–2.8(6H, m), 3.68(1H, d, J=17 Hz), 4.08(1H, d, J=17 Hz), 5.64(1H, q, J=7.2 Hz), 7.32(5H, s), Reference Example 38-10

8-amino-5-oxo-6-[1-(R)-phenylethyl]-6-azaspiro[3.4]octane:

To a solution of 8.75 g of 6-[1-(R)-phenylethyl]-8-hydroxyimino-5-oxo-6-azaspiro[3.4]octane in 300 ml of methanol there was added 26 ml of Raney nickel, and reduction was carried out under a hydrogen atmosphere at room temperature for 14.5 hr. The catalyst was removed by filtration and the solvent was removed under reduced pressure. By the same procedure, 1.65 g of 6-[1-(R)-phenylethyl]-8-hydroxyimino-5-oxo-6-azaspiro-[3.4]octane was reduced using 5 ml of Raney nickel. The crude products were combined and purified by column chromatography using a column containing 380 g of silica gel. From a fraction of an eluant of 1% (v/v) methanolic chloroform, 3.2 g of the less polar isomer of the titled compound was obtained and 1.8 g of the more polar isomer thereof along with 4.4 g of a mixture of the two isomers.

$^1$H-NMR(CDCl$_3$) δ ppm;1.48(3H, d, J=7.2 Hz), 1.70–2.40(6H, m), 2.50(1H, dd, J=7.2, 12.6 Hz), 3.20–3.52(2H, m), 5.50(1H, q, J=7.2 Hz), 7.32(5H, s)

The RF value of the less polar isomer is larger than that of the more polar isomer (silica gel TLC plate; developing solvent, methanol: chloroform=1:20 (v/v))

Reference Example 38-11

8-amino-6-[1-(R)-phenylethyl]-6-azaspiro[3.4]octane (from the less polar amino compound:

To an ice-cooled solution of 3.2 g of 8-amino-5-oxo-6-[1-(R)-phenylethyl]-6-azaspiro[3.4]octane (the less polar compound obtained in Ref. Ex. 38-10) in 130 ml of anhydrous tetrahydrofuran there was gradually added 1 g of lithium aluminum hydride and then the mixture was heated under reflux for 2.5 hr. After cooling, 1 ml of water, 1 ml of a 15% (w/w) aqueous sodium hydroxide solution and 3 ml of water were added, in that order, to the ice-cooled reaction mixture. A resulting insoluble material was removed by filtration, and the solvent was removed under reduced pressure to yield 2.9 g of the titled compound.

$^1$H-NMR(CDCl$_3$) δ ppm;1.22–1.50(1H, m) 1.35(3H, d, J=7.2 Hz), 1.50–2.00(6H, m), 2.60–3.50(3H, m), 2.67(2H, br.s), 7.32(5H,s)

Reference Example 38-12

8-tert-butoxycarbonylamino-6-[1-(R)-phenylethyl]-6-azaspiro[3.4]octane:

To an ice-cooled solution of 2.9 g of 8-amino-6-[1-(R)-phenylethyl]-6-azaspiro[3.4]octane in 30 ml of tetrahydrofuran there was added 3.3 g of 2-(tertbutoxycarbonylamino)-2-phenylacetonitrile and the resulting mixture was stirred at room temperature for 30 min. The solvent was removed under reduced pressure, and ethyl acetate was added to the resulting residue. The mixture was washed with a 1N sodium hydroxide aqueous solution three times and then dried. The solvent was removed under reduced pressure and the resulting residue was purified by column chromatography using 50 g of silica gel. The column was eluted with chloroform, chloroform containing methanol and 4.1 g of the titled compound was obtained from a eluate when the eluant was chloroform containing 1% (v/v) of methanol.

$^1$H-NMR(CDCl$_3$) δ ppm;1.32(3H, d, J=7.2 Hz), 1.47(9H, s), 1.60 –2.20(6H, m), 2.30–2.90(4H, m) 3.60(1H., q, J=7.2 Hz), 3.80–4.15(1H, m), 4.90(1H, bs), 7.28(5H, s)

Reference Example 38-13

8-tert-butoxycarbonylamino-6-azaspiro[3.4]octane:

To a solution of 4.1 g of 8-tert-butoxycarbonylamino-6-[1-(R)-phenylethyl]-6-azaspiro[3.4]octane in 60 ml of ethanol there was added 4.5 g of 5% palladium on charcoal (50% wet) and reduction was carried out under a hydrogen atmosphere (H$_2$ pressure: 4 atm.) for 5 hrs. During the reduction, the reaction vessel was warmed by irradiation with a tungsten lamp. At 1 hr. from the beginning of the reduction, 2 g of the same catalyst was further added and the reduction continued for an additional 4 hours at the same condition to total 5 hours. The catalyst was removed by filtration and the solvent was removed under reduced pressure to yield 2.88 g of the titled compound.

$^1$H-NMR(CDCl$_3$) δ ppm;1.47(9H, s), 170–2.40 (6H, m), 2.90–3.60(4H, m), 4.20(1H, br.s)

"Palladium on charcoal (50% wet) is a commercially available catalyst containing water in an amount of 50 wt % based on the total weight of the catalyst.

Reference Example 38-14

8-tert-butoxycarbonylamino-6-azaspiro[3.4]-octane (from the more polar amino compound:

To a mixture of 1.8 g of the more polar amine compound having a lower Rf-value obtained in Ref. Ex. 38-10 in 80 ml of anhydrous terahydrofuran there was added 1 g of lithium aluminum hydride. The mixture was then heated under reflux for 13 hrs. After cooling on ice there was added thereto 1 ml of water 0.1 ml of a 15% (w/w) sodium hydroxide aqueous solution, 3 ml of water and the mixture was stirred for 30 min. A resulting insoluble material was removed by filtration. The filtrate was dried over anhydrous sodium sulfate and the solvent was removed under reduced pressure to yield 1.6 g of 8-amino-6-[1-(R)-phenylethyl]-6-azaspiro[3.4]-octane as a colorless oil. A mixture of 1.6 g of the product thus obtained, 20 ml of anhydrous tetrahydrofuran and 2 g of 2-(tert-butoxycarbonylamino)-2-phenylacetronitrile was stirred at room temperature for 2 hrs. To the mixture there was added ethyl acetate and the mixture was washed with a 1N sodium hydroxide aqueous solution and then with water and then dried. The solvent was removed under reduced pressure. The residue was purified by flash column chromatography using 50 g of silica gel. From a fraction eluted with chloroform and methanol(99:(v/v)) 1.9 g of 8-tertbutoxycarbonylamino) derivative was obtained. A mixture of 1.75 g of the 8-(tert-butoxycarbonylamino) derivative thus obtained and 2.5 g of 5% Pd/C (50% wet) in 40 ml of ethanol was shaken under a hydrogen atmosphere (H$_2$ pressure: 3 atm.) for 6 hrs. During the reaction, the reaction vessel was warmed by irradiation with a tungsten lamp. The catalyst was removed by filtration and then the solvent was removed under reduced pressure from the filtrate to yield 1.24 g of the 8-tert-butoxycarbonylamino-6-azaspiro[3.4]octane of higher polarity.

EXAMPLE 20

(–)-7-(8-amino-6-azaspiro[3.4]octane-6-yl)-8-chloro-6-fluoro-1-(1,2-cis-2-fluoro-1-cyclopropyl)-1,4-dihydro-4-oxoquinoline-3-carboxylic acid (58b):

To a solution of 412 mg of the carboxylic acid (12b) found in Ref. Ex. 17 in 10 ml of anhydrous acetonitrile there were then added 409 mg of the 8-tertbutoxycarbonylamino-6-azaspiro[3.4]octane obtained in Ref. Ex. 38-12 and 2 ml of triethylamine, and the mixture was heated under reflux for 20 hr. The solvent was removed under reduced pressure. To the residue was added 3 ml of conc. hydrochloric acid and the mixture was stirred at room temperature for 1 hr. The mixture was then washed with chloroform and the resulting aqueous layer was made alkaline to pH 10 by adding thereto a sodium hydroxide aqueous solution. The mixture was washed with chloroform and the aqueous layer was adjusted to a pH of 7 by adding conc. hydrochloric acid then dilute hydrochloric acid. The aqueous laser was extracted with chloroform and the extract was dried. The solvent was removed under reduced pressure. The residue was purified by recrystallization from a mixture of aqueous ammonia and ethanol to yield about 300 mg of the crude titled product. About 200 mg of the crude product was purified by preparative TLC using a developing solvent of a mixture of CHCl$_3$:MeOH:H$_2$O=7:3:1(v/v) and 130 mg of the titled compound was obtained after recrystallization of the material obtained by preparative TLC purification from a mixture of aqueous ammonia and ethanol.

mp; 135°–141° C.

[α]$_D$ −152.43° (c=0.925, 1N NaOH)

Reference Example 39-1

N-[1-(R)-Phenylethyl]-3-oxobutanamide

To a solution of 31 g of (R)-D-(+)-phenylethylamine in 84 ml of dry dichloromethane was added dropwise a solution of 21 g of diketene in 15 ml of dry dichloromethane on an ice bath. During the addition, the highest temperature of the reaction mixture was 15° C. The reaction mixture was stirred at room temperature for 15 hr. The mixture was washed with a 10% (w/v) citric acid aqueous solution and then with a saturated sodium bicarbonate aqueous solution and then dried. Solvent was removed under reduced pressure to yield 53.7 g of the titled compound.

$^1$H-NMR(CDCl$_3$) δ ppm;1.48(3H, d, J=5.4 Hz), 2.24(3H, s), 3.40(2H, s), 5.14(1H, q, J=5.4 Hz), 7.35(5H, s)

Reference Example 39-2

2,2-Dimethyl-N-[1-(R)-phenylethyl]-3-oxo-butanamide

To a solution of 48.5 g of N-[1-(R)-Phenylethyl]-3-oxobutanamide in 250 ml of dry N,N-dimethylformamide was added 84 g of methyl iodide. To the resulting mixture was added 65.3 g of potassium carbonate under ice cooling, and then the mixture was stirred at room temperature for one week. Insoluble material was removed by filtration and the filtrate was concentrated to dryness. Water was added to the residue and the resulting mixture was extracted with ethyl acetate. The extract was washed with water and dried. Solvent was removed under reduced pressure to yield 50 g of crude crystalline titled product. The crude product was washed with isopropyl ether to yield 33 g of the titled product.

$^1$H-NMR(CDCl$_3$) δ ppm;1.40(3H, s), 1.42(3H, s), 1.50(3H, d), 2.17(3H, s), 5.08(1H, q, J=5.4 Hz), 7.32(5H, s)

Reference Example 39-3

2-Methyl-2-[1-methyl-1-[N-(R)-1-phenylethyl]carbmoyl]ethyl]-1,3-dixolane

To a solution of 11.65 g of 2,2-Dimethyl-N-[1-(R)-phenylethyl]-3-oxo-butanamide in 220 ml of benzene were added 18 g of ethylene glycol and 1 g of p-toluenesulfonic acid. The mixture was heated under reflux for 3 days. During the reaction, water formed was removed using Dean-Stark apparatus. After cooling, the reaction mixture was poured into a saturated sodium bicarbonate aqueous solution and the organic layer which resulted was separated. This organic layer was dried, and solvent was removed under reduced pressure to yield 15.2 g of the titled compound.

$^1$H-NMR(CDCl$_3$) δ ppm;1.20(3H, s), 1.22(3H, s), 1.23(3H, s), 1.50(3H, d, j=5.4 Hz), 3.95(4H, s), 5.12(1H, q, J=5.4 Hz), 7.12(1H, brs), 7.32(5H, s)

Reference Example 39-4

2-Bromomethyl-2-[1-methyl-1-[N-(R)-phenylethyl]carbamoyl]ethyl-1,3-dixolane

To a solution of 37.68 g of 2-methyl-2-[1-methyl-1[N-(R)-phenylethyl]carbamoyl]ethyl]-1,3-dixolane in 400 ml of 1,4-dixoane there was dropwise added 22 g of bromine and the mixture was then stirred at room temperature for about 4 hrs. Solvent was removed under reduced pressure, and chloroform was added to the residue. The resulting mixture was washed with a saturated sodium bicarbonate aqueous solution, then with a 5%(w/w) sodium thiosulfate aqueous solution and finally with water and then dried. Solvent was removed under reduced pressure to yield 45.25 g of the titled compound.

$^1$H-NMR(CDCl$_3$) δ ppm;1.24 (3H,d, J=3.6 Hz), 1.42(3H, s), 1.54(3H, s), 3.58(2H, ABq, J=10.8 Hz), 3.90–4.50(4H, m), 5.05(1H, q, J=3.6 Hz), 7.00(1H, br.s), 7.30(5H, s)

Reference Example 39-5

9,9-Dimethyl-8-oxo-7-[1-(R)-phenylethyl]-7-aza-1,4-diazaspiro[4.4]nonane

To a solution of 45.25 g of 2-bromomethyl-2-[1-methyl-1-[N-(R)-phenylethyl]carbamoyl]ethyl-1,3-dixolane in 150 ml of dry N N-dimethylformamide there was added 6.5 g of 60% sodium hydride and the mixture was stirred at room temperature for 18 hrs. The reaction mixture was then poured into ice water and the mixture was extracted with benzene. The extract was washed with water and then dried. Solvent was removed under reduce pressure. The residue was purified by chromatography through 250 g of silica gel in a column while eluting with a mixture of n-hexane and ethyl acetate (3:1, v/v) to yield 18.23 g of the titled compound.

$^1$H-NMR(CDCl$_3$) δ ppm;1.18 (3H, d, J=4.0 Hz), 1.50, 1.58 (each 3H, s), 3.04 (2H, ABq, J=10 Hz), 3.75–4.10 (4H, m), 5.60 (1H, q, J=4 Hz), 7.32 (5H, s)

Reference Example 39-6

3,3-Dimethyl-1-[1-(R)-phenylethyl]-pyrrolidin-2,4-dione

A mixture of 18.23 g of 9,9-dimethyl-8-oxo-7-[1-(R)-phenylethyl]-7-aza-1,4-dioxaspiro[4.4]nonane, 70 ml of 1N hydrochloric acid and 20 g of p-toluenesulfonic acid in 250 ml of acetone was heated under reflux for 20 hrs. During the reaction, 20 g of p-toluenesulfonic acid was further added. Solvent was removed under reduced pressure and the residue was extracted with chloroform. The extract was washed with a saturated sodium bicarbonate aqueous solution and dried. Solvent was removed under reduced pressure, and the residue was purified by silica gel chromatography (300 g of silica gel in a column) while eluting with a mixture of n-hexane and ethyl acetate (4:1, v/v) to yield 11.85 g of the titled compound.

$^1$H-NM(CDCl$_3$) δ ppm;1.20, 1.26 (each 3H, s), 1.60 (2H, ABq, J=16 Hz), 5.80 (1H, q, J=7.2 Hz ), 7.32 (5H, s)

Reference Example 39-7

3-3-Dimethyl-4-hydroxyimino-1-[1-(R)-phenylethly]pyrrolidin-2-one

To a solution of 11.85 g of 3,3-dimethyl-1-[1-(R)-phenyethyl]-pyrrolidin-2,4-dione in 100 ml of ethanol there were added 8 g of hydroxylamine hydrochloride and 45 ml of triethylamine. The mixture was heated under reflux with stirring for 1 hr. Solvent was removed under reduced pressure, and the residue was extracted with chloroform. The extract was washed with a 10% (w/v) citric acid aqueous solution and then with water and then dried. Solvent was removed under reduced pressure to give 11.5 g of the titled compound.

$^1$H-NMR(CDCl$_3$) δ ppm;1.30, 1.34(each 3H, s), 1.58(3H, d, J=7.2 Hz), 3.90(2H, ABq, J=16.2 Hz), 5.65(1H, q, J=7.2 Hz), 7.36(5H, s)

Reference Example 39-8

4-Amino-3,3-dimethyl-1-[1-phenylethyl]-pyrrolidin-2-one

To a solution of 8.75 g of 3,3-dimethyl-4-hydroxyimino-1-[1-(R)-phenylethyl]-pyrrolidin-2-one in 300 ml of methanol there was added 20 ml of Raney-nickel, and reduction was carried out under a hydrogen atmosphere at room temperature for 16 hr (H$_2$ pressure: 1 atm). The catalyst was removed by filtration and the solvent of the filtrate was removed under reduced pressure. The residue was purified through column chromatography using a column filled with 300 g of silica gel. From a fraction eluted with a mixture of methanol and chloroform(1:30, v/v), 3.75 g of the less polar isomer of the titled compound was obtained along with 10.2 g of a mixture of the less polar and more polar titled compound.

$^1$H-NMR(CDCl$_3$) (of less polar isomer) δ ppm; 0.95, 1.18 (each 3H, s), 1.52(3H, d, J=7.2 Hz), 2.40–2.55(1H, m), 3.00–3.50(2H, m), 5.52(1H, q, J=7.2 Hz), 7.30(5H, s)

Reference Example 39-9

4-Amino-3,3-dimethyl-1-[1-(R)-phenylethyl]-pyrrolidine (from the less polar amino compound):

To an ice cooled solution of 3.7 g of 4-amino-3,3-dimethyl-1-[1-(R)-phenylethyl]-pyrrolidin-2-one in 150 ml of anhydrous tetrahydrofuran there was gradually added 2 g of lithium aluminum hydride and then the mixture was heated under reflux for 2.5 hr. After cooling on ice, 2 ml of water, 2 ml of a 15%(w/w) aqueous sodium hydroxide solution and 6 ml of water were added to the ice cooled reaction mixture (in that order). Insoluble material was removed by filtration, and the solvent of the filtrate was removed under reduced pressure to yield 3.69 g of the titled compound. This product was used in the following reaction without further purification.

Reference Example 39-10

4-tert-Butoxycarbonylamino-3,3-dimethyl-1-[1-(R)-phenylethyl]-pyrrolidine

To an ice cooled solution of 3.69 g of 4-amino-3,3-dimethyl-1-[1-(R)-phenylethyl]-pyrrolidine in 40 ml of anhydrous tetrahydrofuran there was added 4.92 g of 2-(tert-butoxycarbonylamino)-2-phenylacetonitrile and the mixture was stirred at room temperature for 1 hr. Solvent was removed under reduced pressure, and to the residue there was added ethyl acetate. The mixture was washed with a 1N sodium hydroxide aqueous solution three times and then dried. Solvent was then removed under reduced pressure. The residue was purified through column chromatography using 200 g of silica gel in a column with chloroform as the eluant containing from 1% to 5% methanol to yield 4.32 g of the titled compound.

$^1$H-NMR(CDCl$_3$) δ ppm;1.00, 1.16(each 3H, s), 1.40(3H, d, J=7.2 Hz), 1.52(9H, s), 2.00–3.62(5H, m), 3.85–4.10(1H, m), 4.90(1H, bs), 7.38(5H, s)

Reference Example 39-11 tert-Butoxycarbonylamino-3,3-dimethyl-pyrrolidine

To a solution of 4.32 g of 4-tert-butoxycarbonlamino-3,3-dimethyl-1-[1-(R)-phenylethyl]-pyrrolidine in 90 ml of ethanol thee was added 4 g of 10% palladium on charcoal and reduction was carried out under a hydrogen atmosphere (H$_2$ pressure: 4 atm) for 7 hrs. During the reduction, the reaction vessel was warmed by irradiation with a tungsten lamp. The catalyst was removed by filtration and the solvent of the filtrate was removed under reduced pressure. To the resulting residue there was added ethyl acetate and the mixture was washed with a 10%(w/v) citric acid aqueous solution twice. The citric acid layer which resulted was rendered alkaline by adding a sodium hydroxide aqueous solution. The resulting mixture was then extracted with chloroform. The resulting extract was dried and the solvent was removed under reduced pressure to yield 2.5 g of the titled compound.

$^1$H-NMR(CDCl$_3$) δ ppm;0.98, 1.08(each 3H, s), 1.48(9H, s), 2.30–4.00(6H, m), 4.50(1H, br.s)

EXAMPLE 21

(−)-7-(4-Amino-3,3-dimethyl-1-pyrrolidinyl)-8-chloro-6-fluoro-1-[2-(S)-fluoro-1-(R)-cyclopropyl]-1,4-dihydro-4-oxoquinoline-3-carboxylic acid (59b):

To a solution of 476 mg of carboxylic acid (12b) in 15 ml of anhydrous acetonitrile there were added 800 mg of the less polar isomer of 4-tert-butoxycarbonylamino-3,3-dimethyl-pyrrolidine obtained in REFERENCE EXAMPLE 39-11 and 2 ml of triethylamine, and the mixture was heated under reflux for 6.5 hrs. Solvent was then removed under reduced pressure. The residue was purified through column chromatography using 150 g of silica gel using as eluents chloroform containing 3,5 and 10%(v/v) of methanol and with CHCl$_3$:MeOH:H$_2$O=7:3:1(v/v) to yield 7-(4-tertbutoxycarbonylamino-3,3-dimethyl-1-pyrrolidinyl)-8-chloro-6-fluoro-1-[2-(S)-fluoro-1-(R)-cyclopropyl]-1,4-dihydro-4-oxoquinoline-3-carboxylic acid. This material was recrystallized from a mixture of n-hexane and ethyl acetate to yield 550 mg of the crystalline product. To this crystalline product there was added concentrated hydrochloric acid and the mixture was stirred at room temperature for 1 hr. The mixture was washed with chloroform and to the aqueous layer which resulted was added a sodium hydroxide aqueous solution until the pH became 7. The mixture was then extracted with chloroform and the extract was dried. Solvent was then removed under reduced pressure and the product in the residue was purified by preparative TLC using a mixture of CHCl$_3$:MeOH:H$_2$O=7:3:1(v/v) as a developing solvent. As a result, 170 mg of the titled compound was obtained after recrystallization of the material obtained by preparative TLC purification from a mixture of aqueous ammonia and ethanol.

mp;118°–121° C.

[α]$_D$ 13.08. (c=0.764, 1N NaOH)

Anal. Calcd. for C$_{19}$H$_{20}$N$_3$O$_3$F$_2$Cl: C, 55.41; H, 4.89; N, 10.20 Found: C, 55.22; H, 4.93; N, 9.69

Reference Example 40

1) Diethyl cyclobutylidenemalonate (compound 60)

A solution of 15.68 ml of titanium tetrachloride in 35.7 ml of carbon tetrachloride was rapidly dropwise added to 285 ml of tetrahydrofuran which was cooled to −30° C. while stirring the system. 5 g of cyclobutanone and 10.83 g of diethyl malonate were then added to the mixture. A solution of 23.1 ml of pyridine in 50 ml of tetrahydrofuran was then dropwise added thereto over 1 hour while the temperature of the reaction mixture was maintained below −10° C. The mixture was stirred for 18 hours keeping the temperature of the mixture at about 0° C. Water was added to the mixture and the mixture was then extracted with diethyl ether. The resulting ether layer was separated and the remaining aqueous layer was extracted with diethyl ether. The combined organic layers were washed with a saturated sodium chloride aqueous solution, a saturated sodium bicarbonate aqueous solution and a saturated sodium chloride aqueous solution in that sequence. The resulting organic layer was dried over anhydrous sodium sulfate. Solvent was then removed under reduced pressure to yield 17.265 g of the titled compound 60 as a colorless oil.

$^1$H-NMR (CDCl$_3$) δ ppm: 1.29 (6H, 6, J=7.3 Hz), 1.7–2.4 (2H, m), 3.15 (4H, t, J=7.7 Hz), 4.22 (4H, q, J=7.3 Hz)

By a similar procedure, diethyl cyclopentylidenemalonate (compound 61) ($^1$H-NMR (CDCl$_3$) δ ppm: 1.29 (6H, t, J=7 Hz), 1.6–2.0 (4H, m), 2.6–2.8 (4H, m), 4.24 (4H, q, J=7 Hz)) and diethyl cyclohexylidenemalonate (compound 62) ($^1$H-NMR (CDCl$_3$) δ ppm: 1.28 (6H, t, J=7.2 Hz), 1.4–1.85 (6H, br), 2.3–2.6 (4H, br), 4.22 (4H, q, J=7.2 Hz)) were obtained.

2) Diethyl (1-nitromethyl-1-cyclobutyl) malonate (compound 63)

A mixture of 15.32 g of compound 60, 59 ml of nitromethane and 4.5 ml of tetramethylguanidine was stirred at room temperature for 16 hours. To the mixture was added a 10% citric acid aqueous solution and the mixture was shaken. The organic layer was separated and washed with a saturated sodium chloride aqueous solution and then dried over anhydrous sodium sulfate. Solvent was removed under reduced pressure to yield 19.03 g of titled compound 63 as a yellow oil.

$^1$H-NMR (CDCl$_3$) δ ppm: 1.29 (6H, t, J=7.1 Hz), 1.8–2.4 (6H, m), 3.80 (1H, s), 4.20 (4H, q, J=7.1 Hz), 4.82 (2H, s)

Using a similar procedure, diethyl (1-nitro-methyl-1-cyclopentyl)malonate (compound 64) ($^1$H-NMR (CDCl$_3$) δ ppm: 1.27 (6H, t, J=7 Hz), 1.6–2.0 (8H, m), 3.79 (1H, s), 4.20 (4H, q, J=7 Hz), 4.71 (2H, s)) and diethyl (1-nitromethyl-1-cyclohexyl)malonate (compound 65) ($^1$H-NMR (CDCl$_3$) δ ppm: 1.27 (6H, t, J=7 Hz), 1.4–1.8 (10H, m), 3.88 (1H, s), 4.20 (4H, q, J=7 Hz), 4.96 (2H, s) were obtained.

Ethyl 7-oxo-6-azaspiro[3.4]octane-8-carboxylate (compound 66)

30 ml of Raney nickel which had been washed with water and ethanol was added to a solution of 19.03 g of compound 63 in 400 ml of ethanol. Catalytic reduction was then conducted for 2 days at room temperature (H$_2$ pressure: 1 atm). The catalyst was removed by filtration and solvent was removed under reduced pressure. To the residue were added ethyl acetate and 1N hydrochloric acid and the mixture was shaken. The organic layer was dried over anhydrous sodium sulfate and solvent was removed under reduced pressure. The residue was purified by silica gel column chromatography (100 g of silica gel) while eluting with chloroform containing 0–3% methanol to yield 2.97 g of titled compound 66. The hydrochloric acid layer which resulted was neutralized with sodium bicarbonate and the mixture was extracted with ethyl acetate. The organic layer which resulted was dried over anhydrous sodium sulfate and solvent was removed under reduced pressure to yield 1.58 g of titled compound 66. Finally, 4.56 g total of titled compound 66 was obtained.

$^1$H-NMR (CDCl$_3$) δ ppm: 1.28 (3H, t, J=7.1 Hz), 1.8–2.2 (6H, m), 3.21 (1H, s), 3.41 (1H, dd, J=9.7 & 1.4 Hz), 3.60 (1H, d, J=9.7 Hz), 4.20 (2H, q, J=7.1 Hz), 7.21 (1H, br)

By a similar procedure, ethyl 3-oxo-2-azaspiro[4.4]nonane-4-carboxylate (compound 67) ($^1$H-NMR (CDCl$_3$) δ ppm: 1.28 (3H, t, J=7.3 Hz), 2.6–2.8 (8H, br), 3.07 (1H, s), 3.01 (1H, dd, J=9.3 & 1.3 Hz), 3.45 (1H, d, J=9.3 Hz), 4.20 (2H, q, J=7.3 Hz), 7.30 (1H, br)) and ethyl 3-oxo-2-azaspiro[4.5]decane-4-carboxylate (compound 68) ($^1$H-NMR (CDCl$_3$) δ ppm: 1.29 (3H, t, J=7.3 Hz), 1.3–1.7 (10H, br), 3.05 (1H, s), 3.17 (1H, dd, J=9.9 & 1.4 Hz), 4.20 (2H, q, J=7.3 Hz), 7.30 (1H, br)) were obtained.

4) 7-Oxo-6-azaspiro3.4octane-8-carboxylic acid (compound 69)

20 ml of water and 0.8 g of sodium hydroxide were added to a solution of 1.97 g of compound 66 in 20 ml of ethanol. The resulting was refluxed for 2 hours. Ethanol was removed under reduced pressure and the aqueous layer which resulted was washed with chloroform. The aqueous layer was neutralized with 1N hydrochloric acid while ice cooling. The aqueous layer was then extracted with 2-butanone, and the extract was dried over anhydrous magnesium sulfate. Solvent was removed to yield 1.57 g of titled compound 69 as colorless crystals.

$^1$H-NMR (CDCl$_3$) δ ppm: 1.6–2.7 (6H, m), 3.15 (1H, s) 3.40 (1H, d, J=9.2 Hz), 3.60 (1H, d, J=9.2 Hz), 6.2 (1H, br)

By a similar procedure, 3-oxo-2-azaspiro-[4.4]nonane-4-carboxylic acid (compound 70) ($^1$H-NMR (CDCl$_3$) δ ppm: 1.5–2.3 (8H, m), 3.15 (1H, d, J=9.5 Hz), 3.28 (1H, s), 3.33 (1H, d, J=9.5 Hz), 6.45 (1H, br)) and 3-oxo-2-azaspiro[4.5]decane-4-carboxylic acid (compound 71) $^1$H-NMR (CDCl$_3$) δ ppm: 1.2–2.0 (10H, m), 3.06 (1H, s), 3.11 (1H, d, J=9.8 Hz), 3.48 (1H, d, J=9.8 Hz), 6.47 (1H, br)) were obtained.

5) 8-tert-Butoxycarbonylamino-7-oxo-6-azaspiro[3.4]octane (compound 72)

2.2 ml of diphenyl phosphorylazide and 1.55 ml of triethylamine were added to a suspension 1.57 g of compound 69 in 20 ml of benzene with stirring. The resulting mixture was refluxed for 1.5 hours. Then, 4.4 ml of tert-butanol was added to the mixture and the mixture was refluxed for 16 hours. The solvent was removed under reduced pressure. The residue was extracted with ethyl acetate and the extract was washed with a saturated sodium bicarbonate aqueous solution, a saturated sodium chloride aqueous solution a 10% (v/w) citric acid aqueous solution and a saturated sodium chloride aqueous solution in that order. The washings were extracted with ethyl acetate and the combined extracts were dried over anhydrous sodium sulfate. Solvent was then removed under reduced pressure. The residue was purified by silica gel column chromatography (50 g of silica gel) while eluting with chloroform containing 0–3% methanol to yield 0.56 g of titled compound 72.

$^1$H-NMR (CDCl$_3$) δ ppm: 1.48 (9H, s), 1.5–2.5 (6H,m) 3.27 (1H, d, J=9.9 Hz), 3.44 (1H, d, J=9.9 Hz), 4.18 (1H, d, J=7.7 Hz), 5.20 (1H, d, J=7.7 Hz), 7.13 (1H, br s)

By a similar procedure, 4-tert-butoxy-carbonylamino-3-oxo-2-azaspiro[4.4]nonane (compound 73) ($^1$H-NMR (CDCl$_3$) δ ppm: 1.45 (9H, s), 1.2–1.8 (8H, m), 3.13 (2H, s), 4.35 (1H, d, J=7.9 Hz), 5.15 (1H, d, J=7.9 Hz), 7.21 (1H, br s)) and 4-tert-butoxycarbonyl-amino-3-oxo-2-azaspiro[4.5]decane (compound 74) ($^1$H-NMR (CDCl$_3$) δ ppm: 1.46 (9H, s), 1.0–1.8 (10H, m), 2.9–3.4 (2H, m), 4.15 (1H, d, J =8.6 Hz), 4.89 (1H, d, J=8.6 Hz), 6.71 (1H, br s)) were obtained.

6) 6-tert-Butoxycarbonyl-8-tert-butoxycarbonylamino-6-azaspiro[3.4]octane (compound 77)

15 ml of trifluoroacetic acid was added to 560 mg of ice cooled compound 72 while stirring. The mixture was then stirred at room temperature for 1.5 hours. The trifluoroacetic acid was then removed under reduced pressure and the residue was dissolved in 30 ml of anhydrous tetrahydrofuran. The solution was cooled over ice and 884 mg of lithium aluminum hydride was added to the mixture. The mixture was then refluxed for 16 hours. The mixture was cooled with ice and then water was added with stirring. Insoluble material was removed by filtration and the collected material was washed with tetrahydrofuran. The filtrate and washings of the collected material were combined and there was added thereto 1.02 g of di-tertbutyl dicarbonate. The resulting mixture was stirred at room temperature for 16 hours. Solvent was then removed under reduced pressure. The residue was purified by silica gel column chromatography (50 g of silica gel) while eluting with a mixture of ethyl acetate and n-hexans (1:10 v/v) to yield 273 mg of titled compound 77.

$^1$H-NMR (CDCl$_3$) δ ppm: 1.45 (18H, s), 1.7–2.1 (6H, m), 3.0–3.6 (4H, m), 3.8–4.2 (1H, m), 5.1 (1H, br d)

By a similar procedure, 2-tert-butoxy-carbonyl-4-tert-butoxycarbonylamino-2-azaspiro[4,4]-nonane (compound 80) (3.27 (1H, d, J=9.9 Hz), 3.44 (1H, d, J=9.9 Hz), ($^1$H-NMR (CDCl$_3$) δ ppm: 1.45 (18H, s), 1.3–1.8 (8H, m), 3.0–3.3 (3H, m), 3.4–3.7 (1H, m), 3.7–4.1 (1H, m), 4.55 (1H, br d)) and 2-tert-butoxy-carbonyl-4-tert-butoxycarbonylamino-2-azaspiro[4,5]-decane (compound 83) ($^1$H-NMR (CDCl$_3$) δ ppm: 1.0–1.9 (28H, m), 2.9–4.1 (5H, m), 4.51 (1H, br d)) were obtained.

REACTION SCHEME

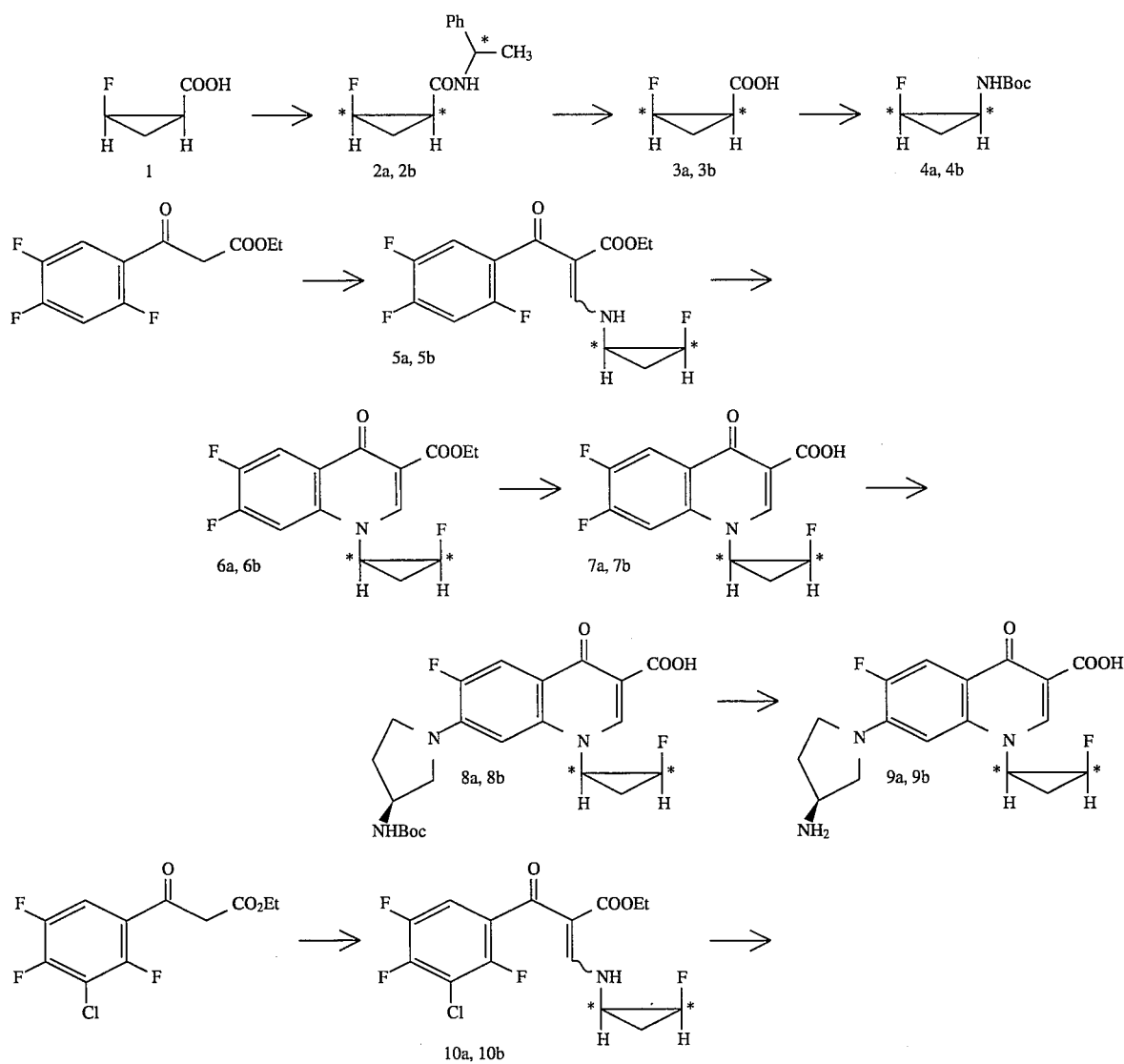

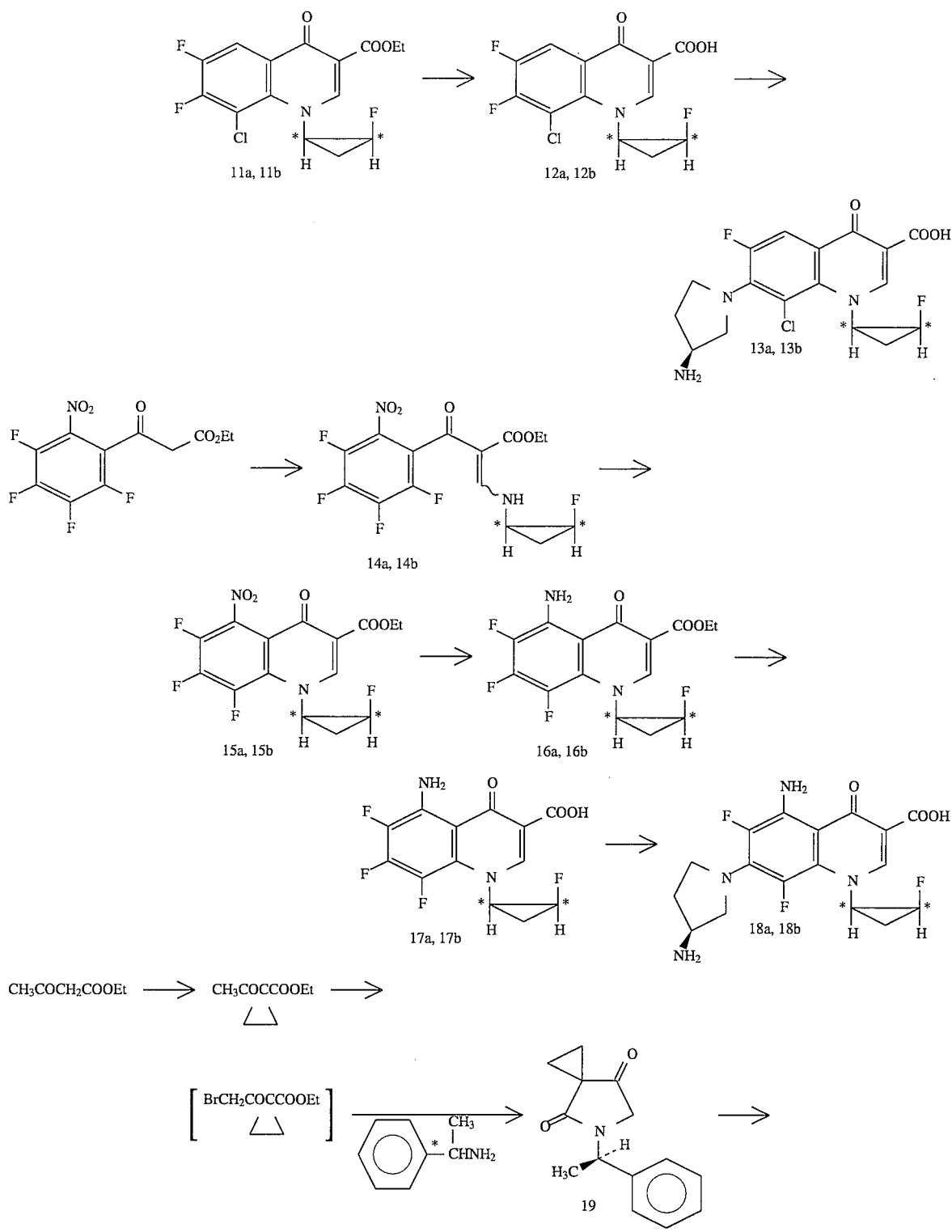
-continued
REACTION SCHEME

-continued
REACTION SCHEME
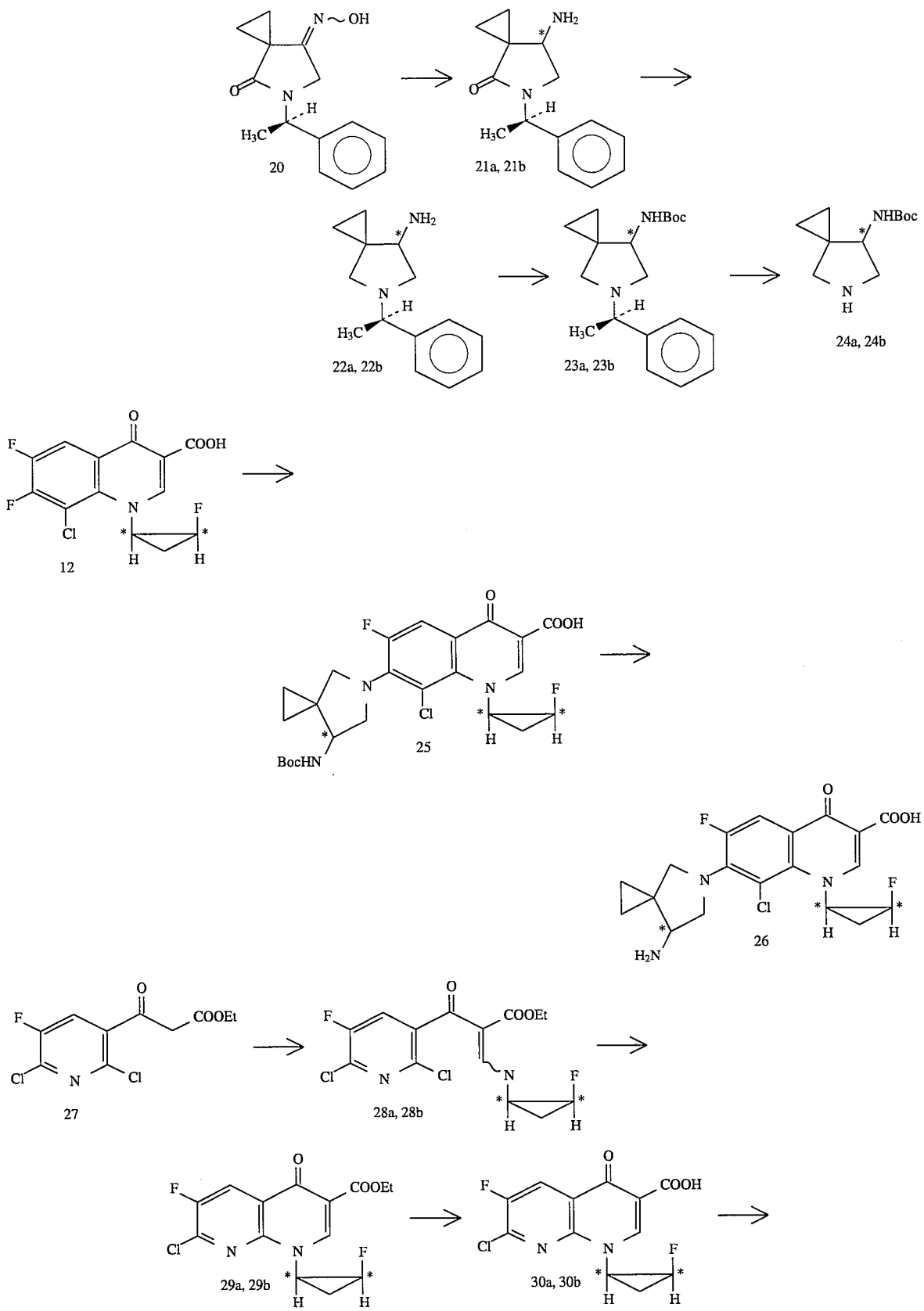

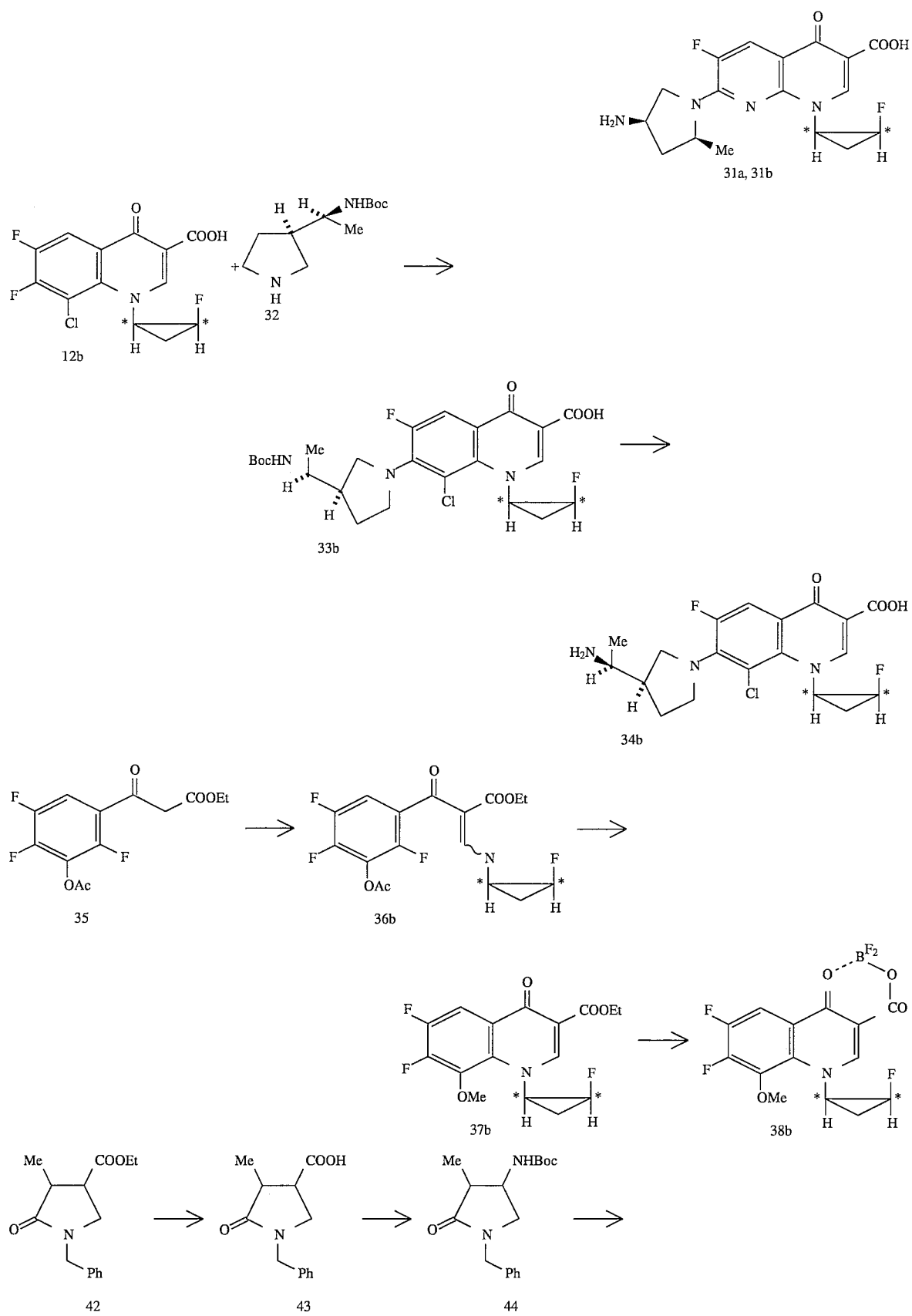

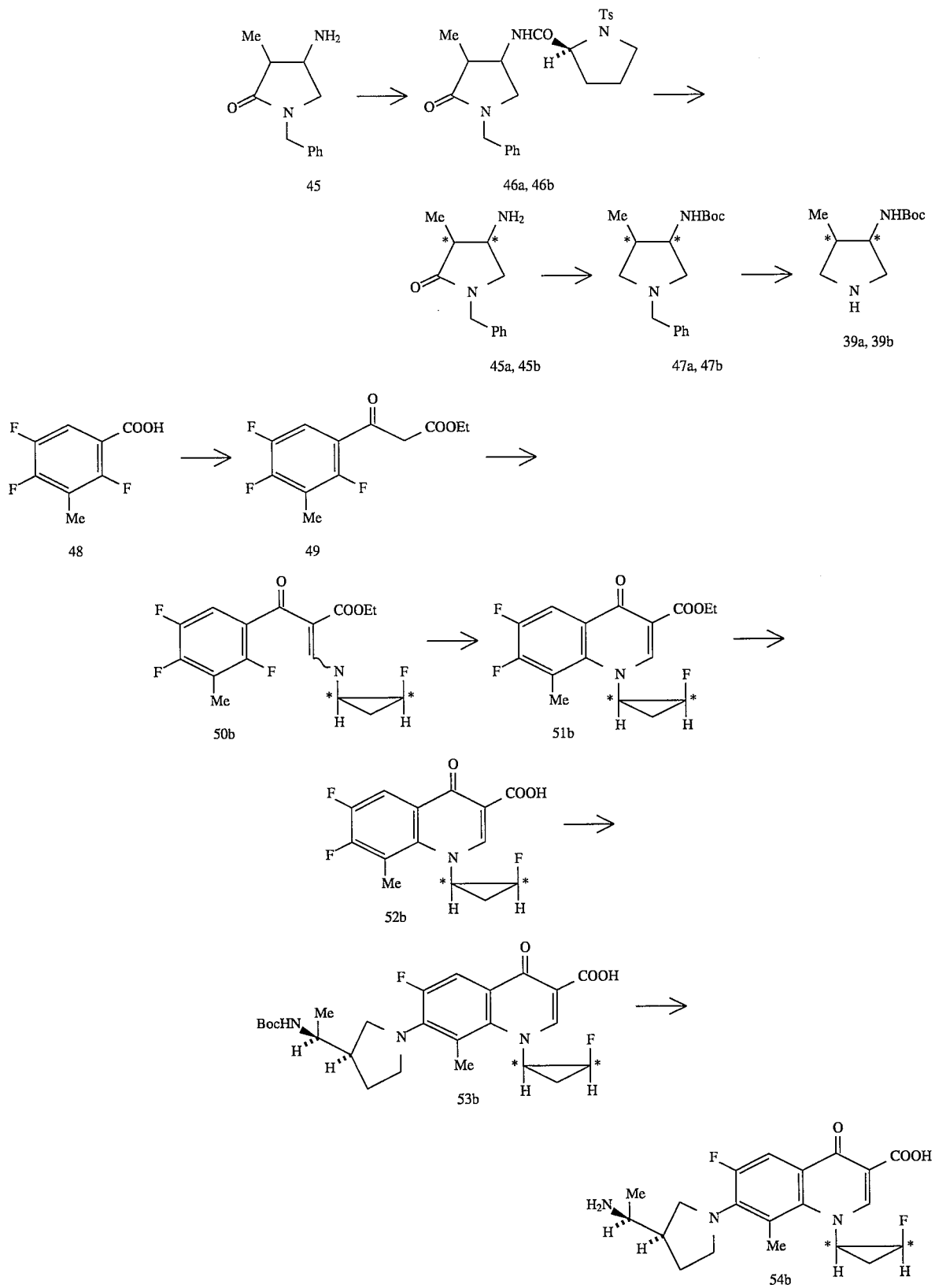

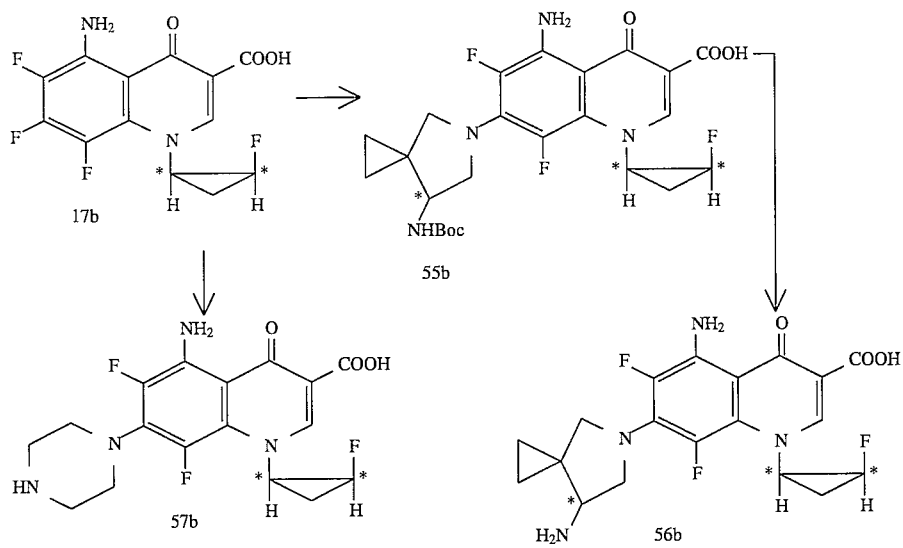
Another synthesis route of amino substituted azabicyclalkane.
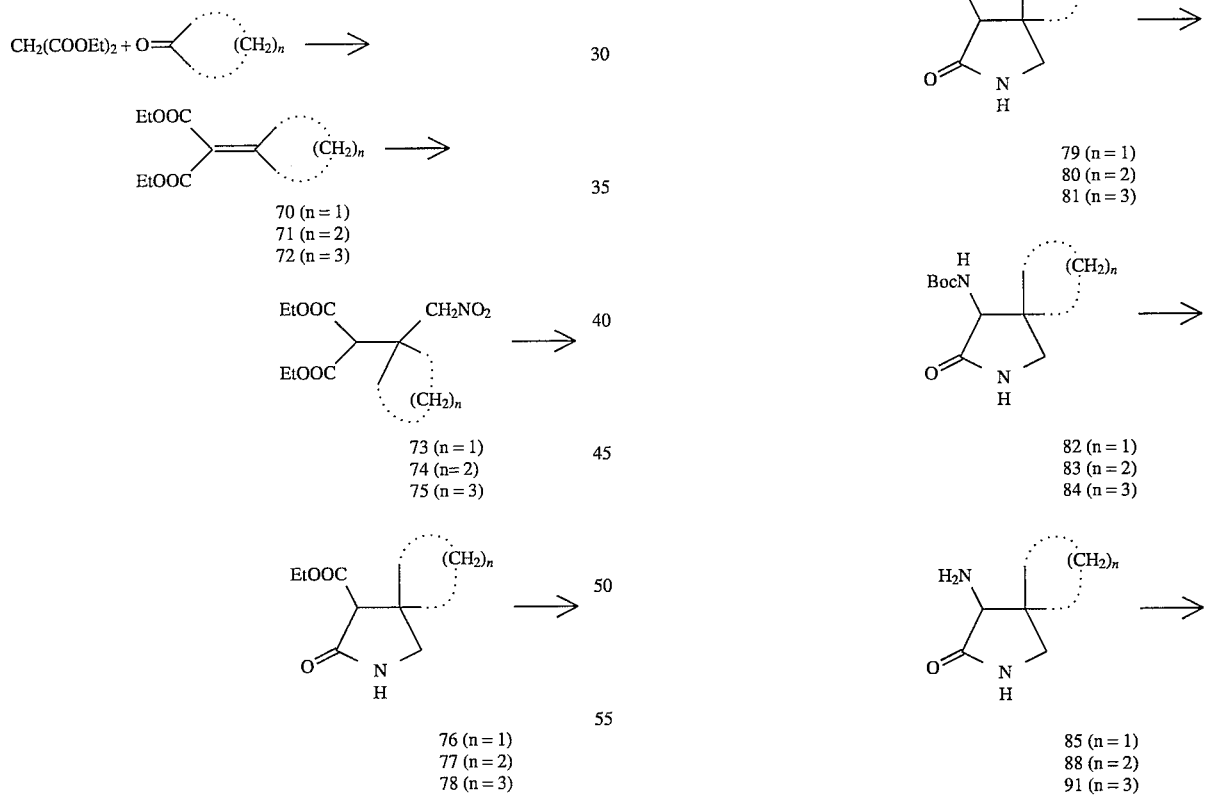

69
-continued

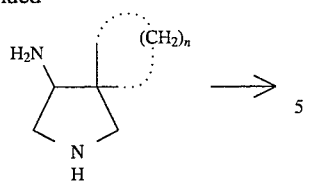

86 (n = 1)
89 (n = 2)
92 (n = 3)

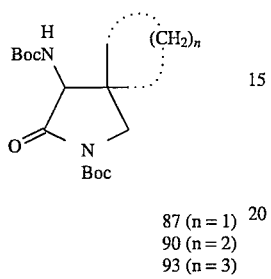

87 (n = 1)
90 (n = 2)
93 (n = 3)

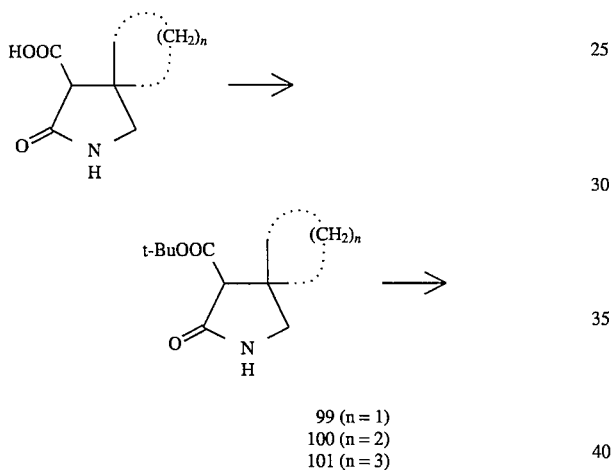

99 (n = 1)
100 (n = 2)
101 (n = 3)

70
-continued

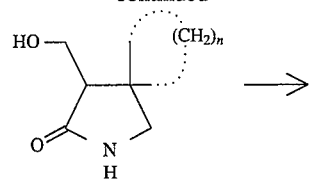

102 (n = 1)
104 (n = 2)
106 (n = 3)

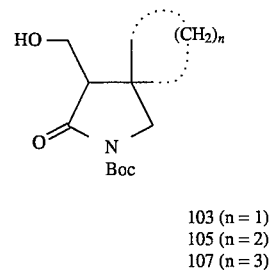

103 (n = 1)
105 (n = 2)
107 (n = 3)

TABLE 1

| Antimicrobial activity (M I C, μg/ml) | | | | | | | | |
|---|---|---|---|---|---|---|---|---|
| bacteria\Compound | 9a | 9b | 13a | 13b | 18a | 18b | 26bb | 26aa |
| *E. coli.*, NIHJ | 0.10 | <0.1 | <0.1 | <0.1 | <0.1 | <0.1 | <0.1 | <0.1 |
| *Pr. vulgaris*, 08601 | <0.1 | <0.1 | <0.1 | <0.1 | <0.1 | <0.1 | <0.1 | <0.1 |
| *Ser. marcescens*, 10100 | 0.20 | 0.10 | <0.1 | <0.1 | <0.1 | <0.1 | <0.1 | 0.10 |
| *Ps. aeruginosa*, 32104 | 0.39 | 0.10 | <0.1 | <0.1 | <0.1 | <0.1 | <0.1 | 0.39 |
| *Ps. aeruginosa*, 32121 | 0.10 | <0.1 | <0.1 | <0.1 | <0.1 | <0.1 | <0.1 | 0.10 |
| *S. aureus*, 209 P | 0.10 | <0.1 | <0.1 | <0.1 | <0.1 | <0.1 | <0.1 | <0.1 |
| *S. epidermidis*, 56500 | 0.39 | 0.39 | <0.1 | <0.1 | <0.1 | <0.1 | <0.1 | 0.20 |
| *Str. faecalis*, ATCC 19433 | 1.57 | 0.79 | 0.20 | 0.20 | 0.20 | 0.10 | 0.20 | 0.39 |
| bacteria\Compound | 26ba | 26ab | 31b | 34b | 54b | 56b | 58b | 59b |
| *E. coli.*, NIHJ | <0.1 | <0.1 | <0.1 | <0.1 | <0.1 | <0.1 | <0.1 | <0.1 |
| *Pr. vulgaris*, 08601 | <0.1 | <0.1 | <0.1 | <0.1 | <0.1 | <0.1 | <0.1 | <0.1 |
| *Ser. marcescens*, 10100 | <0.1 | <0.1 | <0.1 | <0.1 | 0.10 | <0.1 | <0.1 | <0.1 |
| *Ps. aeruginosa*, 32104 | 0.20 | 0.20 | 0.20 | 0.10 | 0.20 | <0.1 | 0.10 | 0.20 |
| *Ps. aeruginosa*, 32121 | 0.10 | <0.1 | 0.10 | 0.10 | 0.10 | <0.1 | <0.1 | <0.1 |
| *S. aureus*, 209 P | <0.1 | <0.1 | <0.1 | <0.1 | <0.1 | <0.1 | <0.1 | <0.1 |
| *S. epidermidis*, 56500 | 0.20 | 0.10 | 0.20 | <0.1 | 0.10 | <0.1 | <0.1 | 0.10 |
| *Str. faecalis*, ATCC 19433 | 0.39 | 0.20 | 0.39 | <0.1 | 0.10 | 0.10 | <0.1 | 0.10 |

While the invention has been described in detail and with reference to specific embodiments thereof, it will be apparent to one skilled in the art that various changes and modifications can be made therein without departing from the spirit and scope thereof.

What is claimed is:

1. A stereoisomerically pure $N_1$-(1,2-cis-2-halogenocyclopropyl)-substituted pyridonecarboxylic acid derivative represented by the following formula (I):

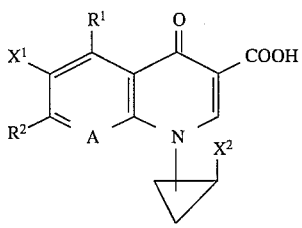

wherein $R^1$ represents a hydrogen atom, an amino group, a hydroxyl group or a thiol group;

$R^2$ represents a substituent represented by the following formula:

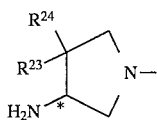

wherein $R^{23}$ and $R^{24}$ together are $(CH_2)j$; where $j=2$ to 5;

A represents C—$X^3$ or a nitrogen atom;

$X^1$ and $X^2$, which may be the same or different, each represents a halogen atom;

and $X^3$ represents a halogen atom, an alkyl group of from 1 to 6 carbon atoms, an alkoxyl group from 1 to 6 carbon atoms, a cyano group, a trifluoromethyl group, or a hydrogen atom;

or a pharmaceutically acceptable salt thereof.

2. 7-[7-(S)-Amino-5-azaspiro[2.4]heptan-5-yl]-8-chloro-6-fluoro-1-[2-(S)-2-fluoro-1-(R)-cyclopropyl]-4-oxo-1,4-dihydroquinoline-3-carboxylic acid or a pharmaceutically acceptable salt thereof.

3. A method for treating bacterial infections which comprises administering a therapeutically effective amount of 7-[7-(S)-amino-5-azaspiro[2.4]heptan-5-yl]-8-chloro-6-fluoro-1-[2-(S)-2-fluoro-1-(R)-cyclopropyl]-4-oxo-1,4-dihydroquinoline-3-carboxylic acid or a pharmaceutically acceptable salt thereof.

4. 7-[7-(S)-Amino-5-azaspiro[2.4]heptan-5-yl]-8-chloro-6-fluoro-1-(1,2-cis-2-fluorocyclopropyl)-4-oxo-1,4-dihydroquinoline-3-carboxylic acid or a pharmaceutically acceptable salt thereof.

5. An antibacterial composition comprising a therapeutically effective amount of, as an active ingredient, 7-[7-(S)-amino-5-azaspiro[2.4]heptan-5-yl]-8-chloro-6-fluoro-1-[2-(S)-2-fluoro-1-(R)-cyclopropyl]-4-oxo-1,4-dihydroquinoline-3-carboxylic acid or a pharmaceutically acceptable salt thereof, in combination with a pharmaceutically acceptable carrier.

6. The stereoisometrically pure $N_1$-(1,2-cis-2-halogenocyclopropyl)-substituted pyridonecarboxylic acid derivative of claim 1, wherein $R^2$ represents a 7-amino-5-azaspiro[2,4]-heptan-5-yl group.

7. The stereoisomerically pure $N_1$-(1,2-cis-2-halogenocyclopropyl)-substituted pyridonecarboxylic acid derivative of claim 6, wherein $R^2$ represents a 7-(S)-amino-5-azaspiro[2.4]heptan-5-yl group.

8. The stereoisomerically pure $N_1$-(1,2-cis-2-halogenocyclopropyl)-substituted pyridonecarboxylic acid derivative or a pharmaceutically acceptable salt thereof of claim 1, wherein $R^2$ represents 8-amino-6-azaspiro[3,4]octan-6-yl group.

9. A method for treating bacterial infections which comprises administering a therapeutically effective amount of the stereoisomerically pure $N_1$-(1,2-cis-2-halogenocyclopropyl)-substituted pyridonecarboxylic acid derivative or a pharmaceutically acceptable salt thereof of claim 1, wherein $R^2$ represents 8-amino-6-azaspiro[3,4]octan-6-yl group.

\* \* \* \* \*